(12) United States Patent
Eckhardt et al.

(10) Patent No.: US 7,579,449 B2
(45) Date of Patent: Aug. 25, 2009

(54) GLUCOPYRANOSYL-SUBSTITUTED PHENYL DERIVATIVES, MEDICAMENTS CONTAINING SUCH COMPOUNDS, THEIR USE AND PROCESS FOR THEIR MANUFACTURE

(75) Inventors: Matthias Eckhardt, Biberach (DE); Peter Eickelmann, Mittelbiberach (DE); Frank Himmelsbach, Mittelbiberach (DE); Edward Leon Barsoumian, Toyonaka (JP); Leo Thomas, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 206 days.

(21) Appl. No.: 11/080,150

(22) Filed: Mar. 15, 2005

(65) Prior Publication Data

US 2005/0209166 A1    Sep. 22, 2005

Related U.S. Application Data

(60) Provisional application No. 60/560,239, filed on Apr. 7, 2004.

(30) Foreign Application Priority Data

| Mar. 16, 2004 | (DE) | ......................... 10 2004 012 676 |
| Aug. 18, 2004 | (DE) | ......................... 10 2004 040 168 |
| Dec. 16, 2004 | (DE) | ......................... 10 2004 061 145 |
| Feb. 9, 2005 | (EP) | ................................. 05002628 |

(51) Int. Cl.
*A61K 31/70* (2006.01)
*A61K 31/7004* (2006.01)
*A61K 31/351* (2006.01)
*C07H 7/04* (2006.01)
*C07H 309/10* (2006.01)

(52) U.S. Cl. ..................... 536/1.11; 514/23; 514/460; 549/417

(58) Field of Classification Search ................. 536/1.11; 514/23
See application file for complete search history.

(56) References Cited

U.S. PATENT DOCUMENTS

| 4,602,023 | A | 7/1986 | Kiely et al. |
| 4,786,755 | A | 11/1988 | Kiely et al. |
| 6,414,126 | B1 | 7/2002 | Ellsworth et al. |
| 6,515,117 | B2 | 2/2003 | Ellsworth et al. |
| 6,627,611 | B2* | 9/2003 | Tomiyama et al. ............ 514/23 |
| 6,774,112 | B2 | 8/2004 | Gougoutas |
| 6,936,590 | B2 | 8/2005 | Washburn et al. |
| 7,169,761 | B2 | 1/2007 | Tomiyama et al. |
| 7,202,350 | B2 | 4/2007 | Imamura et al. |
| 7,371,732 | B2 | 5/2008 | Eickelmann et al. |
| 7,375,090 | B2 | 5/2008 | Himmelsbach et al. |
| 7,393,836 | B2 | 7/2008 | Eckhardt et al. |
| 7,417,032 | B2 | 8/2008 | Eckhardt et al. |
| 7,419,959 | B2 | 9/2008 | Eckhardt et al. |
| 2002/0137903 | A1 | 9/2002 | Ellsworth et al. |
| 2003/0064935 | A1 | 4/2003 | Gougoutas |
| 2003/0114390 | A1 | 6/2003 | Washburn et al. |
| 2004/0138148 | A1 | 7/2004 | Fushimi et al. |
| 2004/0138439 | A1 | 7/2004 | Deshpande et al. |
| 2005/0065098 | A1 | 3/2005 | Fujikura et al. |
| 2005/0124555 | A1 | 6/2005 | Tomiyama et al. |
| 2006/0009400 | A1 | 1/2006 | Eckhardt et al. |
| 2006/0019948 | A1 | 1/2006 | Eckhardt et al. |
| 2006/0025349 | A1 | 2/2006 | Eckhardt et al. |
| 2006/0035841 | A1 | 2/2006 | Eckhardt et al. |
| 2006/0063722 | A1 | 3/2006 | Washburn et al. |
| 2006/0074031 | A1 | 4/2006 | Eckhardt et al. |
| 2006/0142210 | A1 | 6/2006 | Eckhardt et al. |
| 2006/0189548 | A1* | 8/2006 | Himmelsbach et al. ....... 514/23 |
| 2006/0234953 | A1 | 10/2006 | Himmelsbach et al. |
| 2006/0251728 | A1 | 11/2006 | Himmelsbach et al. |
| 2006/0258749 | A1 | 11/2006 | Eckhardt et al. |
| 2007/0004648 | A1 | 1/2007 | Himmelsbach et al. |
| 2007/0027092 | A1 | 2/2007 | Himmelsbach et al. |
| 2007/0049537 | A1* | 3/2007 | Eckhardt et al. ............. 514/23 |
| 2007/0054867 | A1 | 3/2007 | Eckhardt et al. |
| 2007/0073046 | A1 | 3/2007 | Eckhardt et al. |
| 2007/0249544 | A1 | 10/2007 | Himmelsbach et al. |
| 2007/0259821 | A1 | 11/2007 | Eckhardt et al. |
| 2008/0058379 | A1 | 3/2008 | Eckhardt et al. |

FOREIGN PATENT DOCUMENTS

CA    2 388 818 A1    4/2001

(Continued)

OTHER PUBLICATIONS

U.S. Appl. No. 11/674,839, filed Aug. 2006, Eckhardt et al.*

(Continued)

*Primary Examiner*—Shaojia Anna Jiang
*Assistant Examiner*—Eric S Olson
(74) *Attorney, Agent, or Firm*—Michael P. Morris; Edouard G. Lebel; David A. Dow

(57) ABSTRACT

Glucopyranosyl-substituted benzene derivatives of general formula I

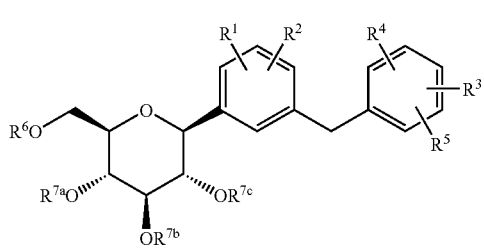

where the groups $R^1$ to $R^6$ as well as $R^{7a}$, $R^{7b}$, $R^{7c}$ are defined herein and the tautomers, the stereoisomers thereof, the mixtures thereof and the salts thereof. The compounds according to the invention are suitable for the treatment of metabolic disorders.

25 Claims, No Drawings

FOREIGN PATENT DOCUMENTS

| | | |
|---|---|---|
| CA | 2 494 177 A1 | 2/2004 |
| CA | 2 508 024 A1 | 6/2004 |
| CA | 2 508 226 A1 | 6/2004 |
| CA | 2 557 269 A1 | 9/2005 |
| CA | 2 557 320 A1 | 9/2005 |
| CA | 2 573 777 A1 | 2/2006 |
| EP | 0 206 567 A2 | 6/1986 |
| EP | 1 344 780 A1 | 9/2003 |
| EP | 1 385 856 A0 | 2/2004 |
| EP | 1224195 B | 5/2005 |
| EP | 1 553 094 A1 | 7/2005 |
| EP | 1 609 785 A1 | 12/2005 |
| JP | 58-164502 A | 9/1983 |
| JP | 62-030750 A | 2/1987 |
| JP | 11/124392 A | 5/1999 |
| JP | 2001-288178 A | 10/2001 |
| JP | 2003-511458 A | 3/2003 |
| JP | 2004/359630 | 12/2004 |
| WO | WO 98/31697 | 7/1998 |
| WO | WO 01/27128 | 4/2001 |
| WO | 01/74834 A1 | 10/2001 |
| WO | 02/064606 A1 | 8/2002 |
| WO | 02/083066 A2 | 10/2002 |
| WO | WO 02/083066 | 10/2002 |
| WO | WO 03/099836 | 12/2003 |
| WO | 2004/013118 A1 | 2/2004 |
| WO | WO 2004/052902 | 6/2004 |
| WO | WO 2004/052903 | 6/2004 |
| WO | WO 2004/063209 | 7/2004 |
| WO | WO 2004/076470 | 9/2004 |
| WO | WO 2004/080990 A1 | 9/2004 |
| WO | WO 2005/012318 A2 | 2/2005 |
| WO | WO 2005/012326 | 2/2005 |
| WO | WO 2005/085237 | 9/2005 |
| WO | WO 2005/085265 | 9/2005 |
| WO | 2006/011469 A1 | 2/2006 |
| WO | 2006/034489 A2 | 3/2006 |
| WO | 2006/064033 A2 | 6/2006 |
| WO | 2006/089872 A1 | 8/2006 |
| WO | 2006/108842 A1 | 10/2006 |
| WO | 2006/117360 A1 | 11/2006 |
| WO | 2006/120208 A1 | 11/2006 |
| WO | 2007/014894 A2 | 2/2007 |
| WO | 2007/025943 A2 | 3/2007 |
| WO | 2007/028814 A1 | 3/2007 |
| WO | 2007/031548 A2 | 3/2007 |

OTHER PUBLICATIONS

Adachi et al., "T-1095, a Renal Na+-Glucose Transporter Inhibitor, Improves Hyperglycemia in Streptozotocin-Induced Diabetic Rats" Metabolism (2000) vol. 49, No. 8, pp. 990-995.*

Nouri Neamati, et al. "Depsides and Depsidones as Inhibitors of HIV-1 Integrase: Discovery of Novel Inhibitors Through 3D Database Searching", J. Med. Chem., 1997, vol. 40, pp. 942-951.

Herbicidal composition—Abstract of Foreign Patent Document JP58164502.

Abstract of JP2004359630.

International Search Report for corresponding international application PCT/EP2005/002618 mailed Jun. 30, 2005.

Takehiko Iida et al; TributyImagnesium Ate Complex-Mediated Novel Bromine-Magnesium Exchange Reaction for Selective Monosubstitution of Dibromoarenes; Tetrahedron Letters (2001) vol. 42 pp. 4841-4844; Pergamon Press.

Craig A Hutton et al; A Convenient Preparation of dityrosine Via Miyaura Borylation-Suzuki Coupling of Iodotyrosine Derivatives; Tetrahedron Letters (2003) vol. 44 pages 4895-4898; Pergamon Press.

Alois Fuerstner et al; Practical Method for the Rhodium-Catalyzed Addition of Aryl- and Alkenylboronic Acids to Aldehydes; Advanced Synthesis and Catalysis (2001) vol. 343 No. 4 pp. 343-350.

Wolfgang Dohle et al; Copper-Mediated Cross-Coupling of Functionalized Arylmagnesium Reagents with Functionalized Alkyl and Benzylic Halides; Organic Letters (2001) vol. 3 No. 18 pp. 2871-2873.

Sabrina M. Nobre et al; Synthesis of Diarylmethane Derivatives from Pd-Catalyzed Cross-Coupling Reactions of Benzylic Halides with Arylboronic Acids; Tetrahedron Letters (2004) vol. 45 8225-8228.

Mark McLaughlin et al; Suzuki-Miyaura Cross-Coupling of Benzylic Phospahates with Arylboronic Acids; Organic Letters (2005) vol. 7 No. 22 pp. 4875-4878.

Masanori Hatsuda et al; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.

Federica Stazi et al; Statistical Experimental Design-Driven Discovery of room-Temperature Conditions for Palladium-Catalyzed Cyanation of Aryl Bromides; Tetrahedron Letters (2005) vol. 46 1815-1818; Elsevier Ltd.

Ja Seo Koo et al; 2-Pyridyl Cyanate: A Useful Reagent for he Preparation of Nitriles; Synthetic Communications (1996) vol. 26 No. 20 pp. 3709-3713; Marcel Dekker, Inc.

Michael Bech Sommer et al; displacement of Halogen of 2-Halogeno-Substituted Benzonitriles with Carbonions. Preparation of (2-Cyanoaryl)arylacetonitriles; Journal of Organic Chemistry (1990) vol. 55 pp. 4817-4821.

Richard J. Perner et al; 5,6,7-Trisubstituted 4-Aminopyrido[2,3-d]pyrimidines as Novel inhibitors of Adenosime Kinase; Journal of Medicinal Chemistry (2003) vol. 46 pp. 5249-5257.

Debra J. Wallace et al; Cyclopropylboronic Acid: Synthesis and Suzuki Cross-Coupling Reactions; Tetrahedron Letters (2002) vol. 43 pp. 6987-6990; Pergamon Press.

Sandrine Langle et al; Selective Double Suzuki Cross-Coupling Reactions. Synthesis of Unsymmetrical Diaryl (or Heteroaryl) Methanes; Tetrahedron Letters (2003) vol. 44 pp. 9255-9258; Pergamon Press.

International Search Report for PCT/EP2007/051411 mailed on May 2, 2007.

International Search Report for PCT/EP2007/054248 mailed on Jun. 18, 2007.

Rik R. Tykwinski; Evolution in the Palladium-Catalyzed Cross-Coupling of sp- and sp2-Hybridized Carbon Atoms; Angew Chemical International Edition (2003) vol. 42 pp. 1566-1568.

G. Erik Jagdmann, Jr; Synthesis of 5-(4-Substituted Benzyl)-2,4-Diaminoquinazolines as Inhibitors of Candida Albicans Dihydrofolate Reductase; Journal Heterocyclic Chemical (1995) vol. 32 pp. 1461-1465.

International Search Report for PCT/EP2006/061956 mailed on Jul. 5, 2006.

Lasslo Revesz et al; SAR of Benzoylpylpyridines and Benzophenones as p38 Alpha MAP Kinase Inhibitors with Oral Activity; Bioorganic & Medicinal Chemisty Letters (2004) vol. 14 pp. 3601-3605.

International Search Report for PCT/EP2006/062191 mailed Aug. 8, 2006.

International Search Report for PCT/EP2006/066107 mailed Jan. 11, 2007.

International Search Report for PCT/EP2006/066347 mailed Mar. 7, 2007.

Song Xue et al; Zinc-mediated Synthesis of Alpha-C-Glycosided from 1,2-Anhydroglycosides; Synletters (2003) vol. 6 pp. 870-872.

Takeshi Kuribayashi et al; Bis C-Glycosylated Diphenylmethanes for Stable Glycoepitope Mimetics; Syntletters (1999) vol. 6 pp. 737-740.

International Search Report for PCT/EP2005/056806 mailed Dec. 27, 2006.

International Search Report for PCT/EP2006/065710 mailed Mar. 8, 2007.

U.S. Appl. No. 11/674,839, filed Feb. 14, 2007.

U.S. Appl. No. 11/742,612, filed May 1, 2007.

International Search report for PCT/EP2006/061957/ mailed on Jul. 5, 2006.

Non Final Office Action dated Apr. 2, 2008 from U.S. Appl. No. 11/674,839 filed on Feb. 14, 2007.

Non Final Office Action dated Apr. 2, 2008 from U.S. Appl. No. 11/742,612 filed on May 1, 2007.

Tetsuya Adachi, et al; T-1095, A Renal Na+-Glucose Transporter inhibitor, Improves Hyperglycemia in Streptozotocin-Induced Diabetic Rats; Metabolism (2000) vol. 49, No. 8, pp. 990-995.

Akira Oku, et al; T-1095, An Inhibitor or renal $Na^+$-Glucose Cotransporters, May Provide a Novel Approach to Treating Diabetes; Diabetes (1999) vol. 48 pp. 1794-1800.

Takeshi Kuribayashi, et al; c-Glycosylated Aryl tins: Versatile Building Blocks for Aryl C- Glycoside Glycomimetics; J. Carbohydrate Chemistry (1999) vol. 18, No. 4 pp. 371-382.

Takeshi Kuribayashi, et al; C-Glycosylated Diphenylmethanes and Benzophenones: The Stille Coupling Reaction of C-Glycosylated Aryl tins with Benzyl Bromides and Acid Chlorides; J. Carbohydrate Chemistry (1999) vol. 18, No. 4 pp. 393-401.

Kiichiro Ueta, et al; Long-Term Treatment with the $Na^+$-Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.

Non-Final Office Action dated Jun. 24, 2008 from U.S. Appl. No. 11/406,971 filed Apr. 19, 2006.

Non-Final Office Action dated Jun. 5, 2008 from U.S. Appl. No. 11/408,899 filed on Apr. 21, 2006.

Rachida Benhaddou et al; Tetra-n-Propylammonium Tetra-Oxoruthenate(VII): A Reagent of Choice for the Oxidation of Diversely Protected Glycopyranoses and Glycofuranoses to Lactones; Carbohydrate Research (1994) vol. 260 pp. 243-250.

International Search Report for PCT/EP2006/061520 mailed Jul. 26, 2006.

International Search Report for PCT/EP2006/064702 mailed on Jul. 26, 2007.

Notice of Allowance and Fee(s) Due dated Jan. 13, 2009 from U.S. Appl. No. 11/304,284 filed Dec. 15, 2005.

Non-Final Office Action dated May 8, 2008 from U.S. Appl. No. 11/359,846 filed Feb. 22, 2006.

Response dated Nov. 5, 2008 to Non-Final Office Action dated May 8, 2008 from U.S. Appl. No. 11/359,846 filed Feb. 22, 2006.

Notice of Allowance and Fee(s) Due dated Feb. 3, 2009 from U.S. Appl. No. 11/359,846 filed Feb. 22, 2006.

Notice of Allowance and Fee(s) Due dated Dec. 30, 2008 from U.S. Appl. No. 11/674,839 filed Feb. 14, 2007.

Notice of Allowance and Fee(s) Due dated Jan. 2, 2009 from U.S. Appl. No. 11/742,612 filed May 1, 2007.

* cited by examiner

GLUCOPYRANOSYL-SUBSTITUTED PHENYL DERIVATIVES, MEDICAMENTS CONTAINING SUCH COMPOUNDS, THEIR USE AND PROCESS FOR THEIR MANUFACTURE

RELATED APPLICATIONS

This application claims benefit under 35 U.S.C. 119(e) of U.S. provisional application Ser. No. 60/560,239 filed Apr. 7, 2004, from German application number DE102004 012676.3 filed Mar. 16, 2004, from German application number DE102004040168.3 filed Aug. 18, 2004, from German application number DE102004061145.9 filed Dec. 16, 2004, and from European application EP05002628.5, filed Feb. 9, 2005, the contents of which are incorporated herein.

DESCRIPTION OF THE INVENTION

The present invention relates to glucopyranosyl-substituted benzene derivatives of general formula I

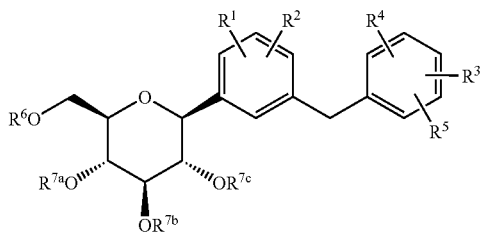

wherein the groups $R^1$ to $R^6$ and $R^{7a}$, $R^{7b}$, $R^{7c}$ are as defined hereinafter, including the tautomers, the stereoisomers, the mixtures thereof and the salts thereof. The invention further relates to pharmaceutical compositions containing a compound of formula I according to the invention as well as the use of a compound according to the invention for preparing a pharmaceutical composition for the treatment of metabolic disorders. In addition, the invention relates to processes for preparing a pharmaceutical composition as well as a compound according to the invention.

In the literature, compounds which have an inhibitory effect on the sodium-dependent glucose cotransporter SGLT2 are proposed for the treatment of diseases, particularly diabetes.

Glucopyranosyloxy-substituted aromatic groups and the preparation thereof and their possible activity as SGLT2 inhibitors are known from published International applications WO 98/31697, WO 01/27128, WO 02/083066, WO 03/099836, WO 2004/063209, WO 2004/080990, WO 2004/013118, WO 2004/052902, WO 2004/052903 and US application U.S. 2003/0114390.

AIM OF THE INVENTION

The aim of the present invention is to find new pyranosyloxy-substituted benzene derivatives, particularly those which are active with regard to the sodium-dependent glucose cotransporter SGLT, particularly SGLT2. A further aim of the present invention is to discover pyranosyloxy-substituted benzene derivatives which have an enhanced inhibitory effect on the sodium-dependent glucose cotransporter SGLT2 in vitro and/or in vivo compared with known, structurally similar compounds and/or have better pharmacological or pharmacokinetic properties.

A further aim of the present invention is to provide new pharmaceutical compositions which are suitable for the prevention and/or treatment of metabolic disorders, particularly diabetes.

The invention also sets out to provide a process for preparing the compounds according to the invention.

Other aims of the present invention will become apparent to the skilled man directly from the foregoing and following remarks.

OBJECT OF THE INVENTION

In a first aspect the present invention relates to glucopyranosyloxy-substituted benzene derivatives of general formula I

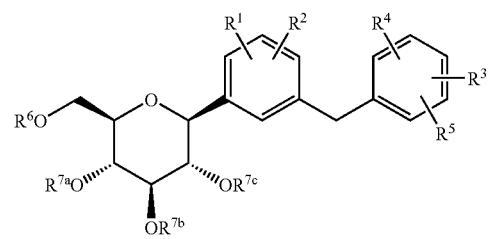

wherein $R^1$ is selected from the definitions of the group A and
  if $R^3$ is selected from the definitions of the group B, $R^1$ may additionally also be selected from the meanings hydrogen, fluorine, chlorine, bromine, iodine, $C_{1-4}$-alkyl, $C_{2-4}$-alkenyl-$C_{1-4}$-alkyl, $C_{2-4}$-alkynyl-$C_{1-4}$-alkyl, $C_{2-4}$-alkenyl-$C_{1-4}$-alkoxy, $C_{2-4}$-alkynyl-$C_{1-4}$-alkoxy, $C_{3-7}$-cycloalkyl-$C_{1-4}$-alkyl, $C_{5-7}$-cycloalkenyl-$C_{1-4}$-alkyl, a methyl group substituted by 1 to 3 fluorine atoms, an ethyl group substituted by 1 to 5 fluorine atoms, $C_{1-4}$-alkoxy, a methoxy group substituted by 1 to 3 fluorine atoms, an ethoxy group substituted by 1 to 5 fluorine atoms, a $C_{1-4}$-alkyl group substituted by a hydroxy or $C_{1-3}$-alkoxy group, a $C_{2-4}$-alkoxy group substituted by a hydroxy or $C_{1-3}$-alkoxy group, $C_{3-6}$-cycloalkyl-$C_{1-3}$-alkoxy or hydroxy, while in the above-mentioned cycloalkyl and cycloalkenyl rings one or two methylene groups may be replaced independently of one another by O or CO, and $R^2$ denotes hydrogen, fluorine, chlorine, bromine, hydroxy, $C_{1-4}$-alkyl, $C_{1-4}$-alkoxy, cyano or nitro, while the alkyl or alkoxy group may be mono- or polysubstituted by fluorine, and $R^3$ is selected from the definitions of the group B and
  if $R^1$ is selected from the definitions of the group A, $R^3$ may additionally also be selected from the meanings hydrogen, fluorine, chlorine, bromine, iodine, $C_{1-6}$-alkyl, $C_{2-4}$-alkenyl-$C_{1-4}$-alkyl, $C_{2-4}$-alkynyl-$C_{1-4}$-alkyl, $C_{2-4}$-alkenyl-$C_{1-4}$-alkoxy, $C_{2-4}$-alkynyl-$C_{1-4}$-alkoxy, $C_{3-7}$-cycloalkyl, $C_{5-7}$-cycloalkenyl, $C_{3-7}$-cycloalkyl-$C_{1-4}$-alkyl, $C_{5-7}$-cycloalkenyl-$C_{1-4}$-alkyl, $C_{3-6}$-cycloalkylidenmethyl, hydroxy, $C_{1-6}$-alkoxy, $C_{3-6}$-cycloalkyl-$C_{1-3}$-alkoxy, aryl, aryl-$C_{1-3}$-alkyl, heteroaryl, heteroaryl-$C_{1-3}$-alkyl, aryloxy, aryl-$C_{1-3}$-alkyl-oxy, a methyl or methoxy group substituted by 1 to 3 fluorine atoms, a $C_{2-4}$-alkyl or $C_{2-4}$-alkoxy group substituted by 1 to 5 fluorine atoms, a $C_{1-4}$-alkyl group substituted by a cyano group, a $C_{1-4}$-alkyl group substituted by a hydroxy or $C_{1-3}$-alkyloxy group, cyano, carboxy, $C_{1-3}$-alkoxycarbonyl, aminocarbonyl, ($C_{1-3}$-alkylamino)carbonyl, di-($C_{1-3}$-alkyl)aminocarbonyl, pyrrolidin-1-ylcarbonyl, piperidin-1-ylcarbonyl, morpholin-4-ylcarbonyl, piperazin-1-yl-carbonyl, 4-($C_{1-3}$-alkyl)-piperazin-1-ylcarbonyl, ($C_{1-4}$-alkyl)carbonylamino, $C_{1-4}$-alkyl-sulphonylamino, $C_{1-4}$-alkylsulphanyl, $C_{1-4}$-alkylsulphinyl, $C_{1-4}$-alkylsulphonyl, arylsulphonylamino, aryl-$C_{1-3}$-alkylsulphonylamino or arylsulphonyl, $R^4$, $R^5$ independently of one another denote hydrogen, fluorine, chlorine, bromine, iodine, cyano, nitro, $C_{1-3}$-alkyl, $C_{1-3}$-alkoxy, methyl or methoxy substituted by 1 to 3 fluorine atoms, A denotes $C_{2-6}$-alkyn-1-yl, $C_{2-6}$-alken-1-yl, $C_{3-7}$-cycloalkyl, $C_{5-7}$-cycloalkenyl, aryl, heteroaryl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, arylamino-carbonyl, heteroarylaminocarbonyl, $C_{1-4}$-alkoxycarbonyl, aryl-$C_{1-3}$-alkoxycarbonyl, heteroaryl-$C_{1-3}$-alkoxycarbonyl, amino, $C_{1-4}$-alkylamino, di-($C_{1-3}$-alkyl)amino, pyrrolidin-1-yl, pyrrolidin-2-on-1-yl, piperidin-1-yl, piperidin-2-on-1-yl, morpholin-4-yl, morpholin-3-on-4-yl, piperazin-1-yl, 4-($C_{1-3}$-alkyl)piperazin-1-yl, $C_{1-4}$-alkylcarbonylamino, arylcarbonylamino, heteroarylcarbonylamino, $C_{3-7}$-cycloalkyloxy, $C_{5-7}$-cycloalkenyloxy, aryloxy, heteroaryloxy, $C_{1-4}$-alkylsulphinyl, $C_{1-4}$-alkylsulphonyl, $C_{3-7}$-cycloalkylsulphanyl, $C_{3-7}$-cycloalkylsulphinyl, $C_{3-7}$-cycloalkylsulphonyl, $C_{5-7}$-cycloalkenylsulphanyl, $C_{5-7}$-cycloalkenylsulphinyl, $C_{5-7}$-cycloalkenylsulphonyl, arylsulphanyl, arylsulphinyl, arylsulphonyl, heteroarylsulphanyl, heteroarylsulphinyl, heteroarylsulphonyl, cyano or nitro, while the above-mentioned alkynyl and alkenyl groups may be mono- or polysubstituted by fluorine or chlorine, and the above-mentioned alkynyl and alkenyl groups may be mono- or disubstituted by identical or different groups L1, and the above-mentioned cycloalkyl and cycloalkenylrings independently of one another may be mono- or disubstituted by substituents selected from fluorine and $C_{1-3}$-alkyl, and in the above-mentioned cycloalkyl and cycloalkenyl rings one or two methylene groups may be replaced independently of one another by O, S, CO, SO, $SO_2$ or $NR^N$, B denotes tri-($C_4$-alkyl)silyl-$C_{1-6}$-alkyl, $C_{2-6}$-alkyn-1-yl, $C_{2-6}$-alken-1-yl, amino, $C_{1-3}$-alkylamino, di-($C_{1-3}$-alkyl)amino, pyrrolidin-1-yl, pyrrolidin-2-on-1-yl, piperidin-1-yl, piperidin-2-on-1-yl, morpholin-4-yl, morpholin-3-on-4-yl, piperazin-1-yl, 4-($C_{1-3}$-alkyl)piperazin-1-yl, arylcarbonylamino, heteroarylcarbonylamino, nitro, $C_{3-10}$-cycloalkyloxy, $C_{5-10}$-cycloalkenyloxy, $C_{3-10}$-cycloalkylsulphanyl, $C_{3-10}$-cycloalkylsulphinyl, $C_{3-10}$-cycloalkylsulphonyl, $C_{5-10}$-cycloalkenylsulphanyl, $C_{5-10}$-cycloalkenylsulphinyl, $C_{5-10}$-cycloalkenyl-sulphonyl, arylsulphanyl, arylsulphinyl, heteroarylsulphanyl or heteroarylsulphinyl, while the above-mentioned alkynyl and alkenyl groups may be mono- or polysubstituted by fluorine or chlorine, and the above-mentioned alkynyl and alkenyl groups may be mono- or disubstituted by identical or different groups L1;

while the above-mentioned cycloalkyl and cycloalkenyl rings may be mono- or disubstituted independently of one another by substituents selected from fluorine and $C_{1-3}$-alkyl, and in the above-mentioned cycloalkyl and cycloalkenyl rings one or two methylene groups may be replaced independently of one another by O, S, CO, SO, $SO_2$ or $NR^N$, $R^N$ denotes H, $C_{1-4}$-alkyl, $C_{1-4}$-alkylcarbonyl or $C_{1-4}$-alkylsulphonyl, L1 independently of one another are selected from among hydroxy, cyano, nitro, $C_{3-7}$-cycloalkyl, aryl, heteroaryl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)-aminocarbonyl, pyrrolidin-1-ylcarbonyl, piperidin-1-ylcarbonyl, morpholin-4-ylcarbonyl, arylaminocarbonyl, heteroarylaminocarbonyl, $C_{1-4}$-alkoxycarbonyl, aryl-$C_{1-3}$-alkoxycarbonyl, heteroaryl-$C_{1-3}$-alkoxycarbonyl, $C_{1-4}$-alkyloxy, aryloxy, heteroaryloxy, $C_{1-4}$-alkylsulphanyl, arylsulphanyl, heteroarylsulphanyl, $C_{1-4}$-alkylsulphinyl, arylsulphinyl, heteroarylsulphinyl, $C_{1-4}$-alkylsulphonyl, arylsulphonyl and heteroarylsulphonyl; and L2 independently of one another are selected from among fluorine, chlorine, bromine, iodine, $C_{1-3}$-alkyl, difluoromethyl, trifluoromethyl, $C_{1-3}$-alkoxy, difluoromethoxy, trifluoromethoxy and cyano; and $R^6$, $R^{7a}$, $R^{7b}$, $R^{7c}$ independently of one another have a meaning selected from among hydrogen, ($C_{1-18}$-alkyl)carbonyl, ($C_{1-8}$-alkyl)oxycarbonyl, arylcarbonyl and aryl-($C_{1-3}$-alkyl)-carbonyl, while by the aryl groups mentioned in the definition of the above groups are meant phenyl or naphthyl groups which may be mono- or disubstituted independently of one another by identical or different groups L2; and by the heteroaryl groups mentioned in the definition of the above groups are meant a pyrrolyl, furanyl, thienyl, pyridyl, indolyl, benzofuranyl, benzothiophenyl, quinolinyl, isoquinolinyl or tetrazolyl group, or is meant a pyrrolyl, furanyl, thienyl or pyridyl group, wherein one or two methyne groups are replaced by nitrogen atoms, or is meant an indolyl, benzofuranyl, benzothiophenyl, quinolinyl or isoquinolinyl group, wherein one to three methyne groups are replaced by nitrogen atoms, while the above-mentioned heteroaryl groups independently of one another may be mono- or disubstituted by identical or different groups L2;

while, unless otherwise stated, the above-mentioned alkyl groups may be straight-chain or branched, the tautomers, the stereoisomers thereof, the mixtures thereof and the salts thereof.

The compounds of general formula I according to the invention and the physiologically acceptable salts thereof have valuable pharmacological properties, particularly an inhibitory effect on the sodium-dependent glucose cotransporter SGLT, particularly SGLT2. Moreover compounds according to the invention may have an inhibitory effect on the sodium-dependent glucose cotransporter SGLT1. Compared with a possible inhibitory effect on SGLT1 the compounds according to the invention preferably inhibit SGLT2 selectively.

The present invention also relates to the physiologically acceptable salts of the compounds according to the invention with inorganic or organic acids.

This invention also relates to pharmaceutical compositions, containing at least one compound according to the invention or a physiologically acceptable salt according to the invention, optionally together with one or more inert carriers and/or diluents.

This invention also relates to the use of at least one compound according to the invention or one of the physiologically acceptable salts thereof for preparing a pharmaceutical composition which is suitable for the treatment or prevention or diseases or conditions which can be influenced by inhibiting the sodium-dependent glucose cotransporter SGLT, particularly SGLT2.

This invention also relates to the use of at least one compound according to the invention or one of the physiologically acceptable salts thereof for preparing a pharmaceutical composition which is suitable for the treatment of metabolic disorders.

This invention also relates to the use of at least one compound according to the invention or one of the physiologically acceptable salts thereof for preparing a pharmaceutical composition for inhibiting the sodium-dependent glucose cotransporter SGLT, particularly SGLT2.

The invention further relates to a process for preparing a pharmaceutical composition according to the invention, characterised in that a compound according to the invention or one of the physiologically acceptable salts thereof is incorporated in one or more inert carriers and/or diluents by a non-chemical method.

The present invention also relates to a process for preparing the compounds of general formula I according to the invention, characterised in that a) in order to prepare compounds of general formula I which are defined as hereinbefore and hereinafter, a compound of general formula II

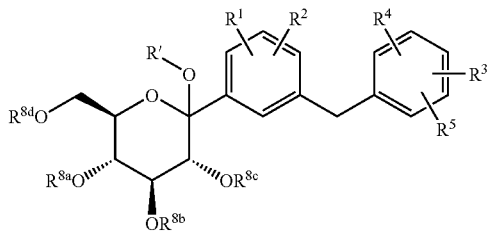

wherein
R' denotes H, $C_{1-4}$-alkyl, ($C_{1-18}$-alkyl)carbonyl, ($C_{1-18}$-alkyl)oxycarbonyl, arylcarbonyl and aryl-($C_{1-3}$-alkyl)-carbonyl, wherein the alkyl or aryl groups may be mono- or polysubstituted by halogen;
$R^{8a}$, $R^{8b}$,
$R^{8c}$, $R^{8d}$ independently of one another have one of the meanings given hereinbefore and hereinafter for the groups $R^6$, $R^{7a}$, $R^{7b}$, $R^{7c}$, denote a benzyl group or a $R^aR^bR^c$Si group or a ketal or acetal group, particularly an alkylidene or arylalkylidene ketal or acetal group, while in each case two adjacent groups $R^{8a}$, $R^{8b}$, $R^{8c}$, $R^{8d}$ may form a cyclic ketal or acetal group or a 1,2-di($C_{1-3}$-alkoxy)-1,2-di($C_{1-3}$-alkyl)-ethylene bridge, while the above-mentioned ethylene bridge forms, together with two oxygen atoms and the two associated carbon atoms of the pyranose ring, a substituted dioxane ring, particularly a 2,3-dimethyl-2,3-di($C_{1-3}$-alkoxy)-1,4-dioxane ring, and alkyl, aryl and/or benzyl groups may be mono- or polysubstituted by halogen or $C_{1-3}$-alkoxy and benzyl groups may also be substituted by a di-($C_{1-3}$-alkyl)amino group; and $R^a$, $R^b$, $R^c$ independently of one another denote $C_{1-4}$-alkyl, aryl or aryl-$C_{1-3}$-alkyl, wherein the aryl or alkyl groups may be mono- or polysubstituted by halogen;
while by the aryl groups mentioned in the definition of the above groups are meant phenyl or naphthyl groups, preferably phenyl groups;
and wherein the groups $R^1$ to $R^5$ and $R^6$, $R^{7a}$, $R^{7b}$, $R^{7c}$ are defined as hereinbefore and hereinafter;
is reacted with a reducing agent in the presence of a Lewis or Brønsted acid, while the any protective groups present are cleaved simultaneously or subsequently; or b) in order to prepare compounds of general formula I wherein $R^6$, $R^{7a}$, $R^{7b}$ and $R^{7c}$ denote hydrogen, a compound of general formula III

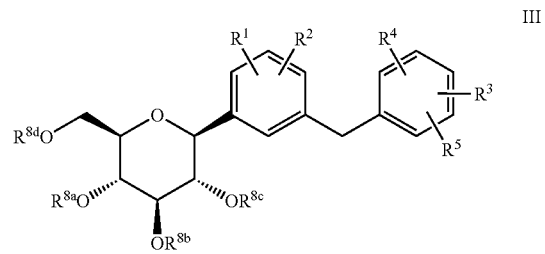

wherein $R^{8a}$, $R^{8b}$, $R^{8c}$, $R^{8d}$ and $R^1$ to $R^5$ are defined as hereinbefore and hereinafter, but at least one of the groups $R^{8a}$, $R^{8b}$, $R^{8c}$, $R^{8d}$ does not denote hydrogen, is hydrolysed, and if desired a compound of general formula I thus obtained wherein $R^6$ denotes a hydrogen atom, is converted by acylation into a corresponding acyl compound of general formula I, and/or if necessary any protective group used in the reactions described above is cleaved and/or if desired a compound of general formula I thus obtained is resolved into its stereoisomers and/or if desired a compound of general formula I thus obtained is converted into the salts thereof, particularly for pharmaceutical use into the physiologically acceptable salts thereof.

This invention further relates to a process for preparing compounds of general formula II

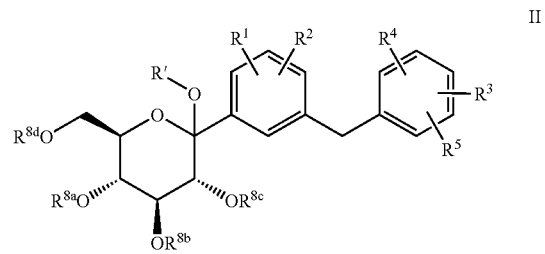

wherein
R' denotes H, $C_{1-4}$-alkyl, ($C_{1-8}$-alkyl)carbonyl, ($C_{1-8}$-alkyl)oxycarbonyl, arylcarbonyl and aryl-($C_{1-3}$-alkyl)-carbonyl, wherein the alkyl or aryl groups may be mono- or polysubstituted by halogen;
$R^{8a}$, $R^{8b}$,
$R^{8c}$, $R^{8d}$ independently of one another has one of the meanings given for the groups $R^6$, $R^{7a}$, $R^{7b}$, $R^{7c}$, denote a benzyl group or a $R^aR^bR^cSi$ group or a ketal or acetal group, while in each case two adjacent groups $R^{8a}$, $R^{8b}$, $R^{8c}$, $R^{8d}$ may form a cyclic ketal or acetal group or may form, with two oxygen atoms of the pyranose ring, a substituted 2,3-oxydioxane ring, particularly a 2,3-dimethyl-2,3-di($C_{1-3}$-alkoxy)-1,4-dioxane ring, and alkyl, aryl and/or benzyl groups may be mono- or polysubstituted by halogen or $C_{1-3}$-alkoxy and benzyl groups may also be substituted by a di-($C_{1-3}$-alkyl)amino group; and $R^a$, $R^b$, $R^c$ independently of one another denote $C_{1-4}$-alkyl, aryl or aryl-$C_{1-3}$-alkyl, while the alkyl or aryl groups may be mono- or polysubstituted by halogen;

while by the aryl groups mentioned in the definition of the above groups are meant phenyl or naphthyl groups, preferably phenyl groups;

and $R^1$ to $R^5$, $R^6$, $R^{7a}$, $R^{7b}$, $R^{7c}$ are defined as hereinbefore and hereinafter, wherein an organometallic compound (V) which may be obtained by halogen-metal exchange or by inserting a metal in the carbon-halogen bond of a halogen-benzylbenzene compound of general formula IV

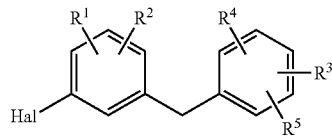

IV wherein Hal denotes Cl, Br and I and $R^1$ to $R^5$ are defined as hereinbefore and hereinafter, and optionally subsequent transmetallation, is added to a gluconolactone of general formula VI

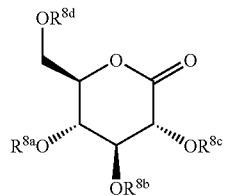

VI wherein $R^{8a}$, $R^{8b}$, $R^{8c}$, $R^{8d}$ are defined as hereinbefore and hereinafter, and then the resulting adduct, is reacted, preferably in situ, with water or an alcohol R'—OH, while R' denotes optionally substituted $C_{1-4}$-alkyl, in the presence of an acid, such as for example methanesulphonic acid, sulphuric acid, hydrochloric acid, acetic acid or ammonium chloride, and optionally the product obtained in the reaction with water wherein R' denotes H is converted, in a subsequent reaction, with an acylating agent, such as for example the corresponding acid chloride or anhydride, into the product of formula II wherein R' denotes ($C_{1-18}$-alkyl)carbonyl, ($C_{1-18}$-alkyl)oxycarbonyl, arylcarbonyl or aryl-($C_{1-3}$-alkyl)-carbonyl, which may be substituted as specified.

The intermediate products listed, particularly those of formula IV, formula II and formula III, are also a subject of this invention.

DETAILED DESCRIPTION OF THE INVENTION

Unless otherwise stated, the groups, residues and substituents, particularly $R^1$ to $R^5$, A, B, L1, L2, $R^N$, $R^6$, $R^{7a}$, $R^{7b}$, $R^{7c}$, $R^{8a}$, $R^{8b}$, $R^{8c}$, $R^{8d}$, are defined as above and hereinafter.

If residues, substituents or groups occur several times in a compound, they may have the same or different meanings.

According to the invention preferred glucopyranosyl-substituted benzene derivatives are those of general formula I

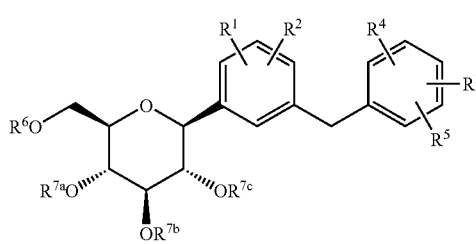

I wherein $R^1$ is selected from the definitions of the group A and
if $R^3$ is selected from the definitions of the group B, $R^1$ may additionally also be selected from the meanings hydrogen, fluorine, chlorine, bromine, iodine, $C_{1-4}$-alkyl, $C_{2-4}$-alkenyl-$C_{1-4}$-alkyl, $C_{2-4}$-alkynyl-$C_{1-4}$-alkyl, $C_{3-7}$-cycloalkyl-$C_{1-4}$-alkyl, $C_{5-7}$-cycloalkenyl-$C_{1-4}$-alkyl, a methyl group substituted by 1 to 3 fluorine atoms, an ethyl group substituted by 1 to 5 fluorine atoms, $C_{1-4}$-alkoxy, a methoxy group substituted by 1 to 3 fluorine atoms, an ethoxy group substituted by 1 to 5 fluorine atoms, a $C_{1-4}$-alkyl group substituted by a hydroxy or $C_{1-3}$-alkoxy group, a $C_{2-4}$-alkoxy group substituted by a hydroxy or $C_{1-3}$-alkoxy group, $C_{3-6}$-cycloalkyl-$C_{1-3}$-alkoxy or hydroxy, while in the above-mentioned cycloalkyl and cycloalkenyl rings one or two methylene groups may be replaced independently of one another by O or CO, and $R^2$ denotes hydrogen, fluorine, chlorine, bromine, hydroxy, $C_{1-4}$-alkyl, $C_{1-4}$-alkoxy, cyano or nitro, while the alkyl or alkoxy group may be mono- or polysubstituted by fluorine, and $R^3$ is selected from the definitions of the group B and
if $R^1$ is selected from the definitions of the group A, $R^3$ may additionally also be selected from the meanings hydrogen, fluorine, chlorine, bromine, iodine, $C_{1-6}$alkyl, $C_{2-4}$-alkenyl-$C_{1-4}$-alkyl, $C_{2-4}$-alkynyl-$C_{1-4}$-alkyl, $C_{3-7}$-cycloalkyl, $C_{5-7}$-cycloalkenyl, $C_{3-7}$-cycloalkyl-$C_{1-4}$-alkyl, $C_{5-7}$-cycloalkenyl-$C_{1-4}$-alkyl, $C_{3-6}$-cycloalkylidenemethyl, hydroxy, $C_{1-6}$-alkoxy, $C_{3-6}$-cycloalkyl-$C_{1-3}$-alkoxy, aryl, aryl-$C_{1-3}$-alkyl, heteroaryl, heteroaryl-$C_{1-3}$-alkyl, aryloxy, aryl-$C_{1-3}$-alkyl-oxy, a methyl or methoxy group substituted by 1 to 3 fluorine atoms, a $C_{2-4}$-alkyl or $C_{2-4}$-alkoxy group substituted by 1 to 5 fluorine atoms, a $C_{1-4}$-alkyl group substituted by a cyano group, a $C_{1-4}$-alkyl group substituted by a hydroxy or $C_{1-3}$-alkyloxy group, cyano, carboxy, $C_{1-3}$-alkoxycarbonyl, aminocarbonyl, ($C_{1-3}$-alkylamino)carbonyl, di-($C_{1-3}$-alkyl)aminocarbonyl, pyrrolidin-1-ylcarbonyl, piperidin-1-ylcarbonyl, morpholin-4-ylcarbonyl, piperazin-1-yl-carbonyl, 4-($C_{1-3}$-alkyl)-piperazin-1-ylcarbonyl, ($C_{1-4}$-alkyl)carbonylamino, $C_{1-4}$-alkyl-sulphonylamino, $C_{1-4}$-alkylsulphanyl, $C_{1-4}$-alkylsulphinyl, $C_{1-4}$-alkylsulphonyl, arylsulphonylamino, aryl-$C_{1-3}$-alkylsulphonylamino or arylsulphonyl, $R^4$, $R^5$ independently of one another denote hydrogen, fluorine, chlorine, bromine, iodine, cyano, nitro, $C_{1-3}$-alkyl, $C_{1-3}$-alkoxy, methyl or methoxy substituted by 1 to 3 fluorine atoms, A denotes $C_{2-6}$-alkyn-1-yl, $C_{2-6}$-alken-1-yl, $C_{3-7}$-cycloalkyl, $C_{5-7}$-cycloalkenyl, aryl, heteroaryl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, arylaminocarbonyl, heteroarylaminocarbonyl, $C_{1-4}$-alkoxycarbonyl, aryl-$C_{1-3}$-alkoxycarbonyl, heteroaryl-$C_{1-3}$-alkoxycarbonyl, amino, $C_{1-4}$-alkylamino, di-($C_{1-3}$-alkyl)amino, pyrrolidin-1-yl, pyrrolidin-2-on-1-yl, piperidin-1-yl, piperidin-2-on-1-yl, morpholin-4-yl, morpholin-3-on-4-yl, piperazin-1-yl, 4-($C_{1-3}$-alkyl)-piperazin-1-yl, $C_{1-4}$-alkylcarbonylamino, arylcarbonylamino, heteroarylcarbonylamino, $C_{3-7}$-cycloalkyloxy, $C_{5-7}$-cycloalkenyloxy, aryloxy, heteroaryloxy, $C_{1-4}$-alkylsulphinyl, $C_{1-4}$-alkylsulphonyl, $C_{3-7}$-cycloalkylsulphanyl, $C_{3-7}$-cycloalkylsulphinyl, $C_{3-7}$-cycloalkylsulphonyl, $C_{5-7}$-cycloalkenylsulphanyl, $C_{5-7}$-cycloalkenylsulphinyl, $C_{5-7}$-cycloalkenylsulphonyl, arylsulphanyl, arylsulphinyl, arylsulphonyl, heteroarylsulphanyl, heteroarylsulphinyl, heteroarylsulphonyl, cyano or nitro, while the above-mentioned alkynyl- and alkenyl groups may be mono- or polysubstituted by fluorine or chlorine, and while the above-mentioned alkynyl and alkenyl groups may be mono- or disubstituted by identical or different groups L1, and the above-mentioned cycloalkyl and cycloalkenyl rings may be mono- or disubstituted independently of one another by substituents selected from fluorine and $C_{1-3}$-alkyl, and in the above-mentioned cycloalkyl and cycloalkenyl rings one or two methylene groups may be replaced independently of one another by O, S, CO, SO, $SO_2$ or $NR^N$, B denotes tri-($C_{1-4}$-alkyl)silyl-$C_{1-6}$-alkyl, $C_{2-6}$-alkyn-1-yl, $C_{2-6}$-alken-1-yl, amino, $C_{1-3}$-alkylamino, di-($C_{1-3}$-alkyl)amino, pyrrolidin-1-yl, pyrrolidin-2-on-1-yl, piperidin-1-yl, piperidin-2-on-1-yl, morpholin-4-yl, morpholin-3-on-4-yl, piperazin-1-yl, 4-($C_{1-3}$-alkyl)piperazin-1-yl, arylcarbonylamino, heteroarylcarbonylamino, nitro, $C_{3-7}$-cycloalkyloxy, $C_{5-7}$-cycloalkenyloxy, $C_{3-7}$-cycloalkylsulphanyl, $C_{3-7}$-cycloalkylsulphinyl, $C_{3-7}$-cycloalkylsulphonyl, $C_{5-7}$-cycloalkenylsulphanyl, $C_{5-7}$-cycloalkenylsulphinyl, $C_{5-7}$-cycloalkenylsulphonyl, arylsulphanyl, arylsulphinyl, heteroarylsulphanyl or heteroarylsulphinyl, while the above-mentioned alkynyl and alkenyl groups may be mono- or polysubstituted by fluorine or chlorine, and the above-mentioned alkynyl and alkenyl groups may be mono- or disubstituted by identical or different groups L1;

the above-mentioned cycloalkyl and cycloalkenyl rings may be mono- or disubstituted independently of one another by substituents selected from fluorine and $C_{1-3}$-alkyl, and in the above-mentioned cycloalkyl and cycloalkenyl rings one or two methylene groups may be replaced independently of one another by O, S, CO, SO, $SO_2$ or $NR^N$, $R^N$ denotes H or $C_{1-4}$-alkyl, L1 independently of one another are selected from among cyano, nitro, aryl, heteroaryl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, arylaminocarbonyl, heteroarylaminocarbonyl, $C_{1-4}$-alkoxycarbonyl, aryl-$C_{1-3}$-alkoxycarbonyl, heteroaryl-$C_{1-3}$-alkoxycarbonyl, $C_{1-4}$-alkyloxy, aryloxy, heteroaryloxy, $C_{1-4}$-alkylsulphanyl, arylsulphanyl, heteroarylsulphanyl, $C_{1-4}$-alkylsulphinyl, arylsulphinyl, heteroarylsulphinyl, $C_{1-4}$-alkylsulphonyl, arylsulphonyl and heteroarylsulphonyl; and L2 independently of one another are selected from among fluorine, chlorine, bromine, iodine, $C_{1-3}$-alkyl, difluoromethyl, trifluoromethyl, $C_{1-3}$-alkoxy, difluoromethoxy, trifluoromethoxy and cyano; and $R^6$, $R^{7a}$, $R^{7b}$, $R^{7c}$ independently of one another have a meaning selected from among hydrogen, ($C_{1-8}$-alkyl)carbonyl, ($C_{1-8}$-alkyl)oxycarbonyl, arylcarbonyl and aryl-($C_{1-3}$-alkyl)-carbonyl, while by the aryl groups mentioned in the definition of the above groups are meant phenyl or naphthyl groups, which may be mono- or disubstituted independently of one another by identical or different groups L2; and by the heteroaryl groups mentioned in the definition of the above groups are meant a pyrrolyl, furanyl, thienyl, pyridyl, indolyl, benzofuranyl, benzothiophenyl, quinolinyl or isoquinolinyl group, or is meant a pyrrolyl, furanyl, thienyl or pyridyl group, wherein one or two methyne groups are replaced by nitrogen atoms, or is meant an indolyl, benzofuranyl, benzothiophenyl, quinolinyl or isoquinolinyl group, wherein one to three methyne groups are replaced by nitrogen atoms, while the above-mentioned heteroaryl groups may be mono- or disubstituted independently of one another by identical or different groups L2;

while, unless otherwise stated, the above-mentioned alkyl groups may be straight-chain or branched, the tautomers, the stereoisomers thereof, the mixtures thereof and the salts thereof.

Some preferred meanings of individual groups and substituents of the compounds according to the invention will be given hereinafter.

The group $R^3$ is preferably in the meta or para position to the —$CH_2$ bridge, so that compounds according to the following formulae I.1 and I.2, particularly formula I.2, are preferred:

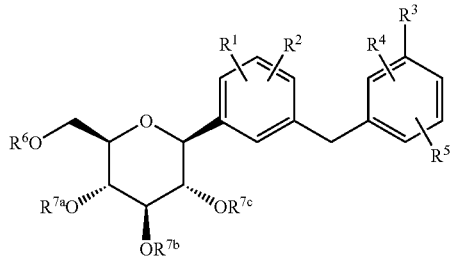

I.1

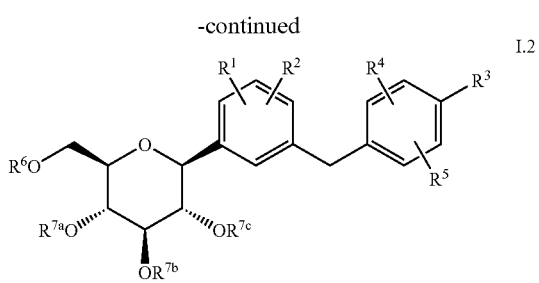

I.2

The term aryl appearing in the groups L1, $R^1$, $R^3$, A and B preferably denotes phenyl.

The term heteroaryl occurring in the groups L1, $R^1$, $R^3$, A and B preferably denotes pyridinyl, pyrimidinyl, pyridazinyl, pyrazinyl, triazinyl, imidazolyl, pyrazolyl, triazolyl, tetrazolyl, oxazolyl, oxadiazolyl, thiazolyl or thiadiazolyl.

The group A preferably denotes $C_{2-4}$-alkyn-1-yl, $C_{2-6}$-alken-1-yl, $C_{3-7}$-cycloalkyl, $C_{5-7}$-cycloalkenyl, $C_{1-4}$-alkylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, $C_{1-4}$-alkoxycarbonyl, amino, $C_{1-4}$-alkylamino, di-($C_{1-3}$-alkyl)amino, pyrrolidin-1-yl, pyrrolidin-2-on-1-yl, piperidin-1-yl, piperidin-2-on-1-yl, morpholin-4-yl, morpholin-3-on-4-yl, piperazin-1-yl, 4-($C_{1-3}$-alkyl)piperazin-1-yl, $C_{1-4}$-alkylcarbonylamino, $C_{3-7}$-cycloalkyloxy, $C_{5-7}$-cycloalkenyloxy, $C_{1-4}$-alkylsulphinyl, $C_{1-4}$-alkylsulphonyl, $C_{3-7}$-cycloalkylsulphanyl, $C_{3-7}$-cycloalkylsulphinyl, $C_{3-7}$-cycloalkylsulphonyl, $C_{5-7}$-cyclo-alkenylsulphanyl, $C_{5-7}$-cycloalkenylsulphinyl, $C_{5-7}$-cycloalkenylsulphonyl, cyano and nitro, while the above-mentioned alkynyl and alkenyl groups may be mono- or polysubstituted by fluorine or chlorine, preferably fluorine, and the above-mentioned alkynyl and alkenyl groups may be mono- or disubstituted by identical or different groups L1, and the above-mentioned cycloalkyl and cycloalkenyl rings may be mono- or disubstituted independently of one another by substituents selected from fluorine and $C_{1-3}$-alkyl, and in the above-mentioned cycloalkyl and cycloalkenyl rings one or two methylene groups may be replaced independently of one another by O, S, CO, SO, $SO_2$ or $NR^N$, preferably O or CO, most particularly preferably by O.

Particularly preferably, the group A denotes $C_{2-6}$-alkyn-1-yl, $C_{2-6}$-alken-1-yl, $C_{3-7}$-cycloalkyl, $C_{5-7}$-cycloalkenyl, $C_{3-7}$-cycloalkyloxy, $C_{5-7}$-cycloalkenyloxy, $C_{1-4}$-alkylsulphinyl, $C_{1-4}$-alkylsulphonyl, $C_{3-7}$-cycloalkylsulphanyl, $C_{3-7}$-cycloalkylsulphinyl, $C_{3-7}$-cycloalkylsulphonyl, $C_{5-7}$-cycloalkenylsulphanyl, $C_{5-7}$-cycloalkenylsulphinyl, $C_{5-7}$-cycloalkenylsulphonyl, cyano and nitro, while the above-mentioned alkynyl and alkenyl groups may be mono- or polysubstituted by fluorine or chlorine, preferably fluorine, and the above-mentioned alkynyl and alkenyl groups may be mono- or disubstituted by identical or different groups L1, and the above-mentioned cycloalkyl and cycloalkenyl rings may be mono- or disubstituted independently of one another by substituents selected from fluorine and $C_{1-3}$-alkyl, and in the above-mentioned $C_{5-6}$-cycloalkyl rings a methylene group may be replaced by O.

Most particularly preferably, the group A denotes $C_{2-6}$-alkyn-1-yl, $C_{2-6}$-alken-1-yl, $C_{3-7}$-cycloalkyl, $C_{3-7}$-cycloalkyloxy, cyano, while in $C_{5-6}$-cycloalkyl groups a methylene unit may be replaced by O.

Examples of the most particularly preferred definitions of the group A are ethynyl, prop-1-yn-1-yl, but-1-yn-1-yl, cyano, cyclopropyloxy, cyclobutyloxy, cyclopentyloxy, cyclohexyloxy.

The group B preferably denotes tri-($C_{1-4}$-alkyl)silyl-$C_{1-6}$-alkyl, $C_{2-6}$-alkyn-1-yl, $C_{2-6}$-alken-1-yl, amino, $C_{1-3}$-alkylamino, di-($C_{1-3}$-alkyl)amino, pyrrolidin-1-yl, pyrrolidin-2-on-1-yl, piperidin-1-yl, piperidin-2-on-1-yl, morpholin-4-yl, morpholin-3-on-4-yl, piperazin-1-yl, 4-($C_{1-3}$-alkyl)piperazin-1-yl, nitro, $C_{3-7}$-cycloalkyloxy, $C_{5-7}$-cycloalkenyloxy, $C_{3-7}$-cycloalkylsulphanyl, $C_{3-7}$-cycloalkylsulphinyl, $C_{3-7}$-cycloalkylsulphonyl, $C_{5-7}$-cycloalkenylsulphanyl, $C_{5-7}$-cycloalkenylsulphinyl, $C_{5-7}$-cycloalkenylsulphonyl, while the above-mentioned alkynyl and alkenyl groups may be mono- or polysubstituted by fluorine or chlorine, preferably fluorine, and the above-mentioned alkynyl and alkenyl groups may be mono- or disubstituted by identical or different groups L1;

the above-mentioned cycloalkyl and cycloalkenyl rings may be mono- or disubstituted independently of one another by substituents selected from fluorine and $C_{1-3}$-alkyl, and in the above-mentioned cycloalkyl and cycloalkenyl rings one or two methylene groups may be replaced independently of one another by O, S, CO, SO, $SO_2$ or $NR^N$, preferably O, CO, S, $SO_2$ or $NR^N$, most particularly preferably by O or CO.

Particularly preferably the group B denotes tri-($C_{1-4}$-alkyl)silyl-$C_{1-6}$-alkyl, $C_{2-6}$-alkyn-1-yl, $C_{2-6}$-alken-1-yl, nitro, $C_{3-7}$-cycloalkyloxy, $C_{5-7}$-cycloalkenyloxy, $C_{3-7}$-cycloalkylsulphanyl, $C_{3-7}$-cycloalkylsulphinyl, $C_{3-7}$-cycloalkylsulphonyl, $C_{5-7}$-cycloalkenylsulphanyl, $C_{5-7}$-cycloalkenylsulphinyl, $C_{5-7}$-cycloalkenylsulphonyl, while the above-mentioned alkynyl and alkenyl groups may be mono- or polysubstituted by fluorine or chlorine, preferably fluorine, and the above-m entioned alkynyl and alkenyl groups may be mono- or disubstituted by identical or different groups L1;

while the above-mentioned cycloalkyl and cycloalkenyl rings may be mono- or disubstituted independently of one another by substituents selected from fluorine and $C_{1-3}$-alkyl, and in the above-mentioned cycloalkyl and cycloalkenyl rings one or two methylene groups may be replaced independently of one another by O, S, CO, SO, $SO_2$ or $NR^N$, preferably O, CO, S, $SO_2$ or $NR^N$, most particularly preferably by O or CO.

Most particularly preferably the group B denotes tri-($C_{1-4}$-alkyl)silyl-$C_{1-6}$-alkyl, $C_{2-6}$-alkyn-1-yl, $C_{2-6}$-alken-1-yl, $C_{3-7}$-cycloalkyloxy, $C_{5-7}$-cycloalkenyloxy, $C_{3-7}$-cycloalkylsulphanyl, $C_{5-7}$-cycloalkenylsulphanyl, while the above-mentioned alkynyl and alkenyl groups may be mono- or polysubstituted by fluorine or monosubstituted by chlorine or the group L1, and in the cycloalkyl and cycloalkenyl groups one or two methylene groups may be replaced independently of one another by O, CO, S, $SO_2$ or $NR^N$, particularly O or CO.

Examples of most particularly preferred definitions of the group B are trimethylsilylethyl, ethynyl, 1-propyn-1-yl, 1-butyn-1-yl, tert.-butylethynyl, 2-hydroxyprop-2-ylethynyl, 2-methoxyprop-2-ylethynyl, 3-hydroxy-1-propyn-1-yl, 3-methoxy-1-propyn-1-yl, ethenyl, 1-propenyl, 1-butenyl, tert.-butylethenyl, cyclopropyloxy, cyclobutyloxy, cyclopentyloxy, cyclohexyloxy, tetrahydrofuranyloxy, tetrahydrothiophenyloxy, 1,1-dioxotetrahydrothiophenyloxy, tetrahydropyranyloxy, tetrahydrothiopyranyloxy, 1,1-dioxotetrahydrothiopyranyloxy, tetrahydrofuranonyloxy, piperidinyloxy, piperidinonyloxy, pyrrolidin-3-yloxy, pyrrolidinon-3-yloxy, tetrahydrofuranyl-sulphanyl, cyclopropyl-sulphanyl, cyclobutylsulphanyl, cyclopentyl-sulphanyl and cyclohexylsulphanyl, while the —NH group in a piperidinyl, piperidinonyl, pyrrolidinyl or pyrrolidinonyl ring may be substituted by $R^N$, particularly $C_{1-3}$-alkyl or acetyl.

Most particularly preferred meanings are trimethylsilyl-ethyl, ethynyl, 2-hydroxyprop-2-ylethynyl, 2-methoxyprop-2-ylethynyl, 3-hydroxy-1-propyn-1-yl, 3-methoxy-1-propyn-1-yl, cyclopropyloxy, cyclobutyloxy, cyclopentyloxy, cyclohexyloxy, tetrahydrofuran-3-yloxy, tetrahydropyran-4-yloxy, piperidin-4-yloxy, N-methylpiperidin-4-yloxy and N-acetylpiperidin-4-yloxy. Examples which deserve special mention are ethynyl, trimethylsilylethyl, cyclobutyloxy, cyclopentyloxy, cyclohexyloxy, tetrahydrofuran-3-yloxy and tetrahydropyran-4-yloxy.

If in the residues or groups A, B, $R^1$ or $R^3$ there are cycloalkyl or cycloalkenyl rings wherein two methylene groups are replaced by O, S or $NR^N$ or are replaced by S, $NR^N$, CO, SO or $SO_2$, these methylene groups are preferably not directly connected to one another. If however two methylene groups are replaced by O and CO or by $NR^N$ and CO, these may be directly connected to one another, so as to form a —O—CO— or —$NR^N$—CO group.

Preferred meanings of the group L1 are selected from among hydroxy, cyano, $C_{3-6}$-cycloalkyl, $C_{1-4}$-alkylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, $C_{1-4}$-alkoxycarbonyl, $C_{1-4}$-alkyloxy, $C_{1-4}$-alkylsulphanyl, $C_{1-4}$-alkylsulphinyl, and $C_{1-4}$-alkylsulphonyl.

Particularly preferred meanings of the group L1 are selected from among hydroxy, $C_{1-4}$-alkyloxy and $C_{1-4}$-alkylsulphanyl.

If L1 denotes hydroxy, the hydroxy group is not directly linked to a C atom of a double or triple bond.

Compounds according to a first embodiment of this invention may be described by general formula I, particularly formulae I.1 and I.2, particularly preferably formula I.2, wherein $R^3$ is selected from one of the definitions of the group B given hereinbefore and
the other groups and substituents are defined as hereinbefore and hereinafter,
including the tautomers, the stereoisomers thereof, the mixtures thereof and the salts thereof.

According to this embodiment preferred meanings of the group $R^1$ are hydrogen, fluorine, chlorine, bromine, iodine, $C_{1-4}$-alkyl, $C_{2-6}$-alkynyl, $C_{1-4}$-alkoxy, $C_{2-4}$-alkenyl-$C_{1-4}$-alkoxy, $C_{2-4}$-alkynyl-$C_{1-4}$-alkoxy, methyl substituted by 1 to 3 fluorine atoms, ethyl substituted by 1 to 5 fluorine atoms, methoxy substituted by 1 to 3 fluorine atoms, ethoxy substituted by 1 to 5 fluorine atoms, $C_{1-4}$-alkyl substituted by a hydroxy or $C_{1-3}$-alkoxy group, $C_{2-4}$-alkoxy substituted by a hydroxy or $C_{1-3}$-alkoxy group, $C_{2-6}$-alkenyl, $C_{3-6}$-cycloalkyl, $C_{3-6}$-cycloalkyl-$C_{1-3}$-alkyl, $C_{3-7}$-cycloalkyloxy, $C_{3-6}$-cycloalkyl-$C_{1-3}$-alkoxy, $C_{5-7}$-cycloalkenyloxy, hydroxy, amino, nitro or cyano, while in the $C_{5-6}$-cycloalkyl groups a methylene group may be replaced by O.

Particularly preferred meanings are hydrogen, fluorine, chlorine, bromine, cyano, methyl, ethyl, isopropyl, difluoromethyl, trifluoromethyl, ethynyl, prop-1-yn-1-yl, but-1-yn-1-yl, hydroxy, methoxy, ethoxy, difluoromethoxy, cyclopropyloxy, cyclobutyloxy, cyclopentyloxy, cyclohexyloxy, particularly methyl and chlorine.

Compounds according to a second embodiment of this invention may be described by general formula I, particularly formulae I.1 and I.2, particularly preferably formula I.2, wherein
$R^1$ is selected from the definitions of the group A given hereinbefore and
the other groups and substituents are defined as hereinbefore and hereinafter,
including the tautomers, the stereoisomers thereof, the mixtures thereof and the salts thereof.

According to this second embodiment preferred meanings of the group $R^3$ are hydrogen, fluorine, chlorine, bromine, hydroxy, cyano, $C_{1-6}$-alkyl, trimethylsilylethyl, $C_{2-6}$-alkenyl, $C_{2-6}$-alkynyl, difluoromethyl, trifluoromethyl, $C_{3-7}$-cycloalkyl, $C_{5-7}$-cycloalkenyl, $C_{1-6}$-alkyloxy, difluoromethoxy, trifluoromethoxy, pentafluorethoxy, $C_{3-7}$-cycloalkyloxy, tetrahydrofuranyloxy, tetrahydrofuranonyloxy, $C_{1-6}$-alkylsulphanyl, cyclopropylidenemethyl, aryl or heteroaryl.

According to this second embodiment particularly preferred meanings of the group $R^3$ are hydrogen, fluorine, chlorine, methyl, ethyl, isopropyl, tert.-butyl, ethynyl, 1-propynyl, trimethylsilylethyl, difluoromethyl, trifluoromethyl, cyclopropyl, cyclobutyl, cyclopentyl, methoxy, ethoxy, isopropoxy, cyclopentyloxy, difluoromethoxy, trifluoromethoxy, pentafluorethoxy, tetrahydrofuran-3-yloxy, tetrahydrofuran-2-on-3-yloxy, methylsulphanyl, ethylsulphanyl, isopropylsulphanyl, cyclopropylidenemethyl, phenyl, fluorophenyl, pyridinyl, pyrimidinyl, pyridazinyl, pyrazinyl, imidazolyl, pyrazolyl, triazolyl, tetrazolyl, oxazolyl, oxadiazolyl, thiazolyl or thiadiazolyl.

According to this second embodiment most particularly preferred meanings of the group $R^3$ are hydrogen, fluorine, chlorine, methyl, ethyl, isopropyl, tert.-butyl, ethynyl, 1-propynyl, trimethylsilylethyl, difluoromethyl, trifluoromethyl, cyclopropyl, cyclobutyl, cyclopentyl, methoxy, ethoxy, isopropoxy, cyclopentyloxy, difluoromethoxy, trifluoromethoxy, pentafluorethoxy, tetrahydrofuran-3-yloxy, tetrahydrofuran-2-on-3-yloxy, methylsulphanyl, ethylsulphanyl, isopropylsulphanyl, cyclopropylidenemethyl. Examples of such particularly preferred meanings are methyl, ethyl, methoxy, ethoxy, trimethylsilylethyl, ethynyl, cyclopentyloxy, tetrahydrofuran-3-yloxy, tetrahydrofuran-2-on-3-yloxy, particularly trimethylsilylethyl, ethoxy, cyclopentyloxy and tetrahydrofuran-3-yloxy.

Meanings of other groups and substituents will now be given which are to be regarded as preferred according to general formula I, formulae I.1 and I.2 and also according to the embodiments described hereinbefore:

Preferred meanings of the group $R^2$ are hydrogen, fluorine, chlorine, bromine, methyl, hydroxy, methoxy, ethoxy, trifluoromethoxy, cyano, nitro and methyl substituted by 1 to 3 fluorine atoms.

Particularly preferred meanings of the group $R^2$ are hydrogen, fluorine, hydroxy, methoxy, ethoxy and methyl, particularly hydrogen and methyl.

Preferred meanings of the group $R^4$ are hydrogen and fluorine, particularly hydrogen.

Preferred meanings of the group $R^5$ are hydrogen and fluorine, particularly hydrogen.

The group $R^N$ preferably denotes H, methyl, ethyl or acetyl.

The group $R^6$ preferably denotes according to the invention hydrogen, ($C_{1-8}$-alkyl)oxycarbonyl, $C_{1-8}$-alkylcarbonyl or benzoyl, particularly hydrogen or ($C_{1-6}$-alkyl)oxycarbonyl, $C_{1-6}$-alkylcarbonyl, particularly preferably hydrogen, methylcarbonyl, methoxycarbonyl or ethoxycarbonyl, most particularly preferably hydrogen or methoxycarbonyl.

The substituents $R^{7a}$, $R^{7b}$, $R^{7c}$ preferably represent independently of one another hydrogen, ($C_{1-8}$-alkyl)oxycarbonyl, ($C_{1-18}$-alkyl)carbonyl, benzoyl, particularly hydrogen or ($C_{1-6}$-alkyl)oxycarbonyl, ($C_{1-8}$-alkyl)carbonyl, particularly preferably hydrogen, methoxycarbonyl, ethoxycarbonyl, methylcarbonyl or ethylcarbonyl. Most particularly preferably $R^{7a}$, $R^{7b}$ and $R^{7c}$ represent hydrogen.

The compounds of formula I wherein $R^6$, $R^{7a}$, $R^{7b}$ and $R^{7c}$ according to the invention have a meaning other than hydrogen, for example $C_{1-8}$-alkylcarbonyl, are preferably suitable as intermediate products for the synthesis of compounds of formula I wherein $R^{7a}$, $R^{7b}$ and $R^{7c}$ denote hydrogen.

Particularly preferred compounds of general formula I are selected from among formulae I.2a to I.2d, particularly I.2c:

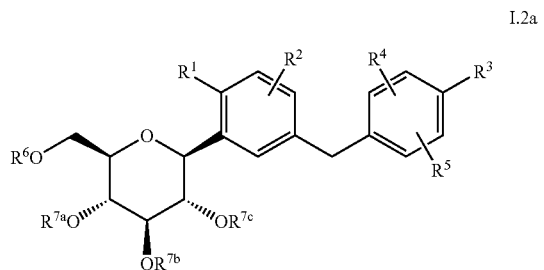

I.2a

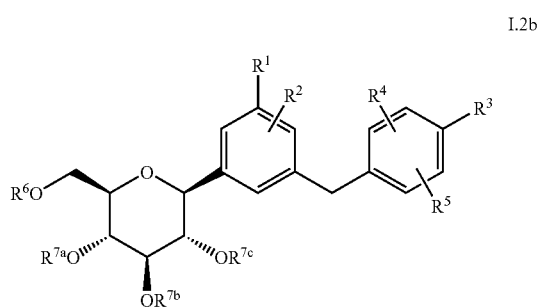

I.2b

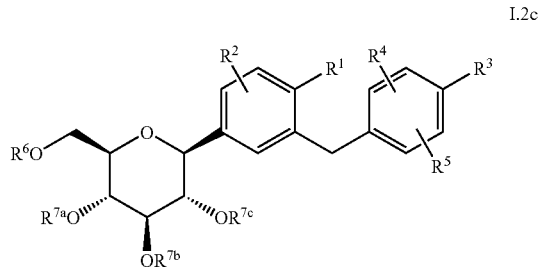

I.2c

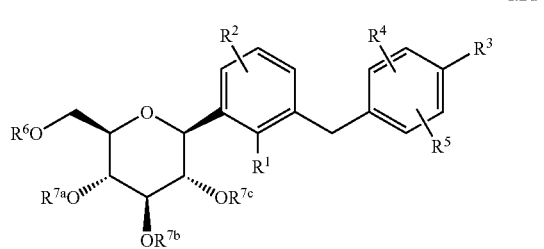

I.2d while the groups $R^1$ to $R^6$ and $R^{7a}$, $R^{7b}$, $R^{7c}$ have one of the meanings given previously, particularly have one of the meanings given specified as being preferred; and particularly $R^1$ denotes hydrogen, fluorine, chlorine, bromine, iodine, $C_{1-4}$-alkyl, $C_{2-6}$alkynyl, $C_{1-4}$-alkoxy, $C_{2-4}$-alkenyl-$C_{1-4}$-alkoxy, $C_{2-4}$-alkynyl-$C_{1-4}$-alkoxy, methyl substituted by 1 to 3 fluorine atoms, ethyl substituted by 1 to 5 fluorine atoms, methoxy substituted by 1 to 3 fluorine atoms, ethoxy substituted by 1 to 5 fluorine atoms, $C_{1-4}$-alkyl substituted by a hydroxy or $C_{1-3}$-alkoxy group, $C_{2-4}$-alkoxy substituted by a hydroxy or $C_{1-3}$-alkoxy group, $C_{2-6}$-alkenyl, $C_{3-6}$-cycloalkyl, $C_{3-6}$-cycloalkyl-$C_{1-3}$-alkyl, $C_{3-7}$-cycloalkyloxy, $C_{3-6}$-cycloalkyl-$C_{1-3}$-alkoxy, $C_{5-7}$-cycloalkenyloxy, hydroxy, amino, nitro or cyano, while in the $C_{5-6}$-cycloalkyl groups a methylene group may be replaced by O; particularly preferably denotes hydrogen, fluorine, chlorine, bromine, cyano, methyl, ethyl, isopropyl, difluoromethyl, trifluoromethyl, ethynyl, prop-1-yn-1-yl, but-1-yn-1-yl, hydroxy, methoxy, ethoxy, difluoromethoxy, cyclopropyloxy, cyclobutyloxy, cyclopentyloxy or cyclohexyloxy; and $R^2$ denotes hydrogen, fluorine, hydroxy, methoxy, ethoxy or methyl, particularly hydrogen or methyl; and $R^3$ is selected from the group B consisting of trimethylsilylethyl, ethynyl, 1-propyn-1-yl, 1-butyn-1-yl, tert.-butylethynyl, 2-hydroxyprop-2-ylethynyl, 2-methoxyprop-2-ylethynyl, 3-hydroxy-1-propyn-1-yl, 3-methoxy-1-propyn-1-yl, ethenyl, 1-propenyl, 1-butenyl, tert.-butylethenyl, cyclopropyloxy, cyclobutyloxy, cyclopentyloxy, cyclohexyloxy, tetrahydrofuranyloxy, tetrahydrothiophenyloxy, 1,1-dioxotetrahydrothiophenyloxy, tetrahydropyranyloxy, tetrahydrothiopyranyloxy, 1,1-dioxotetrahydrothiopyranyloxy, tetrahydrofuranonyloxy, piperidinyloxy, piperidinonyloxy, pyrrolidin-3-yloxy, pyrrolidinone-3-yloxy, tetrahydrofuranyl-sulphanyl, cyclopropylsulphanyl, cyclobutylsulphanyl, cyclopentylsulphanyl and cyclohexylsulphanyl, while the —NH group in a piperidinyl, piperidinonyl, pyrrolidinyl or pyrrolidinonyl ring may be substituted by $R^N$, particularly $C_{1-3}$-alkyl or acetyl; is particularly preferably selected from trimethylsilylethyl, ethynyl, 2-hydroxyprop-2-ylethynyl, 2-methoxyprop-2-ylethynyl, 3-hydroxy-1-propyn-1-yl, 3-methoxy-1-propyn-1-yl, cyclopropyloxy, cyclobutyloxy, cyclopentyloxy, cyclohexyloxy, tetrahydrofuran-3-yloxy, tetrahydropyran-4-yloxy, piperidin-4-yloxy, N-methylpiperidin-4-yloxy and N-acetylpiperidin-4-yloxy; and $R^4$ denotes hydrogen or fluorine, particularly hydrogen; and $R^5$ denotes hydrogen or fluorine, particularly hydrogen; and $R^6$ denotes hydrogen, ($C_{1-6}$-alkyl)oxycarbonyl, ($C_{1-6}$-alkyl)carbonyl or benzoyl, particularly hydrogen, methylcarbonyl, methoxycarbonyl or ethoxycarbonyl, most particularly preferably hydrogen; and $R^{7a}$, $R^{7b}$, $R^{7c}$ independently of one another represent hydrogen, ($C_{1-6}$-alkyl)oxycarbonyl, ($C_{1-8}$-alkyl)carbonyl or benzoyl, particularly hydrogen, methoxycarbonyl, ethoxycarbonyl, methylcarbonyl or ethylcarbonyl, particularly preferably hydrogen;

including the tautomers, the stereoisomers, the mixtures thereof and the salts thereof.

According to a variant of the embodiments given hereinbefore, other preferred compounds are those wherein the phenyl group which carries the substituent $R^3$ has at least one other substituent $R^4$ and/or $R^5$ which is different from hydrogen. According to this variant, particularly preferred compounds are those which have a substituent $R^4$ representing fluorine.

The phenyl group which carries the substituent $R^3$ is preferably at most monofluorinated.

The compounds of general formula I specified in the experimental section that follows, and the derivatives thereof, wherein $R^6$ has a meaning according to the invention other than hydrogen, particularly wherein $R^6$ denotes ethoxycarbonyl or methoxycarbonyl, including the tautomers, the stereoisomers thereof and the mixtures thereof, are preferred according to the invention.

Particularly preferred compounds of general formula I are selected from among:

(1) 1-chloro-2-(4-cyclopentyloxybenzyl)-4-(β-D-glucopyranos-1-yl)-benzene (2) 1-chloro-4-(β-D-glucopyranos-1-yl)-2-[4-((R)-tetrahydrofuran-3-yloxy)-benzyl]-benzene (3) 1-chloro-4-(β-D-glucopyranos-1-yl)-2-[4-((S)-tetrahydrofuran-3-yloxy)-benzyl]-benzene (4) 1-chloro-4-(β-D-glucopyranos-1-yl)-2-[4-(tetrahydrofuran-2-on-3-yloxy)-benzyl]-benzene (5) 1-chloro-4-(β-D-glucopyranos-1-yl)-2-(4-cyclobutyloxy-benzyl)-benzene (6) 1-chloro-4-(β-D-glucopyranos-1-yl)-2-(4-cyclohexyloxy-benzyl)-benzene (7) 1-chloro-4-(β-D-glucopyranos-1-yl)-2-[4-(tetrahydropyran-4-yloxy)-benzyl]-benzene (8) 1-chloro-4-(β-D-glucopyranos-1-yl)-2-[4-(1-acetyl-piperidin-4-yloxy)-benzyl]-benzene

(10) 1-(β-D-Glucopyranos-1-yl)-4-methyl-3-[4-(tetrahydrofuran-3-yloxy)-benzyl]-benzene

(11) 1-(β-D-Glucopyranos-1-yl)-4-methyl-3-[4-(2-trimethylsilyl-ethyl)-benzyl]-benzene

(12) 1-chloro-4-(β-D-glucopyranos-1-yl)-2-(4-ethynyl-benzyl)-benzene

(13) 1-chloro-4-(β-D-glucopyranos-1-yl)-2-[4-(piperidin-4-yloxy)-benzyl]-benzene

(14) 1-fluoro-4-(β-D-glucopyranos-1-yl)-2-(4-ethynyl-benzyl)-benzene

(15) 1-(β-D-glucopyranos-1-yl)-3-(4-ethynyl-benzyl)-benzene

(16) 1-ethynyl-4-(β-D-glucopyranos-1-yl)-2-(4-ethoxy-benzyl)-benzene

(17) 1-methoxy-4-(β-D-glucopyranos-1-yl)-2-(4-ethynyl-benzyl)-benzene and the derivatives thereof wherein $R^6$ has a meaning according to the invention other than hydrogen, particularly wherein $R^6$ denotes ethoxycarbonyl or methoxycarbonyl, including the tautomers, the stereoisomers thereof and the mixtures thereof.

In the processes according to the invention the groups $R^1$, $R^2$, $R^3$, $R^4$ and $R^5$ preferably have the meanings specified hereinbefore as being preferred. Moreover R' preferably denotes H, $C_{1-3}$-alkyl or benzyl, particularly H, ethyl or methyl. The groups $R^{8a}$, $R^{8b}$, $R^{8c}$ and $R^{8d}$ independently of one another preferably denote H, $C_{1-4}$-alkylcarbonyl or benzyl, particularly H, methylcarbonyl, ethylcarbonyl or benzyl.

The invention also relates to compounds of general formula IV, particularly of general formula IV'

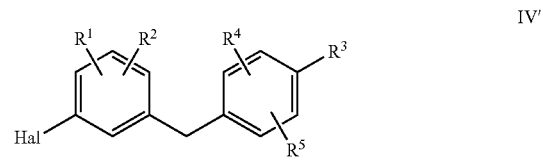

wherein Hal denotes chlorine, bromine or iodine and the groups $R^1$, $R^2$, $R^4$ and $R^5$ are as hereinbefore defined and the group $R^3$ is selected from the group B, as intermediate products or starting materials in the synthesis of the compounds according to the invention. Particularly preferably, the groups $R^1$, $R^2$, $R^3$, $R^4$ and $R^5$ have the meanings given after formulae I.2a to I.2d. Most particularly preferred are compounds of general formula IV', wherein Hal denotes chlorine, bromine or iodine and the groups $R^1$, $R^2$, $R^4$ and $R^5$ have the meanings given after formulae I.2a to I.2d and the group $R^3$ denotes ethynyl or $C_{3-6}$-1-alkyn-1-yl, while the ethynyl group may be substituted by the group —$SiR_3$, while the groups R independently of one another represent $C_{1-4}$-alkyl, $C_{1-4}$-alkoxy or aryl, and the $C_{3-6}$-1-alkyn-1-yl group may be substituted by hydroxy or $C_{1-3}$-alkoxy, particularly hydroxy or methoxy.

The invention also relates to compounds of general formula II, particularly of general formula II'

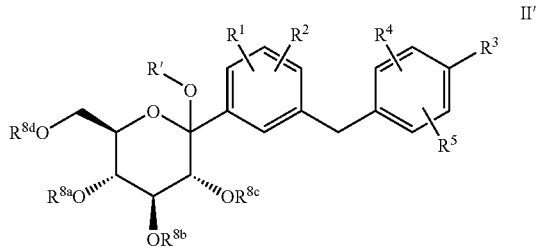

wherein R', $R^a$, $R^{8b}$, $R^{8c}$, $R^{8d}$, $R^1$, $R^2$, $R^3$, $R^4$ and $R^5$ are defined as hereinbefore and hereinafter; particularly wherein R' denotes H, $C_{1-3}$-alkyl or benzyl, particularly H, ethyl or methyl; and the groups $R^{8a}$, $R^{8b}$, $R^{8c}$ and $R^{8d}$ independently of one another represent H, $C_{1-4}$-alkylcarbonyl or benzyl, particularly H, methylcarbonyl, ethylcarbonyl or benzyl and the groups $R^1$, $R^2$, $R^4$ and $R^5$ are as hereinbefore defined and the group $R^3$ is selected from the group B, as intermediate products or starting materials in the synthesis of the compounds according to the invention. Particularly preferably the groups $R^1$, $R^2$, $R^3$, $R^4$ and $R^5$ have the meanings given following formulae I.2a to I.2d.

Some terms used above and hereinafter to describe the compounds according to the invention will now be defined more closely.

The term halogen denotes an atom selected from the group consisting of F, Cl, Br and I, particularly F, Cl and Br.

The term $C_{1-n}$-alkyl, wherein n may have a value of 1 to 18, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{2-n}$-alkynyl, wherein n has a value of 3 to 6, denotes a branched or unbranched hydrocarbon group with 2 to n C atoms and a C≡C triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl etc. Unless otherwise stated alkynyl groups are connected to the remainder of the molecule via the C atom in position 1.

Therefore terms such as 1-propynyl, 2-propynyl, 1-butynyl, etc. are equivalent to the terms 1-propyn-1-yl, 2-propyn-1-yl, 1-butyn-1-yl, etc. This also applies analogously to $C_{2-n}$-alkenyl groups.

The term $C_{1-n}$-alkoxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{1-n}$-alkylcarbonyl denotes a $C_{1-n}$-alkyl-C(=O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc. Preferably the term $C_{3-7}$-cycloalkyl denotes saturated monocyclic groups.

The term $C_{5-n}$-cycloalkenyl denotes a $C_{5-n}$-cycloalkyl group which is as hereinbefore defined and additionally has at least one unsaturated C=C double bond.

The term $C_{3-n}$-cycloalkylcarbonyl denotes a $C_{3-n}$-cycloalkyl-C(=O) group wherein $C_{3-n}$-cycloalkyl is as hereinbefore defined.

The term tri-($C_{1-4}$-alkyl)silyl comprises silyl groups which have identical or two or three different alkyl groups.

The term di-($C_{1-3}$-alkyl)amino comprises amino groups which have identical or two different alkyl groups.

The style used above and hereinafter, in which a bond of a substituent in a phenyl group is shown towards the centre of the phenyl ring, denotes, unless otherwise stated, that this substituent may be bound to any free position of the phenyl ring bearing an H atom.

The compounds according to the invention may be obtained using methods of synthesis known in principle. Preferably the compounds are obtained by the following methods according to the invention which are described in more detail hereinafter.

The glucose derivatives of formula II according to the invention may be synthesised from D-gluconolactone or a derivative thereof by adding the desired benzylbenzene compound in the form of an organometallic compound (Diagram 1).

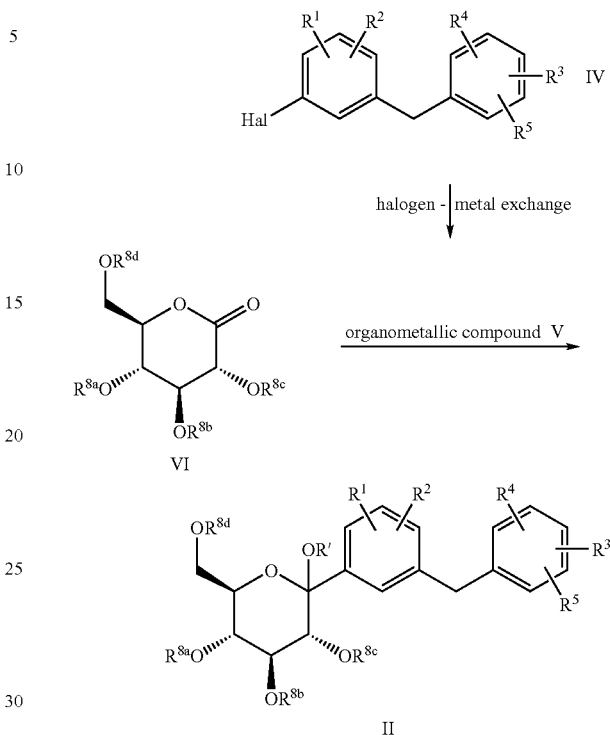

Diagram 1: Addition of an organometallic compound to a glunolactone

The reaction according to Diagram 1 is preferably carried out starting from a halo-benzylbenzene compound of general formula IV, wherein Hal denotes chlorine, bromine or iodine. Starting from the haloaromatic compound IV the corresponding organometallic compound (V) may be prepared either by means of a so-called halogen-metal exchange or by inserting the metal into the carbon-halogen bond. The halogen-metal exchange with bromine or iodine-substituted aromatic groups may be carried out for example with an organolithium compound such as e.g. n-, sec- or tert-butyllithium and thereby yields the corresponding lithiated aromatic group. The analogous magnesium compound may also be generated by a halogen-metal exchange with a suitable Grignard compound such as e.g. isopropylmagnesium bromide or diisopropylmagnesium. The reactions are preferably carried out between 0 and −100° C., particularly preferably between −10 and −80° C., in an inert solvent or mixtures thereof, such as for example diethyl ether, tetrahydrofuran, toluene, hexane or methylene chloride. The magnesium or lithium compounds thus obtained may optionally be transmetallised with metal salts such as e.g. cerium trichloride, to form additional organometallic compounds (V) suitable for addition. Alternatively the organometallic compound (V) may also be prepared by inserting a metal into the carbon-halogen bond of the haloaromatic compound IV. Metals such as e.g. lithium or magnesium are suitable for this. The addition of the organometallic compound V to gluconolactone or derivatives thereof of formula VI is preferably carried out at temperatures between 0 and −100° C., particularly preferably at −30 to −80° C., in an inert solvent or mixtures thereof, to obtain the compound of formula II. The lithiation and/or coupling reaction may also be carried out in microreactors and/or micromixers in order to avoid low temperatures; for example analogously to the processes described in WO 2004/076470.

Suitable solvents are e.g. diethyl ether, toluene, methylene chloride, hexane, tetrahydrofuran or mixtures thereof. The reactions may be carried out without any further adjuvants or in the case of unreactive coupling partners in the presence of Lewis acids such as e.g. $BF_3*OEt_2$ or $Me_3SiCl$ (see M. Schlosser, Organometallics in Synthesis, John Wiley & Sons, Chichester/New York/Brisbane/Toronto/Singapore, 1994). Preferred definitions of the groups $R^{8a}$, $R^{8b}$, $R^{8c}$ and $R^{8d}$ are benzyl, substituted benzyl, trialkylsilyl, particularly preferably trimethylsilyl, triisopropylsilyl, 4-methoxybenzyl and benzyl. If two adjacent groups of the group consisting of $R^{8a}$, $R^{8b}$, $R^{8c}$ and $R^{8d}$ are linked together, these two groups are preferably part of a benzylideneacetal, 4-methoxybenzylideneacetal, isopropylketal or constitute a 2,3-dimethoxy-butylene group which is linked via the 2 and 3 positions of the butane with the adjacent oxygen atoms of the pyranose ring. The group R' preferably denotes hydrogen or $C_{1-4}$-alkyl, particularly preferably hydrogen, methyl or ethyl. The group R' is inserted after the addition of the organometallic compound V or a derivative thereof to the gluconolactone VI. For this purpose the reaction solution is treated with an alcohol such as e.g. methanol or ethanol or water in the presence of an acid such as e.g. methanesulphonic acid, toluenesulphonic acid, sulphuric acid or hydrochloric acid.

The synthesis of haloaromatic compound of formula IV may be carried out using standard transformations in organic chemistry or at least methods known from the specialist literature in organic synthesis (see inter alia J. March, Advanced Organic Reactions, Reactions, Mechanisms, and Structure, 4th Edition, John Wiley & Sons, Chichester/New York/Brisbane/Toronto/Singapore, 1992 and literature cited therein). The synthesis strategies described in the following provide a demonstration of this, by way of example.

Diagram 2: Synthesis strategy 1

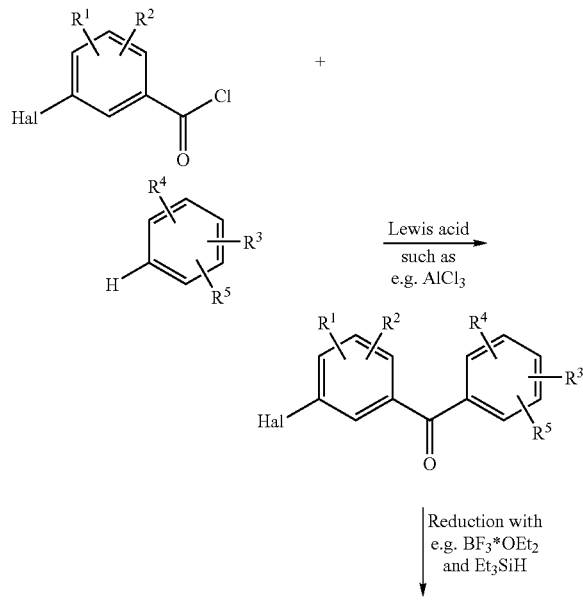

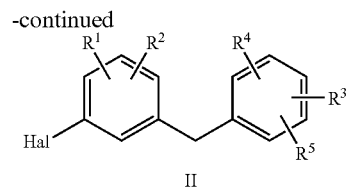

II

Synthesis strategy 1 (Diagram 2) shows the preparation of the haloaromatic compound of formula II starting from a benzoylchloride and a second aromatic group which is converted by Friedel-Crafts acylation into the diphenylketone derivative. This classic reaction has a wide substrate breadth and is carried out in the presence of a catalyst which is used in catalytic or stoichiometric amounts, such as e.g. $AlCl_3$, $FeCl_3$, iodine, iron, $ZnCl_2$, sulphuric acid or trifluoromethanesulphonic acid. Instead of the carboxylic acid chloride it is also possible to use the carboxylic acid, an anhydride or ester thereof or the corresponding benzonitrile. The reactions are preferably carried out in chlorinated hydrocarbons such as e.g. dichloromethane and 1,2-dichloroethane at temperatures from −30 to 120° C., preferably at 30 to 100° C. However, solvent-free reactions or reactions in a microwave oven are also possible. In a second reaction step the diphenylketone is reduced to the diphenylmethane. This reaction may be carried out in two steps via the corresponding diphenylmethanol or in one step. In the two-step variant the ketone is reduced with a reducing agent such as for example a metal hydride such as e.g. $NaBH_4$, $LiAlH_4$ or $iBu_2AlH$ to form the alcohol. The resulting alcohol can be converted in the presence of a Lewis acid such as for example $BF_3*OEt_2$, trifluoroacetic acid, $InCl_3$ or $AlCl_3$ with a reducing agent such as e.g. $Et_3SiH$, $NaBH_4$, or $Ph_2SiClH$ to form the desired diphenylmethane. The one-step process starting from the ketone to obtain the diphenylmethane may be carried out e.g. with a silane such as e.g. $Et_3SiH$, a borohydride such as e.g. $NaBH_4$ or an aluminium hydride such as $LiAlH_4$ in the presence of a Lewis acid such as for example $BF_3*OEt_2$, tris(pentafluorophenyl)-borane, trifluoroacetic acid, aluminium chloride or $InCl_3$. The reactions are preferably carried out in solvents such as e.g. halogenated hydrocarbons such as dichloromethane, toluene or acetonitrile at temperatures of −30 to 150° C., preferably at 20 to 100° C. Reductions with hydrogen in the presence of a transition metal catalyst such as e.g. Pd on charcoal are another possible method of synthesis. Reductions according to Wolff-Kishner or variants thereof are also possible. The ketone is first of all converted with hydrazine or a derivative thereof, such as e.g. 1,2-bis(tert-butyldimethylsilyl)hydrazine, into the hydrazone which breaks down under strongly basic reaction conditions and heating to form the diphenylmethane and nitrogen. The reaction may be carried out in one reaction step or after isolation of the hydrazone or a derivative thereof in two separaten reaction steps. Suitable bases include e.g. KOH, NaOH or KOtBu in solvents such as e.g. ethyleneglycol, toluene, DMSO, 2-(2-butoxyethoxy)ethanol or t-butanol; solvent-free reactions are also possible. The reactions may be carried out at temperatures between 20 to 250° C., preferably between 80 to 200° C. An alternative to the basic conditions of the Wolff-Kishner reduction is the Clemmensen reduction which takes place under acid conditions, which may also be used here.

Diagram 3: Syntehsis strategy 2

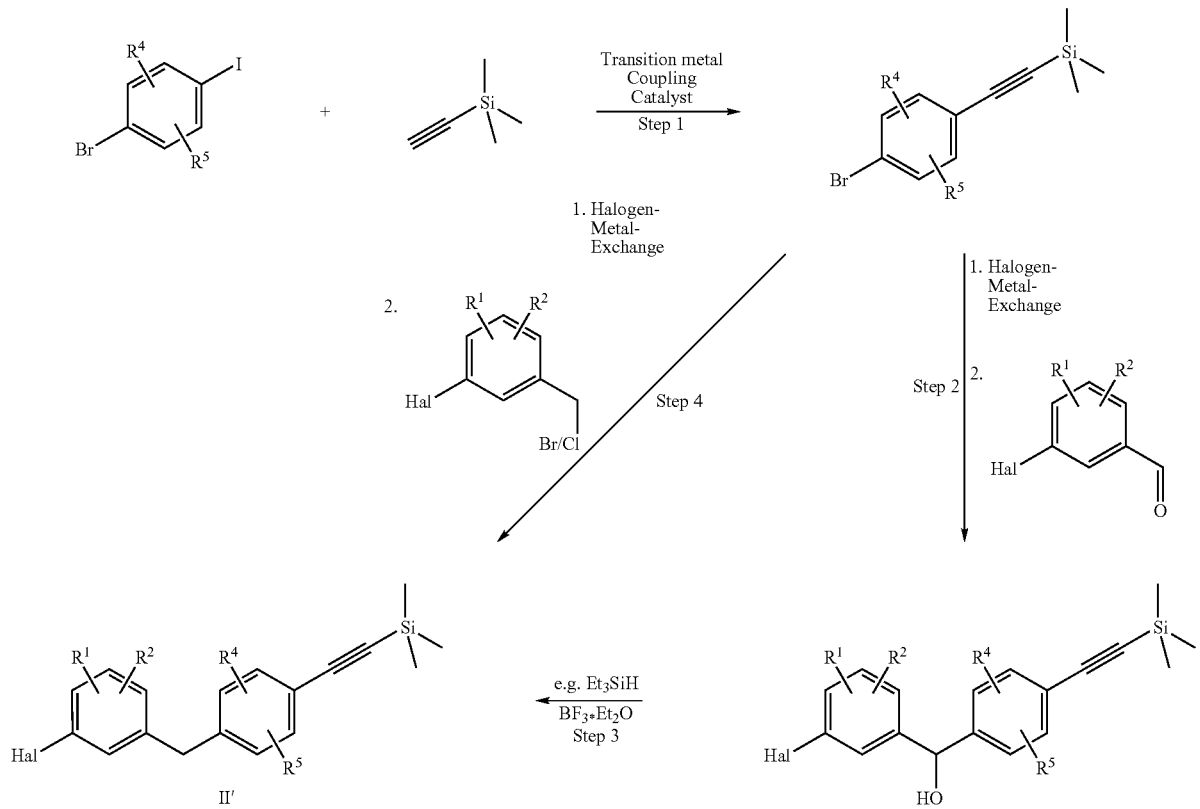

The second synthesis strategy (Diagram 3) shows another possible way of synthesising the halogen-aromatic groups of formula II' illustrated by the example of a trimethylsilylacetylene-substituted diphenylmethane. Starting from an aromatic group which carries two groups selected from among iodine, bromine, chlorine or sulphonate such as e.g. trifluoromethylsulphonate, an alkyne group is attached via a transition metal-catalysed monocoupling to the more reactive end of the dihaloaromatic compound, the iodine-carbon bond (step 1). The catalysts used are for example elemental palladium or nickel or salts or complexes thereof. The reactions may be carried out with the alkyne itself or metal acetylidene therefrom. If the alkyne itself is used, coupling may be carried out in the presence of a base such as e.g. $NEt_3$ and a co-catalyst such as e.g. a copper salt such as CuI (Sonogashira coupling). The reactions are not limited to trimethylsilylacetylene, but allow the use of a number of terminal alkynes. The reaction is extensively documented with all its variations in the literature (see P. J. Stang, F. Diederich, *Metal-Catalyzed Cross-Coupling Reactions*, Wiley-VCH, Weinheim, 1997 and *Angew. Chem. Int. Ed.* 2003, 42, 1566-1568 and literature cited therein). The other two steps for preparing the diphenylmethane derivatives comprise transfunctionalising the alkyne-substituted aromatic group to obtain a metallised (Mg, Li) aromatic group which may be prepared, for example, by a halogen-metal exchange as described hereinbefore (step 2). This metallised aromatic compound which may be used directly or after further transmetallation, is added to a benzaldehyde derivative. This forms the diphenylmethanol shown in the diagram. Alternatively it is also possible to use a benzoic acid derivative such as e.g. a benzoic acid ester, anhydride, chloride or the acid itself or the benzonitrile. Instead of the alcohol the corresponding ketone is formed, which may also be obtained by Friedel-Crafts acylation as described above. Further reaction of both the alcohol and the ketone to form the diphenylmethane derivative has already been described above (step 3). The trimethylsilylethynylated aromatic halogen compound may however also be converted directly after transmetallation into the desired product (step 4). For this, the lithium or magnesium aromatic group obtained after a halogen-metal exchange is reacted with a benzylelectrophil such as e.g. a benzyl bromide or chloride. The reaction may be carried out without or, better still, in the presence of a transition metal catalyst, such as e.g. a copper salt or a palladium complex (see e.g. *Org. Lett.* 2001, 3, 2871-2874 and literature cited therein). The aromatic lithium or magnesium group may however also be transmetallised first, for example, to obtain the corresponding boric acids, boric acid esters, stannanes, silanes or zinc compounds. Then it is attached by means of a transition metal such as e.g. palladium, nickel, rhodium, copper or iron to the benzyl group (see L. Brandsma, S. F. Vasilevsky, H. D. Verkruijsse, *Application of Transition Metal Catalysts in Organic Synthesis*, Springer-Verlag, Berlin/Heidelberg, 1998). The reactions of the alkyne-substituted aromatic group to the intermediate product of formula II' according to steps 2 and 3 or step 4, which are illustrated by way of example here for $R^3$ denoting ethynyl or trimethylsilylethynyl, may also be carried out analogously with other $R^3$-substituted aromatic groups.

Diagram 4: Synthesis strategy 3

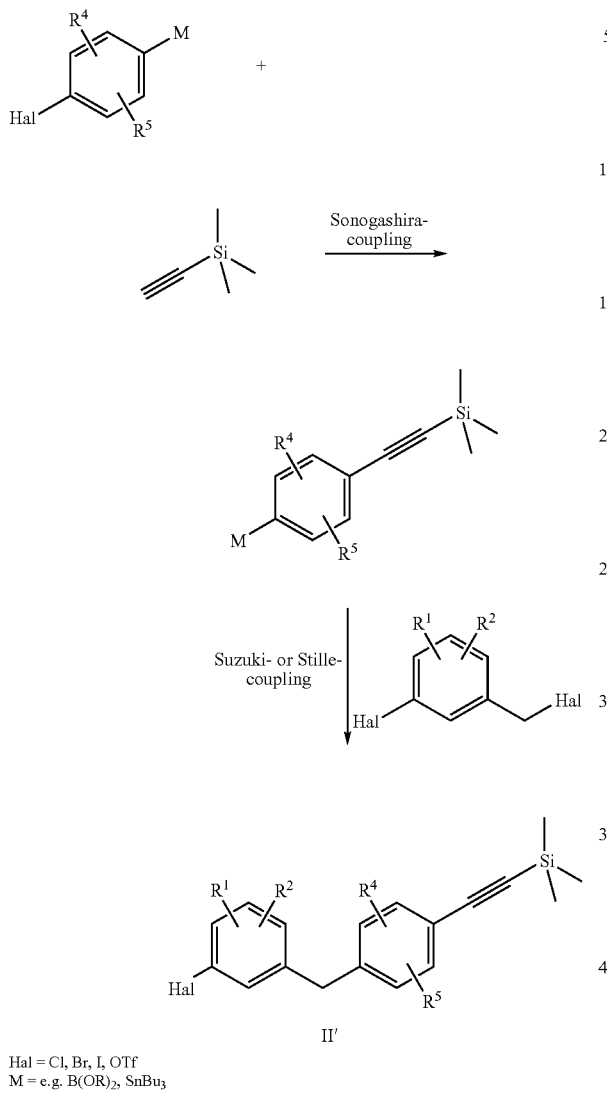

Hal = Cl, Br, I, OTf
M = e.g. B(OR)$_2$, SnBu$_3$

Synthesis strategy 3 (Diagram 4) shows an alternative form of synthesis strategy 2, which is also illustrated using the example of an aromatic trimethylsilylethynyl group II', but should not be limited thereto. The synthesis starts with an aromatic group which carries both a Hal group, which denotes a halogen atom chlorine, bromine or iodine, or a pseudohalogen group, such as e.g. trifluoromethanesulphonate, and also a metallic centre M, such as e.g. a B(OH)$_2$, Si(OAlk)$_3$ or SnBu$_3$ group. The two centres thus "activated" may be exchanged chemoselectively one after the other. Synthesis strategy 3 illustrates this with an example in which first of all the halogen atom Hal is exchanged for an alkyne substituent in a transition metal-catalysed reaction such as e.g. the so-called Sonogashira coupling. In the second step the metallic centre M is exchanged for a benzyl group which is activated e.g. as the benzyl halide in another transition metal-catalysed coupling, to obtain the desired product (see e.g. Tetrahedron Lett. 2003, 44, 9255-9258 and literature cited therein). Both steps may be carried out using transition metals such as e.g. palladium, rhodium, nickel, copper or iron, or complexes thereof. Both types of reaction are described in detail in the literature. The method is not restricted to that shown here but may also involve reverseing the sequence of the two reaction steps. In this case, the metallic centre M is first linked to the benzyl group and then the halogen or pseudohalogen group Hal is exchanged for the alkyne.

In order to prepare compounds of general formula I, in process a) according to the invention, a compound of general formula II

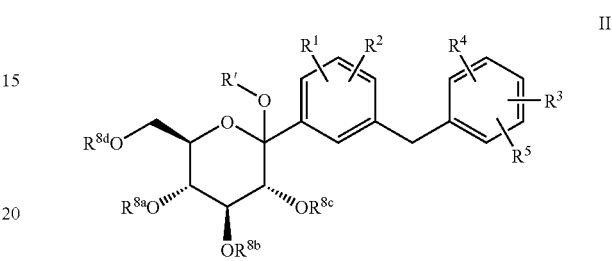

wherein R', $R^1$ to $R^5$ are as hereinbefore defined and $R^{8a}$, $R^{8b}$, $R^{8c}$, $R^{8d}$ are as hereinbefore defined and independently of one another represent for example acetyl, pivaloyl, benzoyl, tert-butoxycarbonyl, benzyloxycarbonyl, trialkylsilyl, benzyl or substituted benzyl or in each case two adjacent groups $R^{8a}$, $R^{8b}$, $R^{8c}$, $R^{8d}$ form a benzylideneacetal or isopropylideneketal or a 2,3-dimethoxy-butylene group which is linked via position 2 and 3 of the butylene group to the oxygen atoms of the pyranose ring and forms with them a substituted dioxane, which may be obtained as hereinbefore described, is reacted with a reducing agent in the presence of a Lewis or Brønsted acid.

Suitable reducing agents for the reaction include for example silanes, such as triethyl, tripropyl, triisopropyl or diphenylsilane, sodium borohydride, sodium cyanoborohydride, zinc borohydride, boranes, lithium aluminium hydride, diisobutylaluminium hydride or samarium iodide. The reductions are carried out without or in the presence of a suitable Brønsted acid, such as e.g. hydrochloric acid, toluenesulphonic acid, trifluoroacetic acid or acetic acid, or Lewis acid, such as e.g. boron trifluoride etherate, trimethylsilyltriflate, titaniium tetrachloride, tin tetrachloride, scandium triflate or zinc iodide. Depending on the reducing agent and the acid the reaction may be carried out in a solvent, such as for example methylene chloride, chloroform, acetonitrile, toluene, hexane, diethyl ether, tetrahydrofuran, dioxane, ethanol, water or mixtures thereof at temperatures between −60° C. and 120° C. One particularly suitable combination of reagents consists for example of triethylsilane and boron trifluoride etherate, which is conveniently used in acetonitrile or dichloromethane at temperatures of −60° C. and 60° C. Moreover, hydrogen may be used in the presence of a transition metal catalyst, such as e.g. palladium on charcoal or Raney nickel, in solvents such as tetrahydrofuran, ethyl acetate, methanol, ethanol, water or acetic acid, for the transformation described.

Alternatively, in order to prepare compounds of general formula I according to process b) according to the invention, in a compound of general formula III

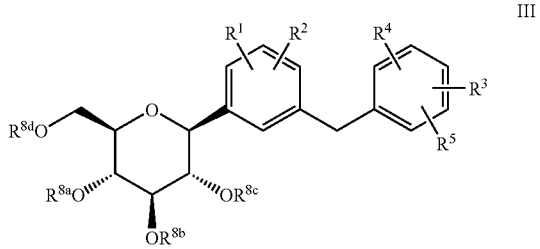

wherein $R^1$ to $R^5$ are as hereinbefore defined and $R^{8a}$ to $R^{8d}$ denote one of the protective groups defined hereinbefore, such as e.g. an acyl, arylmethyl, acetal, ketal or silyl group, and which may be obtained for example by reduction from the compound of formula II as hereinbefore described, the protective groups are cleaved.

Any acyl protecting group used is cleaved for example hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or aprotically, e.g. in the presence of iodotrimethylsilane, at temperatures between 0 and 120° C., preferably at temperatures between 10 and 100° C. A trifluoroacetyl group is preferably cleaved by treating with an acid such as hydrochloric acid, optionally in the presence of a solvent such as acetic acid at temperatures between 50 and 120° C. or by treating with sodium hydroxide solution optionally in the presence of a solvent such as tetrahydrofuran or methanol at temperatures between 0 and 50° C.

Any acetal or ketal protecting group used is cleaved for example hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or aprotically, e.g. in the presence of iodotrimethylsilane, at temperatures between 0 and 120° C., preferably at temperatures between 10 and 100° C.

A trimethylsilyl group is cleaved for example in water, an aqueous solvent mixture or a lower alcohol such as methanol or ethanol in the presence of a base such as lithium hydroxide, sodium hydroxide, potassium carbonate or sodium methoxide. In aqueous or alcoholic solvents, acids such as e.g. hydrochloric acid, trifluoroacetic acid or acetic acid are also suitable. For cleaving in organic solvents, such as for example diethyl ether, tetrahydrofuran or dichloromethane, it is also suitable to use fluoride reagents, such as e.g. tetrabutylammonium fluoride.

A benzyl, methoxybenzyl or benzyloxycarbonyl group is advantageously cleaved hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane optionally using a solvent such as methylene chloride, dioxane, methanol or diethylether.

In the reactions described hereinbefore, any reactive groups present such as ethynyl, hydroxy, amino, alkylamino or imino groups may be protected during the reaction by conventional protecting groups which are cleaved again after the reaction.

For example, a protecting group for an ethynyl group may be the trimethylsilyl or triisopropyl group. The 2-hydroxyisoprop-2-yl group may also be used as a protective group.

For example, a protecting group for a hydroxy group may be a trimethylsilyl, acetyl, trityl, benzyl or tetrahydropyranyl group.

Protecting groups for an amino, alkylamino or imino group may be, for example, a formyl, acetyl, trifluoroacetyl, ethoxycarbonyl, tert.butoxycarbonyl, benzyloxycarbonyl, benzyl, methoxybenzyl or 2,4-dimethoxybenzyl group.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+) or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, the compounds obtained may be converted into mixtures, for example 1:1 or 1:2 mixtures with amino acids, particularly with alpha-amino acids such as proline or phenylalanine, which may have particularly favourable properties such as a high crystallinity.

The compounds according to the invention are advantageously also obtainable using the methods described in the examples that follow, which may also be combined for this purpose with methods known to the skilled man from the literature, for example, particularly the methods described in WO 98/31697, WO 01/27128, WO 02/083066, WO 03/099836 and WO 2004/063209.

As already mentioned, the compounds of general formula I according to the invention and the physiologically acceptable salts thereof have valuable pharmacological properties, particularly an inhibitory effect on the sodium-dependent glucose cotransporter SGLT, preferably SGLT2.

The Biological Properties of the New Compounds may be Investigated as Follows:

The ability of the substances to inhibit the SGLT-2 activity may be demonstrated in a test set-up in which a CHO-K1 cell line (ATCC No. CCL 61) or alternatively an HEK293 cell line (ATCC No. CRL-1573), which is stably transfected with an expression vector pZeoSV (Invitrogen, EMBL accession number L36849), which contains the cDNA for the coding sequence of the human sodium glucose cotransporter 2 (Genbank Acc. No.NM_003041) (CHO-hSGLT2 or HEK-hSGLT2). These cell lines transport $^{14}$C-labelled alpha-methyl-glucopyranoside ($^{14}$C-AMG, Amersham) into the interior of the cell in sodium-dependent manner.

The SGLT-2 assay is carried out as follows:

CHO-hSGLT2 cells are cultivated in Ham's F12 Medium (BioWhittaker) with 10% foetal calf serum and 250 µg/ml zeocin (Invitrogen), and HEK293-hSGLT2 cells are cultivated in DMEM medium with 10% foetal calf serum and 250 µg/ml zeocin (Invitrogen). The cells are detached from the culture flasks by washing twice with PBS and subsequently treating with trypsin/EDTA. After the addition of cell culture medium the cells are centrifuged, resuspended in culture medium and counted in a Casy cell counter. Then 40,000 cells per well are seeded into a white, 96-well plate coated with poly-D-lysine and incubated overnight at 37° C., 5% $CO_2$. The cells are washed twice with 250 µl of assay buffer (Hanks Balanced Salt Solution, 137 mM NaCl, 5.4 mM KCl, 2.8 mM $CaCl_2$, 1.2 mM $MgSO_4$ and 10 mM HEPES (pH7.4), 50 µg/ml of gentamycin). 250 µl of assay buffer and 5 µl of test compound are then added to each well and the plate is incubated for a further 15 minutes in the incubator. 5 µl of 10% DMSO are used as the negative control. The reaction is started by adding 5 µl of $^{14}$C-AMG (0.05 µCi) to each well. After 2 hours' incubation at 37° C., 5% $CO_2$, the cells are washed again with 250 µl of PBS (20° C.) and then lysed by the addition of 25 µl of 0.1 N NaOH (5 min. at 37° C.). 200 µl of MicroScint20 (Packard) are added to each well and incubation is continued for a further 20 min at 37° C. After this incubation the radioactivity of the $^{14}$C-AMG absorbed is measured in a Topcount (Packard) using a $^{14}$C scintillation program.

To determine the selectivity with respect to human SGLT1 an analogous test is set up in which the cDNA for hSGLT1 (Genbank Acc. No. NM000343) instead of hSGLT2 cDNA is expressed in CHO-K1 or HEK293 cells.

The compounds of general formula I according to the invention may for example have EC50 values below 1000 nM, particularly below 200 nM, most preferably below 50 nM.

In view of their ability to inhibit the SGLT activity, the compounds of general formula I according to the invention and the corresponding pharmaceutically acceptable salts thereof are theoretically suitable for the treatment and/or preventative treatment of all those conditions or diseases which may be affected by the inhibition of the SGLT activity, particularly the SGLT-2 activity. Therefore, compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, edema and hyperuricaemia. These substances are also suitable for preventing beta-cell degeneration such as e.g. apoptosis or necrosis of pancreatic beta cells. The substances are also suitable for improving or restoring the functionality of pancreatic cells, and also of increasing the number and size of pancreatic beta cells. The compounds according to the invention may also be used as diuretics or antihypertensives and are suitable for the prevention and treatment of acute renal failure.

In particular, the compounds according to the invention, including the physiologically acceptable salts thereof, are suitable for the prevention or treatment of diabetes, particularly type 1 and type 2 diabetes mellitus, and/or diabetic complications.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may also be used in conjunction with other active substances, particularly for the treatment and/or prevention of the diseases and conditions mentioned above. Other active substances which are suitable for such combinations include for example those which potentiate the therapeutic effect of an SGLT antagonist according to the invention with respect to one of the indications mentioned and/or which allow the dosage of an SGLT antagonist according to the invention to be reduced. Therapeutic agents which are suitable for such a combination include, for example, antidiabetic agents such as metformin, sulphonylureas (e.g. glibenclamide, tolbutamide, glimepiride), nateglinide, repaglinide, thiazolidinediones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. LAF237, MK-431), alpha2-antagonists, insulin and insulin analogues, GLP-1 and GLP-1 analogues (e.g. exendin-4) or amylin. The list also includes inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully 1/5 of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the sodium-dependent glucose cotransporter SGLT. These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

In the foregoing and following text, H atoms of hydroxyl groups are not explicitly shown in every case in structural formulae. The Examples that follow are intended to illustrate the present invention without restricting it:

Preparation of the Starting Compounds:

EXAMPLE I

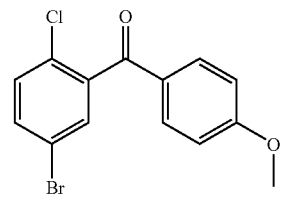

(5-bromo-2-chloro-phenyl)-(4-methoxy-phenyl)-methanone 38.3 ml oxalyl chloride and 0.8 ml of dimethylformamide are added to a mixture of 100 g of 5-bromo-2-chloro-benzoic acid in 500 ml dichloromethane. The reaction mixture is stirred for 14 h, then filtered and separated from all volatile constituents in the rotary evaporator. The residue is dissolved in 150 ml dichloromethane, the solution is cooled to −5° C., and 46.5 g of anisole are added. Then 51.5 g of aluminium trichloride are added batchwise so that the temperature does not exceed 5° C. The solution is stirred for another 1 h at 1-5° C. and then poured onto ice. The organic phase is separated off and the aqueous phase is extracted another three times with dichloromethane. The combined organic phases are washed with aqueous 1 M hydrochloric acid, twice with 1 M sodium hydroxide solution and with saturated sodium chloride solution. Then the organic phase is dried, the solvent is removed and the residue is recrystallised in ethanol.

Yield: 86.3 g (64% of theory) Mass spectrum (ESI$^+$): m/z=325/327/329 (Br+Cl) [M+H]$^+$ The following compounds are obtained analogously to Example I:

(1) (5-bromo-2-iodo-phenyl)-(4-ethoxy-phenyl)-methanone

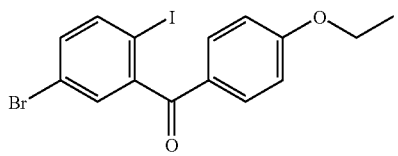

Mass spectrum (ESI$^+$): m/z=431/433 (Br) [M+H]$^+$ (2) (5-bromo-2-chloro-phenyl)-(4-iodo-phenyl)-methanone

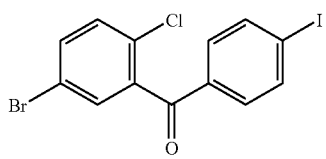

EXAMPLE II

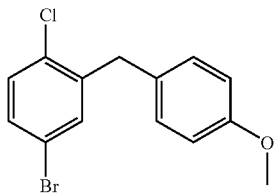

4-bromo-1-chloro-2-(4-methoxy-benzyl)-benzene

A solution of 86.2 g (5-bromo-2-chloro-phenyl)-(4-methoxy-phenyl)-methanone and 101.5 ml triethylsilane in 75 ml dichloromethane and 150 ml acetonitrile is cooled to 10° C. Then with stirring 50.8 ml of boron trifluoride etherate are added so that the temperature does not exceed 20° C. The solution is stirred for 14 h at ambient temperature, before another 9 ml triethylsilane and 4.4 ml boron trifluoride etherate are added. The solution is stirred for a further 3 h at 45-50° C. and then cooled to ambient temperature. A solution of 28 g potassium hydroxide in 70 ml of water is added and the mixture is stirred for 2 h. Then the organic phase is separated off and the aqueous phase is extracted another three times with diisopropylether. The combined organic phases are washed twice with 2 M potassium hydroxide solution and once with aqueous sodium chloride solution and then dried over sodium sulphate. After the solvent has been eliminated the residue is stirred in ethanol, separated off again and dried at 60° C.

Yield: 50.0 g (61% of theory) Mass spectrum (ESI$^+$): m/z=310/312/314 (Br+Cl) [M+H]$^+$ The following compounds are obtained analogously to Example II:

(1) 4-bromo-1-iodo-2-(4-ethoxy-benzyl)-benzene

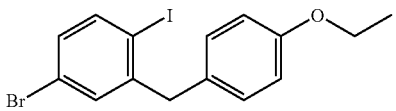

Mass spectrum (ESI$^+$): m/z=434/436 [M+NH$_4$]$^+$ (2) 4-bromo-1-chloro-2-(4-iodo-benzyl)-benzene

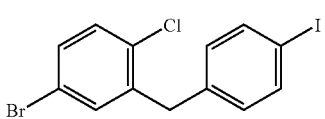

EXAMPLE III

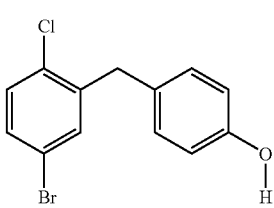

4-(5-bromo-2-chloro-benzyl)-phenol

A solution of 14.8 g 4-bromo-1-chloro-2-(4-methoxy-benzyl)-benzene in 150 ml dichloromethane is cooled in the ice bath. Then 50 ml of a 1 M solution of boron tribromide in dichloromethane are added, and the solution is stirred for 2 h at ambient temperature. The solution is then cooled in the ice bath again, and saturated potassium carbonate solution is added dropwise. At ambient temperature the mixture is adjusted with aqueous 1 M hydrochloric acid to a pH of 1, the organic phase is separated off and the aqueous phase is extracted another three times with ethyl acetate. The combined organic phases are dried over sodium sulphate, and the solvent is removed completely.

Yield: 13.9 g (98% of theory) Mass spectrum (ESI$^-$): m/z=295/297/299 (Br+Cl) [M−H]$^-$

EXAMPLE IV

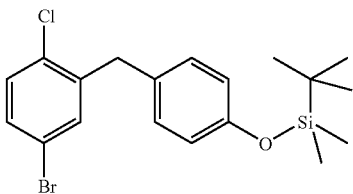

[4-(5-bromo-2-chloro-benzyl)-phenoxy]-tert-butyl-dimethyl-silane

A solution of 13.9 g 4-(5-bromo-2-chloro-benzyl)-phenol in 140 ml dichloromethane is cooled in the ice bath. Then 7.54 g tert-butyldimethylsilylchlorid in 20 ml dichloromethane are added followed by 9.8 ml triethylamine and 0.5 g dimethylaminopyridine. The solution is stirred for 16 h at ambient temperature and then diluted with 100 ml dichloromethane. The organic phase is washed twice with aqueous 1 M hydrochloric acid and once with aqueous sodium hydrogen carbonate solution and then dried over sodium sulphate. After the solvent has been eliminated the residue is filtered through silica gel (cyclohexane/ethyl acetate 100:1).

Yield: 16.8 g (87% of theory) Mass spectrum (EI): m/z=410/412/414 (Br+Cl) [M]$^+$

EXAMPLE V

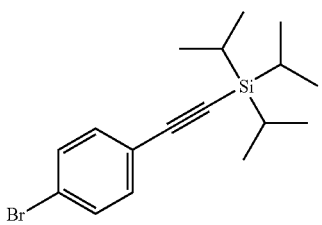

1-bromo-4-triisopropylsilylethynyl-benzene

Under argon 11.6 ml triisopropylacetylen and 14.4 ml triethylamine followed by 0.2 g copper iodide and 0.73 g bis-(triphenylphosphine)-palladium dichloride are added to an oxygen-free solution of 15.0 g 1-bromo-4-iodo-benzene in 150 ml dry tetrahydrofuran. The solution is stirred for 16 h at ambient temperature and then filtered through Celite and evaporated down. The residue is chromatographed through silica gel (cyclohexane).

Yield: 17.4 g (100% of theory) Mass spectrum (ESI$^+$): m/z=336/338 (Br) [M]$^+$ The following compounds are obtained analogously to Example V:

(1) 4-bromo-1-(triisopropylsilylethynyl)-2-(4-ethoxy-benzyl)-benzene 4-bromo-1-iodo-2-(4-ethoxy-benzyl)-benzene is used as the starting material for the coupling reaction described hereinbefore.

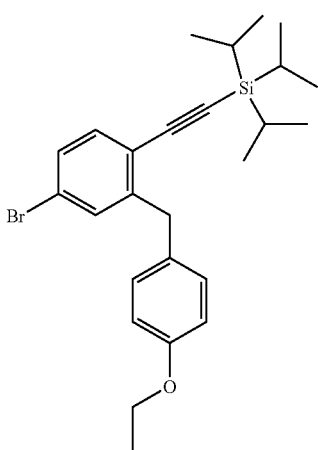

Mass spectrum (ESI$^+$): m/z=471/473 (Br) [M+H]$^+$ (2) [4-(5-bromo-2-chloro-benzyl)-phenylethynyl]-triisopropyl-silane 4-bromo-1-chloro-2-(4-iodo-benzyl)-benzene is used as starting material.

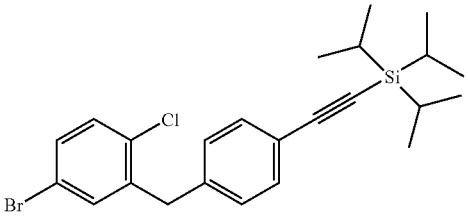

This compound may also be obtained according to Example X.

EXAMPLE VI

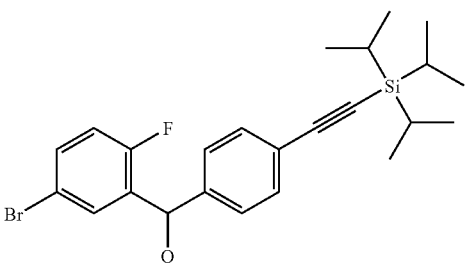

(5-bromo-2-fluoro-phenyl)-{4-[(triisopropylsilyl)-ethynyl]-phenyl}methanol 33.8 ml of a 1.6 M solution of n-butyllithium in hexane are added dropwise under argon to a solution of 17.4 g 1-bromo-4-triisopropylsilylethynyl-benzene in 120 ml dry tetrahydrofuran chilled to −78° C. The solution is stirred for 1 h at −70° C. Then 10.8 g 5-bromo-2-fluoro-benzaldehyde dissolved in 30 ml of tetrahydrofuran are added dropwise over 15 min. The resulting solution is left in the cooling bath to warm up overnight to ambient temperature. Then water is added and the mixture is extracted with ethyl acetate. The combined organic phase are dried over sodium sulphate, and the solvent is removed. The residue is purified through silica gel (cyclohexane/ethyl acetate 4:1).

Yield: 14.3 g (60% of theory) Mass spectrum (ESI$^+$): m/z=461/463 (Br) [M+H]$^+$ The following compounds are obtained analogously to Example VI:

(1) (3-bromo-phenyl)-{4-[(triisopropylsilyl)-ethynyl]-phenyl}-methanol

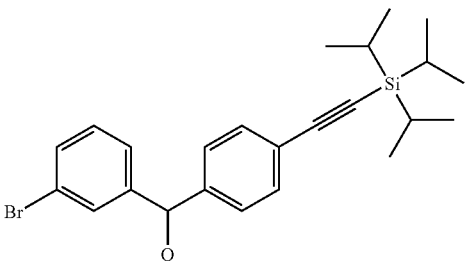

Mass spectrum (ESI$^-$): m/z=487/489 (Br) [M+HCOO]$^-$ (2) (5-bromo-2-methoxy-phenyl)-{4-[(triisopropylsilyl)-ethynyl]-phenyl}methanol

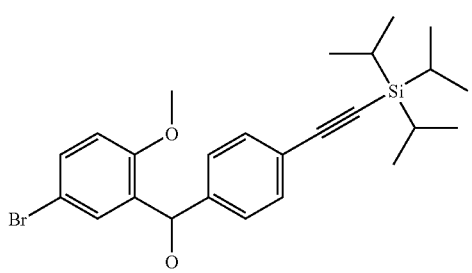

Mass spectrum (ESI⁺): m/z=473/475 (Br) [M+H]⁺

EXAMPLE VII

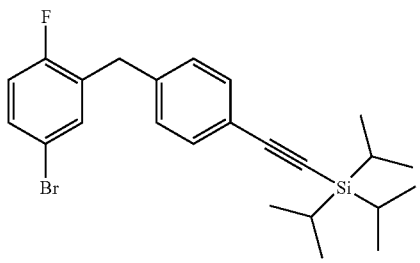

[4-(5-bromo-2-fluoro-benzyl)-phenylethynyl]-triisopropyl-silane

A solution of 5.6 g (5-bromo-2-fluoro-phenyl)-{4-[(triisopropylsilyl)-ethynyl]-phenyl}-methanol and 4.1 ml triethylsilane in 50 ml dichloromethane is cooled in the ice bath. Then 4.7 ml trifluoroacetic acid are slowly added dropwise, and the solution is stirred for 4 h at ambient temperature. The solution is diluted with dichloromethane and washed with aqueous sodium hydrogen carbonate solution. After drying over sodium sulphate the solvent is removed and the residue is purified using silica gel (cyclohexane).

Yield: 2.6 g (48% of theory) Mass spectrum (EI): m/z=445/447 (Br) [M]⁺

The following compounds are obtained analogously to Example VII:

(1) [4-(3-bromo-benzyl)-phenylethynyl]-triisopropyl-silane

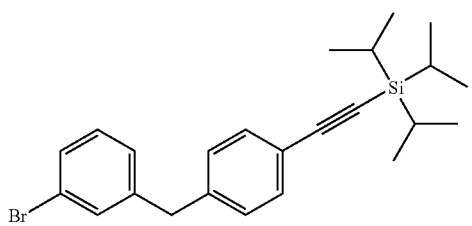

Mass spectrum (ESI⁺): m/z=427/429 (Br) [M+H]⁺

(2) [4-(5-bromo-2-methoxy-benzyl)-phenylethynyl]-triisopropyl-silane

In a departure from the process described hereinbefore the reaction solution is stirred in the ice bath instead of at ambient temperature until the reaction is complete.

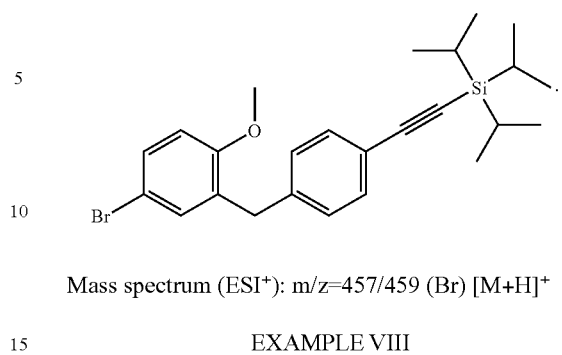

Mass spectrum (ESI⁺): m/z=457/459 (Br) [M+H]⁺

EXAMPLE VIII

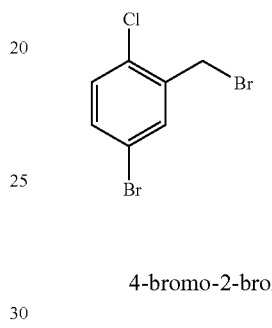

4-bromo-2-brommethyl-1-chloro-benzene 4.0 g N-bromosuccinimide are slowly added to a solution of 5.0 g of 4-bromo-1-chloro-2-hydroxymethyl-benzene and 5.9 g triphenylphosphine in 50 ml of tetrahydrofuran chilled to 5° C. After 1 h stirring at ambient temperature the precipitate is filtered off and the solvent is eliminated in vacuo. The residue is purified through silica gel (cyclohexane/ethyl acetate 50:1).

Yield: 4.9 g (76% of theory) Mass spectrum (EI): m/z=282/284/286 (Br+Cl) [M]⁺

EXAMPLE IX

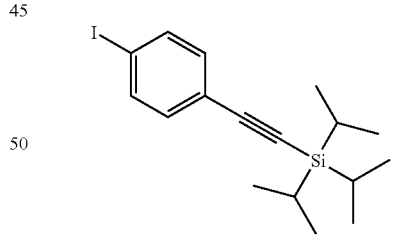

(4-iodo-Phenylethynyl)-triisopropyl-silane

Under argon 18.0 g sodium iodide (dry), 0.6 g copper iodide and 0.8 g N,N'-dimethyl-cyclohexane-1,2-diamine are added to a solution of 20.0 g (4-bromo-phenylethynyl)-triisopropyl-silane. The solution is refluxed with stirring for 24 h and then cooled to ambient temperature. 1% ammonia solution (100 ml) is added and the mixture is extracted with ethyl acetate. After drying over sodium sulphate the solvent is removed and the residue is purified using silica gel (cyclohexane).

Yield: 21.0 g (92% of theory) Mass spectrum (EI): m/z=384 [M]⁺

EXAMPLE X

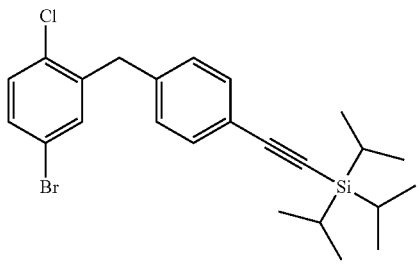

[4-(5-bromo-2-chloro-benzyl)-phenylethynyl]-triiso-propyl-silane

Under argon 0.66 ml of a 2 M solution of isopropylmagnesium chloride in tetrahydrofuran are added dropwise to a solution of 0.50 g (4-iodo-phenylethynyl)-triisopropyl-silane in 2.2 ml dry tetrahydrofuran chilled to −25° C. The solution is stirred for 30 min at −25° C. and then combined with 0.26 ml of a 1 M solution of CuCN*2 LiCl in tetrahydrofuran (prepared by dissolving CuCN and LiCl in the ratio 1:2). Shortly afterwards, 0.35 g 4-bromo-2-bromomethyl-1-chlorbenzene are added and the reaction mixture is brought up to −5° C. in the cooling bath. After 6 h stirring at −5° C. the solution is heated to ambient temperature and stirred overnight. Then a mixture of saturated ammonium chloride solution and 25% ammonia solution (9:1) is added and the resulting mixture is added to water. The organic phase is separated off and the aqueous phase is extracted with ethyl acetate, the combined organic phases are dried over sodium sulphate, and the solvent is removed. The residue is purified through silica gel (cyclohexane).

Yield: 0.28 g (50% of theory) Mass spectrum (EI): m/z=461/463/465 (Br+Cl) [M+H]⁺

EXAMPLE XI

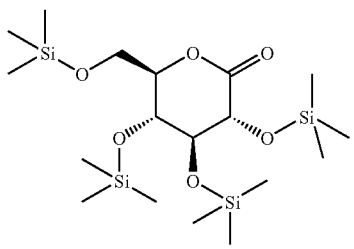

2,3,4,6-tetrakis-O-(trimethylsilyl)-D-glucopyranone

A solution of 20 g D-glucono-1,5-lactone and 98.5 ml N-methylmorpholine in 200 ml of tetrahydrofuran is cooled to −5° C. Then 85 ml trimethylsilylchloride are added dropwise so that the temperature does not exceed 5° C. The solution is then stirred for 1 h at ambient temperature, 5 h at 35° C. and again for 14 h at ambient temperature. After the addition of 300 ml of toluene the solution is cooled in the ice bath, and 500 ml of water are added so that the temperature does not exceed 10° C. The organic phase is then separated off and washed in each case once with aqueous sodium dihydrogen phosphate solution, water and saturated aqueous sodium chloride solution. The solvent is removed, the residue is taken up in 250 ml of toluene and the solvent is again removed completely.

Yield: 52.5 g (approx. 90% pure) Mass spectrum (ESI⁺): m/z=467 [M+H]⁺

EXAMPLE XII

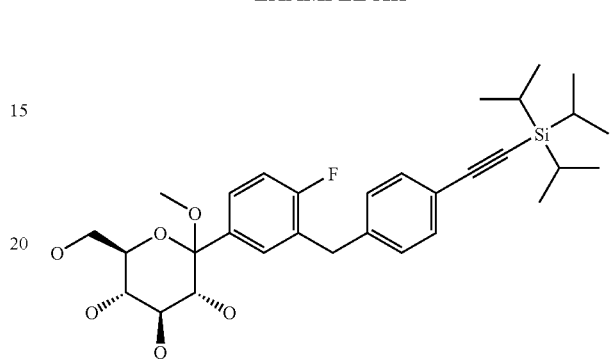

1-fluoro-4-(1-methoxy-D-glucopyranos-1-yl)-2-(4-triisopropylsilylethynyl-benzyl)-benzene A solution of 4.46 g [4-(5-bromo-2-fluoro-benzyl)-phenylethynyl]-triisopropyl-silane in 30 ml dry diethyl ether is cooled to −80° C. under argon. 11.8 ml of a 1.7 M solution of tert-butyllithium in pentane are slowly added dropwise to the cooled solution, and then the solution is stirred for 45 min at −80° C. Then a solution of 5.19 g of 2,3,4,6-tetrakis-O-(trimethylsilyl)-D-glucopyranone in 50 ml diethyl ether, chilled to −80° C., is added dropwise to this solution through a transfer needle. The resulting solution is stirred for 3 h at −78° C. Then a solution of 1.7 ml methanesulphonic acid in 50 ml of methanol is added, the cooling bath is removed and the solution is stirred for 16 h at ambient temperature. The solution is then neutralised with ethyldiisopropylamine and evaporated down to dryness. The residue is purified through silica gel (dichloromethane/methanol 50:1->4:1).

Yield: 2.8 g (50% of theory) Mass spectrum (ESI⁺): m/z=576 [M+NH₄]⁺

The following compounds are obtained analogously to Example XII:

(1) 1-methoxy-4-(1-methoxy-D-glucopyranos-1-yl)-2-(4-triisopropylsilylethynyl-benzyl )-benzene Advantageously the reaction mixture is mixed with only a small excess of methanesulphonic acid.

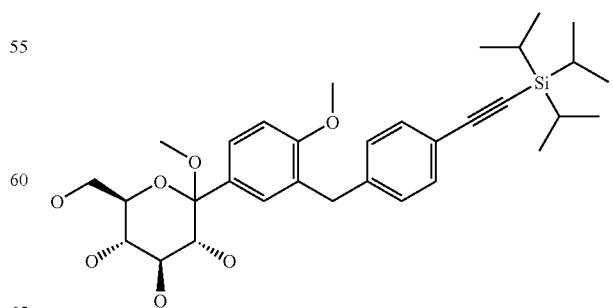

Mass spectrum (ESI⁺): m/z=588 [M+NH₄]⁺

(2) 1-chloro-4-(1-methoxy-D-glucopyranos-1-yl)-2-(4-tri-isopropylsilylethynyl-benzyl)-benzene

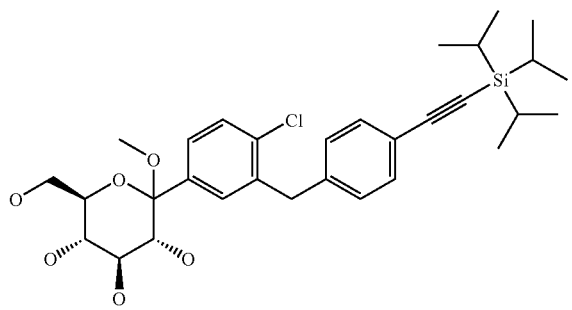

Mass spectrum (ESI⁺): m/z=592/594 (Cl) [M+NH₄]⁺

EXAMPLE XIII

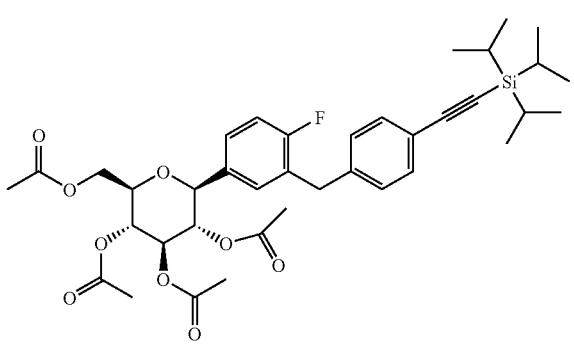

1-fluoro-4-(2,3,4,6-tetra-O-acetyl-β-D-glucopyranos-1-yl)-2-(4-triisopropylsilylethynyl-benzyl)-benzene A solution of 0.8 g 1-fluoro-4-(1-methoxy-D-glucopyranos-1-yl)-2-(4-triisopropylsilylethynyl-benzyl)-benzene and 0.5 ml triethylsilane in 6 ml dichloromethane and 10 ml acetonitrile is cooled to −10° C. 0.27 ml boron trifluoride etherate are added dropwise to the cooled solution. The solution is then stirred for 3 h in the ice bath. Aqueous sodium hydrogen carbonate solution is added to the solution and then the mixture is extracted with ethyl acetate. The organic phase is dried over sodium sulphate, the solvent is removed and the residue is taken up in 6 ml dichloromethane. Then 1.2 ml of pyridine, 1.3 ml of acetic anhydride and 8 mg of 4-dimethylaminopyridine are added. The solution is stirred for 1 h at ambient temperature and then combined with water. The mixture is extracted with dichloromethane, the organic phase is washed with 1 M hydrochloric acid and dried over sodium sulphate. After the solvent has been eliminated the residue is chromatographed through silica gel (cyclohexane/ethyl acetate 4:1->1:1).

Yield: 0.23 g (23% of theory) Mass spectrum (ESI⁺): m/z=714 [M+NH₄]⁺

The following compounds are obtained analogously to Example XIII:

(1) 1-methoxy-4-(2,3,4,6-tetra-O-acetyl-β-D-glucopyranos-1-yl)-2-(4-triisopropylsilylethynyl-benzyl)-benzene

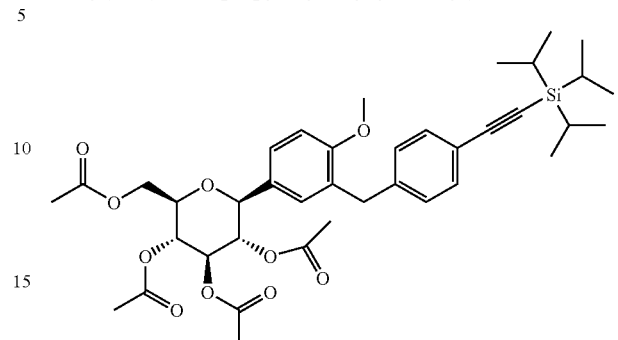

Mass spectrum (ESI⁺): m/z=726 [M+NH₄]⁺

(2) 1-chloro-4-(2,3,4,6-tetra-O-acetyl-β-D-glucopyranos-1-yl)-2-(4-triisopropylsilylethynyl-benzyl)-benzene

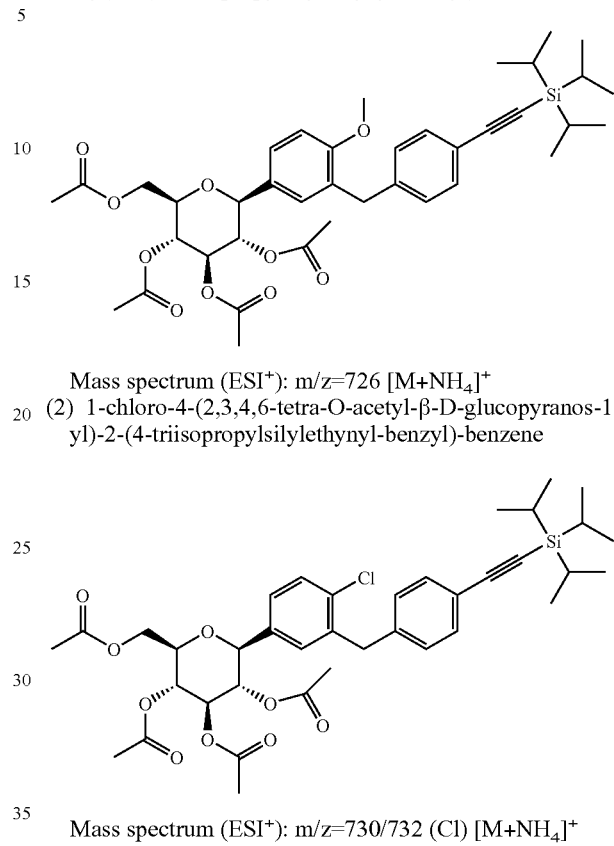

Mass spectrum (ESI⁺): m/z=730/732 (Cl) [M+NH₄]⁺

EXAMPLE XIV

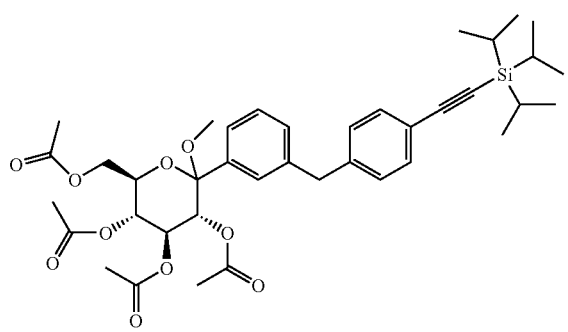

1-(2,3,4,6-Tetra-O-acetyl-1-methoxy-D-glucopyranos-1-yl)-3-(4-triisopropylsilylethynyl-benzyl)-benzene A solution of 2.6 g [4-(3-bromo-benzyl)-phenylethynyl]-triisopropyl-silane in 20 ml dry diethyl ether is cooled to −80° C. under argon. 7.9 ml of a 1.7 M solution of tert-butyllithium in pentane are slowly added dropwise to the cooled solution, and then the solution is stirred for 30 min at −80° C. A solution of 3.2 g 2,3,4,6-tetrakis-O-(trimethylsilyl)-D-glucopyranone in 30 ml diethyl ether chilled to −80° C. is then added dropwise to this solution through a transfer needle. The resulting solution is stirred for 2 h at −78° C. and then another solution of 1.0 g g 2,3,4,6-tetrakis-O-(trimethylsilyl)-D-glucopyranone in 10 ml diethyl ether chilled to −80° C. is added dropwise. After another hour's stirring at −78° C. a solution of 2 ml methanesulphonic acid in 20 ml of methanol is added, the cooling bath is removed and the solution is stirred for 16 h at ambient temperature. The solution is then neutralised with ethyldiisopropylamine, the solvent is removed completely and the residue is taken up in 50 ml of toluene. 8.5 ml ethyldiisopropylamine are added, and the solution is cooled in the ice bath. Then 4.3 ml acetic anhydride and 0,15 g 4-dimethylaminopyridine are added. The solution is stirred for 2 h at ambient temperature and then combined with aqueous sodium hydrogen carbonate solution. It is extracted with ethyl acetate, the organic phases are dried over sodium sulphate, and the solvent is removed. The residue is chromatographed through silica gel (cyclohexane/ethyl acetate 4:1−>1:3).

Yield: 2.0 g (46% of theory) Mass spectrum (ESI$^+$): m/z=726 [M+NH$_4$]$^+$

The following compound is obtained analogously to Example XIV:

(1) 1-(triisopropylsilylethynyl)-4-(2,3,4,6-tetra-O-acetyl-1-methoxy-D-glucopyranos-1-yl)-2-(4-ethoxy-benzyl)-benzene

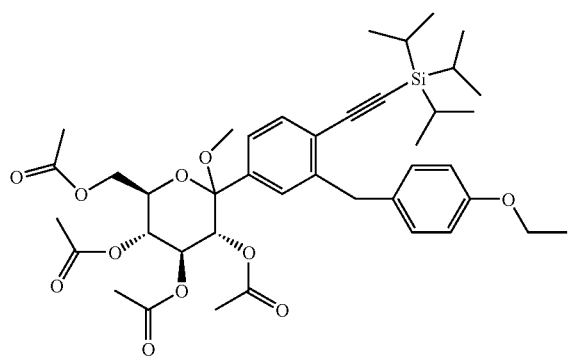

Mass spectrum (ESI$^+$): m/z=770 [M+NH$_4$]$^+$

EXAMPLE XV

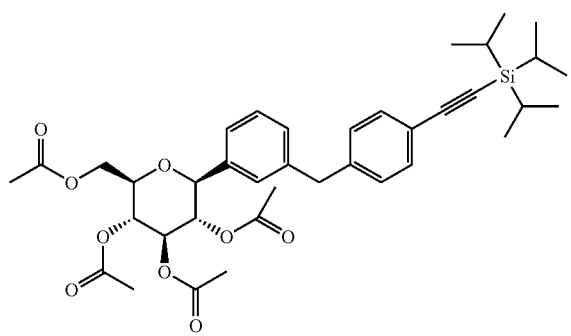

1-(2,3,4,6-Tetra-O-acetyl-β-D-glucopyranos-1-yl)-3-(4-triisopropylsilylethynyl-benzyl)-benzene 1.2 ml triethylsilane and 0.36 ml boron trifluoride etherate are added dropwise to an ice-cooled solution of 1.0 g 1-(2,3,4,6-tetra-O-acetyl-1-methoxy-D-glucopyranos-1-yl)-3-(4-triisopropylsilylethynyl-benzyl)-benzene and 25 µl water in 10 ml acetonitrile. The solution is then stirred for 3 h in the ice bath and for 1 h at ambient temperature. Then the solution is again cooled in the ice bath, and another 1.2 ml triethylsilane and 0.36 ml boron trifluoride etherate are added. The solution is stirred for a further 0.5 h in the ice bath and 2 h at ambient temperature. Aqueous sodium hydrogen carbonate solution is then added to the solution, and the resulting solution is extracted with ethyl acetate. The organic phase is dried over sodium sulphate and the solvent is removed.

Yield: 0.78 g (81% of theory) Mass spectrum (ESI$^+$): m/z=696 [M+NH$_4$]$^+$

The following compound is obtained analogously to Example XV:

(1) 1-(triisopropylsilylethynyl)-4-(2,3,4,6-tetra-O-acetyl-β-D-glucopyranos-1-yl)-2-(4-ethoxy-benzyl)-benzene

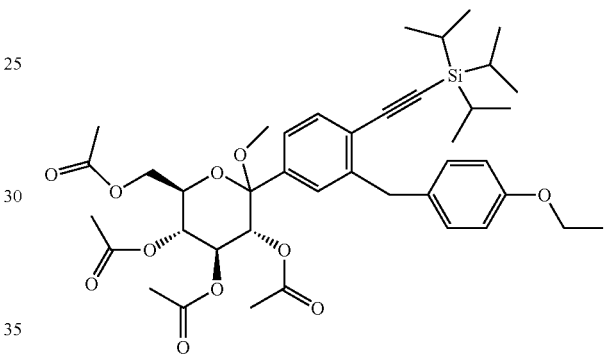

EXAMPLE XVI

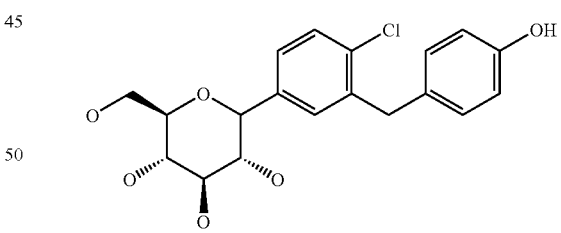

1-chloro-4-(β-D-glucopyranos-1-yl)-2-(4-hydroxy-benzyl)-benzene

A solution of 4.0 g [4-(5-bromo-2-chloro-benzyl)-phenoxy]-tert-butyl-dimethyl-silane in 42 ml dry diethyl ether is cooled to −80° C. under argon. 11.6 ml of a 1.7 M solution of tert-butyllithium in pentane are slowly added dropwise to the cooled solution, and then the solution is stirred for 30 min at −80° C. This solution is then added dropwise through a transfer needle, which is cooled with dry ice, to a solution of 4.78 g 2,3,4,6-tetrakis-O-(trimethylsilyl)-D-glucopyranone in 38 ml diethyl ether chilled to −80° C. The resulting solution is stirred for 3 h at −78° C. Then a solution of 1.1 ml methanesulphonic acid in 35 ml of methanol is added and the solution is stirred for 16 h at ambient temperature. The solution is then neutralised with solid sodium hydrogen carbonate, ethyl acetate is added and the methanol is removed together with the ether. Aqueous sodium hydrogen carbonate solution is added to the remaining solution and extracted four times with ethyl acetate. The organic phases are dried over sodium sulphate and evaporated down. The residue is dissolved in 30 ml acetonitrile and 30 ml dichloromethane and the solution is cooled to −10° C. After the addition of 4.4 ml triethylsilane 2.6 ml boron trifluoride etherate are added dropwise so that the temperature does not exceed −5° C. After the addition has ended the solution is stirred for another 5 h at −5 to −10° C. and then quenched by the addition of aqueous sodium hydrogen carbonate solution. The organic phase is separated off and the aqueous phase is extracted four times with ethyl acetate. The combined organic phase are dried over sodium sulphate, the solvent is removed and the residue is purified using silica gel. The product then obtained is an approx. 6:1 mixture of β/α which can be converted into the pure β-anomer by total acetylation of the hydroxy groups with acetic anhydride and pyridine in dichloromethane and recrystallising the product in ethanol. The product thus obtained is converted into the title compound by reacting in methanol with 4 M potassium hydroxide solution.

Yield: 1.6 g (46% of theory) Mass spectrum (ESI$^+$): m/z=398/400 (Cl) [M+H]$^+$

EXAMPLE XVII

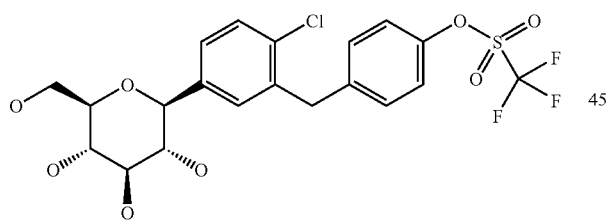

1-chloro-4-(β-D-glucopyranos-1-yl)-2-[4-(trifluoromethylsulphonyloxy)-benzyl]-benzene 10 mg 4-dimethylaminopyridine are added to a solution of 0.38 g 1-chloro-4-(β-D-glucopyranos-1-yl)-2-(4-hydroxybenzyl)-benzene, 0.21 ml triethylamine and 0.39 g N,N-bis-(trifluoromethanesulphonyl)-aniline in 10 ml dry dichloromethane. The solution is stirred for 4 h at ambient temperature and then combined with aqueous sodium chloride solution. It is extracted with ethyl acetate, the organic extracts are dried over sodium sulphate, and the solvent is removed. The residue is chromatographed through silica gel (dichloromethane/methanol 1:0->4:1).

Yield: 0.33 g (64% of theory) Mass spectrum (ESI$^+$): m/z=530/532 (Cl) [M+NH$_4$]$^+$

EXAMPLE XVIII

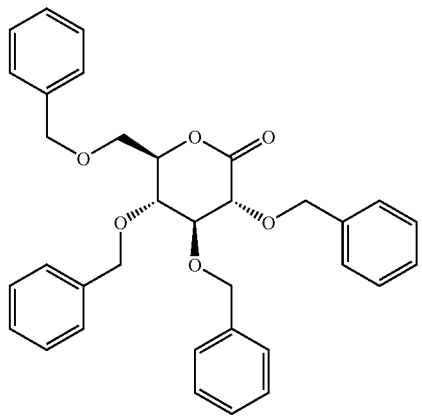

2,3,4,6-Tetra-O-benzyl-D-glucopyranone 4 g freshly activated molecular sieve 4 Å and 3.3 g N-methylmorpholine-N-oxide are added to a solution of 10.0 g 2,3,4,6-tetra-O-benzyl-α-D-glucopyranose in 140 ml dichloromethane. The solution is stirred for 20 min at ambient temperature, before adding 0.3 g of tetrapropylammonium perruthenate. After 2 h stirring at ambient temperature the solution is diluted with dichloromethane and filtered through Celite. The filtrate is washed with aqueous sodium thiosulphate solution and water and then dried over sodium sulphate. After the solvent has been eliminated the residue is chromatographed through silica gel (cyclohexane/ethyl acetate 4:1).

Yield: 8.2 g (82% of theory) Mass spectrum (ESI$^+$): m/z=539 [M+H]$^+$

EXAMPLE XIX

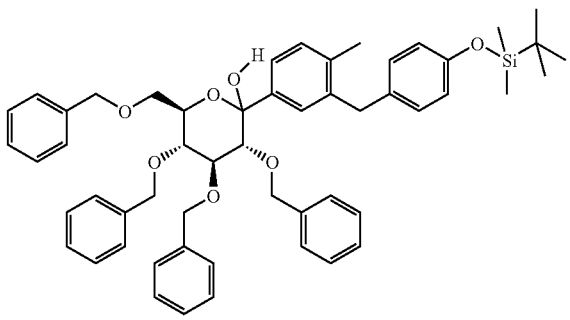

1-(2,3,4,6-Tetra-O-benzyl-1-hydroxy-D-glucopyranos-1-yl)-3-[4-(tert-butyl-dimethyl-silyloxy)-benzyl]-4-methyl-benzene A solution of 0.34 g [4-(5-bromo-2-methyl-benzyl)-phenoxy]-tert-butyl-dimethyl-silane in 3 ml dry tetrahydrofuran is cooled to −80° C. under argon. 0.54 ml of a 1.6 M solution of n-butyllithium in hexane are added dropwise to the cooled solution, and the solution is stirred for 1.5 h at −78° C. A solution of 0.43 g 2,3,4,6-tetra-O-benzyl-D-glucopyranone in 2.5 ml of tetrahydrofuran chilled to −80° C. is added dropwise to this solution by means of transfer needle. The resulting solution is stirred for 5 h at −78° C. The reaction is quenched with a solution of 0.1 ml acetic acid in 1 ml of tetrahydrofuran and heated to ambient temperature. Then aqueous sodium hydrogen carbonate solution is added and the mixture is extracted four times with ethyl acetate. The organic phases are dried over sodium sulphate and evaporated down. The residue is purified by chromatography on silica gel (cyclohexane/ethyl acetate 15:1->4:1).

Yield: 0.48 g (approx. 88% pure) Mass spectrum (ESI$^+$): m/z=868 [M$^+$H]$^+$

EXAMPLE XX

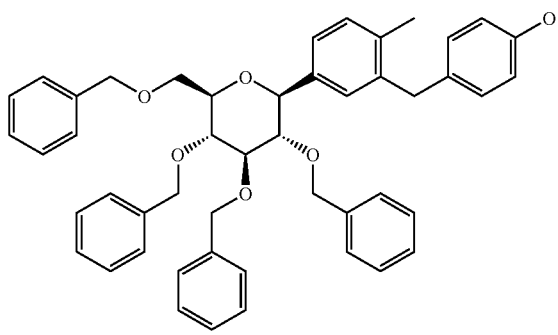

1-(2,3,4,6-tetra-O-benzyl-β-D-glucopyranos-1-yl)-3-(4-hydroxy-benzyl)-4-methyl-benzene A solution of 0.48 g (approx. 88% pure) 1-(2,3,4,6-tetra-O-benzyl-1-hydroxy-D-glucopyranosyl)-3-[4-(tert-butyl-dimethyl-silyloxy)-benzyl]-4-methyl-benzene in 3.5 ml dry acetonitrile is cooled to −40° C. under argon. 0.13 ml triisopropylsilane and 0.08 ml boron trifluoride etherate are added dropwise to the cooled solution. The solution is stirred for 3 h at −35° C., before another 0.02 ml of triisopropylsilane and 0.01 ml of boron trifluoride etherate are added. After a further 2 h at −40° C. aqueous potassium carbonate is added and the solution is stirred for 1 h at ambient temperature. Then it is diluted with water and extracted four times with ethyl acetate. The organic phase is dried over sodium sulphate, concentrated and chromatographed through silica gel (cyclohexane/ethyl acetate 10:1->4:1).

Yield: 0.24 g (68% of theory). Mass spectrum (ESI$^+$): m/z 738 [M+NH$_4$]$^+$

EXAMPLE XXI

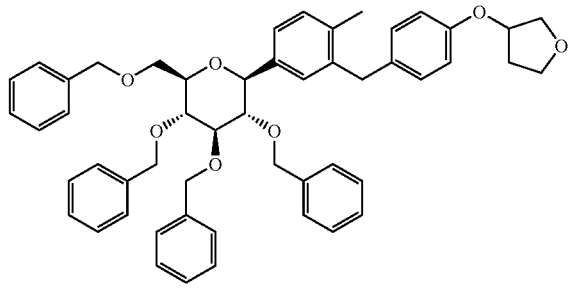

1-(2,3,4,6-tetra-O-benzyl-(β-D-glucopyranos-1-yl)-3-[4-(tetrahydrofuran-3-yloxy)-benzyl]-4-methyl-benzene 0.10 g tetrahydrofuran-3-yl toluene-4-sulphonate are added to a mixture of 0.24 g 1-(2,3,4,6-tetra-O-benzyl-(β-D-glucopyranos-1-yl)-3-(4-hydroxy-benzyl)-4-methyl-benzene and 0.13 g caesium carbonate in 2.5 ml of dimethylformamide. The mixture is stirred for 4 h at 65° C., before water is added. It is extracted three times with ethyl acetate, the organic phase is dried over sodium sulphate and the solvent is removed. The residue is purified through silica gel purified (cyclohexane/ethyl acetate 10:1->4:1).

Yield: 0.23 g (78% of theory). Mass spectrum (ESI$^+$): m/z=808 [M+H]$^+$

EXAMPLE XXII

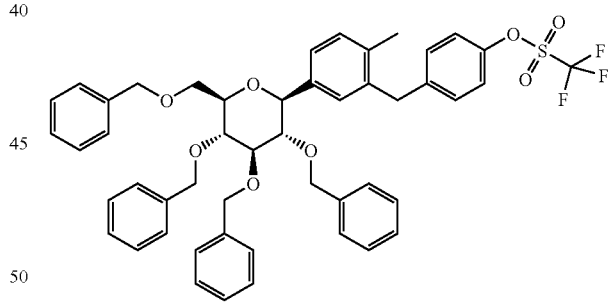

1-(2,3,4,6-tetra-O-benzyl-β-D-glucopyranos-1-yl)-3-[4-(trifluoromethylsulphonyloxy)-benzyl]-4-methyl-benzene A solution of 0.62 g 1-(2,3,4,6-tetra-O-benzyl-β-D-glucopyranos-1-yl)-3-(4-hydroxy-benzyl)-4-methyl-benzene in 4.5 ml dry dichloromethane is cooled to −10° C. under argon. 0.14 ml of pyridine and a solution of 0.3 g trifluoromethanesulphonic anhydride in 0.5 ml dichloromethane are added to the cooled solution. The solution is stirred for 0.5 h at −5 to −10° C., before aqueous sodium hydrogen carbonate solution is added. The mixture is extracted three times with dichloromethane, the combined organic phases are washed with aqueous 1 M hydrochloric acid and dried over sodium sulphate. After the solvent has been eliminated the residue is chromatographed through silica gel (cyclohexane/ethyl acetate 15:1->7:1).

Yield: 0.62 g (84% of theory) Mass spectrum (ESI⁺): m/z=853 [M+H]⁺

EXAMPLE XXIII

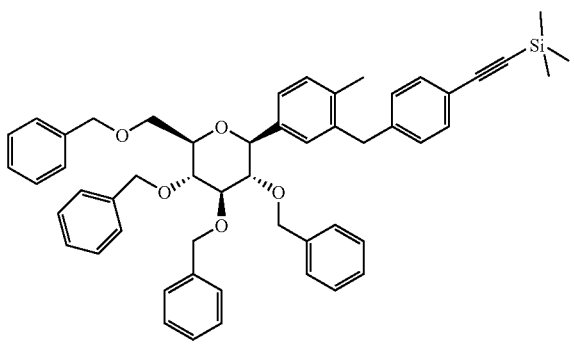

1-(2,3,4,6-tetra-O-benzyl-β-D-glucopyranos-1-yl)-3-[4-(trimethylsilylethynyl)-benzyl]-4-methyl-benzene Under argon, 27 mg copper iodide, 49 mg bis-(triphenylphosphine)-palladium dichloride, 0.30 ml triethylamine and finally 0.14 ml of trimethylsilylacetylene are added to a solution of 0.60 g 1-(2,3,4,6-tetra-O-benzyl-β-D-glucopyranos-1-yl)-3-[4-(trifluoromethylsulphonyloxy)-benzyl]-4-methyl-benzene in 3 ml of dimethylformamide. The flask is tightly sealed and stirred for 4 h at 90° C. Then another 20 mg of bis-(triphenylphosphine)-palladium dichloride and 0.6 ml trimethylsilylacetylene are added, and the solution is stirred for a further 4 h at 90° C. Then aqueous sodium hydrogen carbonate solution is added, the mixture is extracted three times with ethyl acetate, and the combined organic phases are dried over sodium sulphate. After the solvent has been eliminated the residue is chromatographed through silica gel (cyclohexane/ethyl acetate 40:1->10:1).

Yield: 0.45 g (80% of theory) Mass spectrum (ESI⁺): m/z=818 [M+NH₄]⁺

Preparation of the End Compounds:

EXAMPLE 1

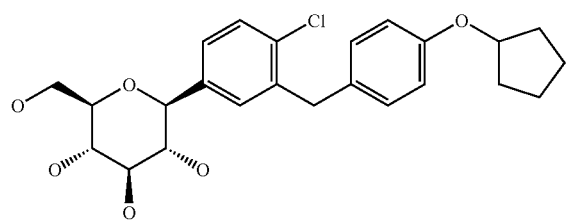

1-chloro-2-(4-cyclopentyloxybenzyl)-4-(β-D-glucopyranos-1-yl)-benzene 0.16 ml iodocyclopentane are added to a mixture of 0.25 g 1-chloro-4-(β-D-glucopyranos-1-yl)-2-(4-hydroxybenzyl)-benzene and 0.4 g caesium carbonate in 2.5 ml of dimethylformamide. The mixture is stirred for 4 h at 45° C., before another 0.1 g caesium carbonate and 0.05 ml iodocyclopentane are added. After another 14 h stirring at 45° C. aqueous sodium chloride solution is added and the mixture is extracted with ethyl acetate. The organic phase is dried over sodium sulphate, the solvent is removed and the residue is purified using silica gel (dichloromethane/methanol 1:0->5:1).

Yield: 0.23 g (78% of theory) Mass spectrum (ESI⁺): m/z=466/468 (Cl) [M+NH₄]⁺

The following compounds are obtained analogously to Example 1:

(2) 1-chloro-4-(β-D-glucopyranos-1-yl)-2-[4-((R)-tetrahydrofuran-3-yloxy)-benzyl]-benzene The reaction is carried out with tetrahydrofuran-3-yl (S)-toluene-4-sulphonate as the coupling partner.

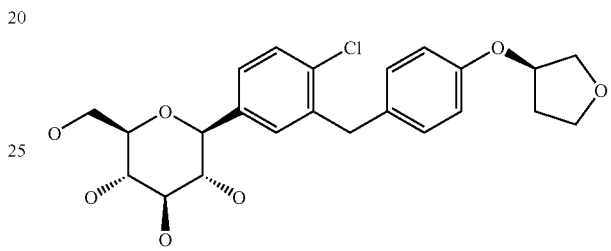

Mass spectrum (ESI⁺): m/z=451/453 (Cl) [M+H]+

(3) 1-chloro-4-(β-D-glucopyranos-1-yl)-2-[4-((S)-tetrahydrofuran-3-yloxy)-benzyl]-benzene The reaction is carried out with tetrahydrofuran-3-yl (R)-toluene-4-sulphonate as the coupling partner.

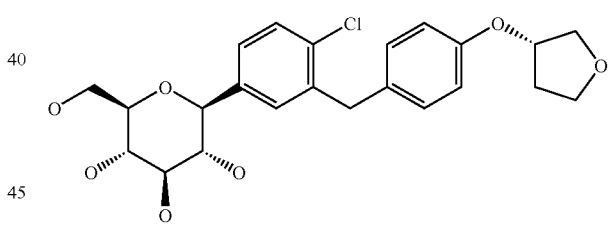

Mass spectrum (ESI⁺): m/z=451/453 (Cl) [M+H]⁺

(4) 1-chloro-4-(β-D-glucopyranos-1-yl)-2-[4-(tetrahydrofuran-2-on-3-yloxy)-benzyl]-benzene The reaction is carried out with 3-bromobutyrolactone as the coupling partner.

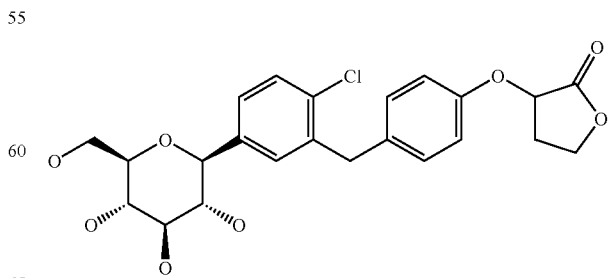

Mass spectrum (ESI⁺): m/z=465/467 (Cl) [M+H]⁺

(5) 1-chloro-4-(β-D-glucopyranos-1-yl)-2-(4-cyclobutyloxy-benzyl)-benzene

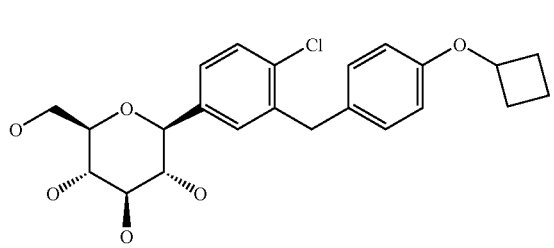

Mass spectrum (ESI⁺): m/z=452/454 (Cl) [M+NH₄]⁺

(6) 1-chloro-4-(β-D-glucopyranos-1-yl)-2-(4-cyclohexyloxy-benzyl)-benzene

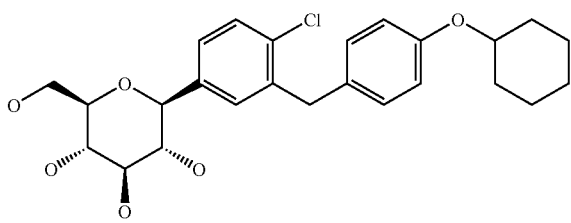

Mass spectrum (ESI⁺): m/z=480/482 (Cl) [M+NH₄]⁺

(7) 1-chloro-4-(β-D-glucopyranos-1-yl)-2-[4-(tetrahydropyran-4-yloxy)-benzyl]-benzene

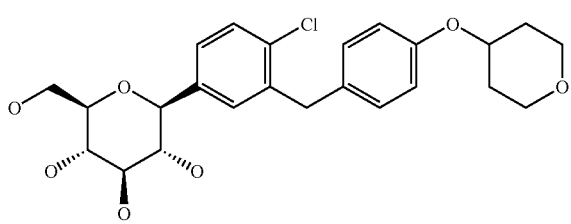

Mass spectrum (ESI⁺): m/z=487/489 (Cl) [M+Na]⁺

(8) 1-chloro-4-(β-D-glucopyranos-1-yl)-2-[4-(1-acetyl-piperidin-4-yloxy)-benzyl]-benzene The reaction is carried out with 1-acetyl-4-methylsulphonyloxy-piperidine as the electrophile.

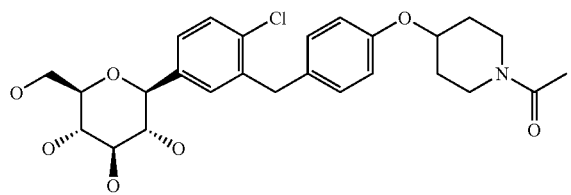

Mass spectrum (ESI⁺): m/z=506/508 (Cl) [M+H]⁺

(9) 1-chloro-4-(β-D-glucopyranos-1-yl)-2-[4-(1-tert-butyloxycarbonylpiperidin-4-yloxy)-benzyl]-benzene The reaction is carried out with 1-tert-butyloxycarbonyl-4-methylsulphonyloxy-piperidine as the electrophile.

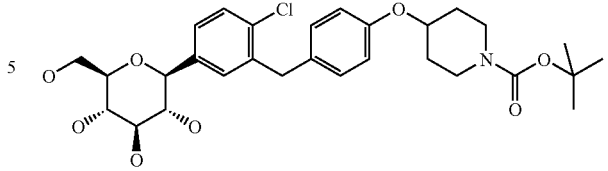

Mass spectrum (ESI⁺): m/z=586/588 (Cl) [M+Na]⁺

EXAMPLE 10

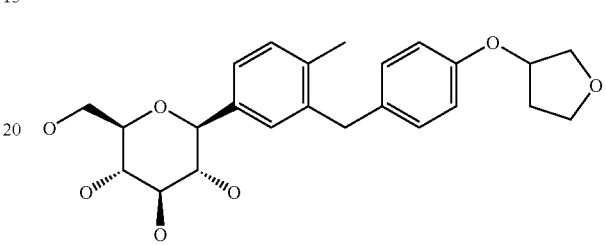

1-(β-D-glucopyranos-1-yl)-4-methyl-3-[4-(tetrahydrofuran-3-yloxy)-benzyl]-benzene A mixture of 0.21 g 1-(2,3,4,6-tetra-O-benzyl-(β-D-glucopyranos-1-yl)-3-[4-(tetrahydrofuran-3-ylox)-benzyl]-4-methyl-benzene and 0.1 g of 10% palladium hydroxide on charcoal in 3 ml of ethyl acetate is shaken for 24 h at ambient temperature under a hydrogen pressure of 1 atm. Then the same amount of catalyst is added again and the mixture is shaken for a further 24 h under a hydrogen atmosphere. Then the catalyst is filtered off, the filtrate is evaporated down and the residue is chromatographed through silica gel (dichloromethane/methanol 1:0->5:1).

Yield: 0.06 g (49% of theory) Mass spectrum (ESI⁺): m/z=448 [M+NH₄]⁺

EXAMPLE 11

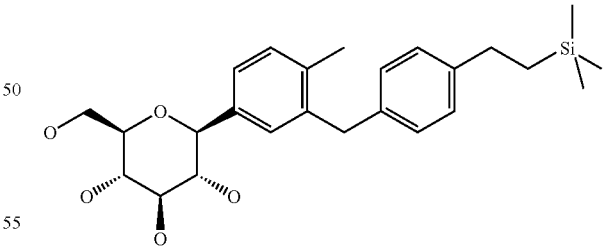

1-(β-D-glucopyranos-1-yl)-4-methyl-3-[4-(2-trimethylsilyl-ethyl)-benzyl]-benzene A mixture of 0.29 g 1-(2,3,4,6-tetra-O-benzyl-β-D-glucopyranos-1-yl)₄-methyl-3-[4-(trimethylsilylethynyl)-benzyl]-benzene and 0.25 g of 10% palladium hydroxide on charcoal in 3 ml of ethyl acetate is shaken for 24 h at ambient temperature under a hydrogen pressure of 1 atm. Then another 0.2 g of catalyst are added and the solution is shaken for a further 20 h under a hydrogen atmosphere. Then the catalyst is filtered off, the filtrate is evaporated down and the residue is chromatographed through silica gel (dichloromethane/methanol 1:0->5:1).

Yield: 0.08 g (51% of theory) Mass spectrum (ESI⁺): m/z=462 [M+NH$_4$]$^+$

EXAMPLE 12

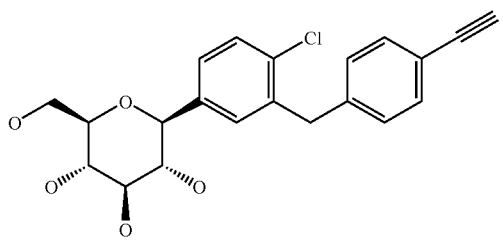

1-chloro-4-(β-D-glucopyranos-1-yl)-2-(4-ethynyl-benzyl)-benzene 25 mg of copper iodide, 44 mg of bis-(triphenylphosphine)-palladium dichloride, 0.30 ml triethylamine and finally 0.14 ml of trimethylsilylacetylene are added under argon to a solution of 0.32 g 1-chloro-4-(β-D-glucopyranos-1-yl)-2-[4-(trifluoromethylsulphonyloxy)-benzyl]-benzene in 3 ml of dimethylformamide. The flask is tightly sealed and stirred for 8 h at 90° C. Then another 25 mg of bis-(triphenylphosphine)-palladium dichloride and 0.1 ml trimethylsilylacetylene are added, and the solution is stirred for a further 10 h at 90° C. Then aqueous sodium hydrogen carbonate solution is added, the mixture is extracted three times with ethyl acetate, and the combined organic phases are dried over sodium sulphate. After the solvent has been eliminated the residue is dissolved in 5 ml of methanol and combined with 0.12 g potassium carbonate. The mixture is stirred for 1 h at ambient temperature and then neutralised with 1 M hydrochloric acid. Then the methanol is evaporated off, the residue is combined with aqueous sodium chloride solution and extracted with ethyl acetate. The organic extracts collected are dried over sodium sulphate, and the solvent is removed. The residue is chromatographed through silica gel (dichloromethane/methanol 1:0->5:1).

Yield: 0.095 g (40% of theory) Mass spectrum (ESI⁺): m/z=406/408 (Cl) [M+NH$_4$]$^+$ This compound may also be obtained according to Example 14.

EXAMPLE 13

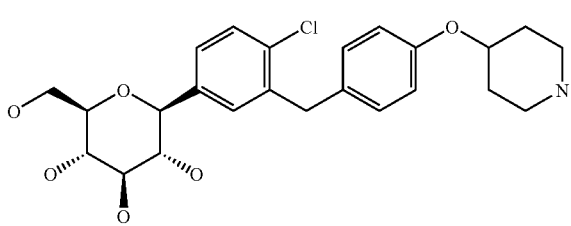

1-chloro-4-(β-D-glucopyranos-1-yl)-2-[4-(piperdin-4-yloxy)-benzyl]-benzene 2 ml trifluoroacetic acid are added to a solution of 0.19 g 1-chloro-4-(β-D-glucopyranos-1-yl)-2-[4-(1-tert-butlyoxycarbonylpiperidin-4-yloxy)-benzyl]-benzene in 4 ml dichloromethane. The solution is stirred for 1.5 h at ambient temperature and then diluted with ethyl acetate and made basic with aqueous potassium carbonate solution. The organic phase is separated off and the aqueous phase is extracted with ethyl acetate. The combined organic phases are dried over sodium sulphate and the solvent is eliminated entirely.

Yield: 0.060 g (38% of theory) Mass spectrum (ESI⁺): m/z=464/466 (Cl) [M+H]$^+$

EXAMPLE 14

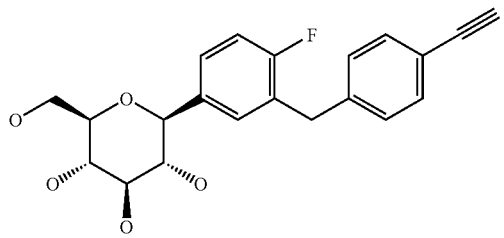

1-fluoro-4-(β-D-glucopyranos-1-yl)-2-(4-ethynyl-benzyl)-benzene 0.33 ml of a 1 M solution of tetrabutylammoniumfluorid in tetrahydrofuran are added to a solution of 0.23 g 1-fluoro-4-(2,3,4,6-tetra-O-acetyl-β-D-glucopyranos-1-yl)-2-(triisopropylsilylethynyl-benzyl)-benzene in 1.5 ml of tetrahydrofuran. The solution is stirred for 1 h at ambient temperature. Then 1 ml of methanol and 1.5 ml of 4 M potassium hydroxide solution are added and the solution is stirred for a further hour at ambient temperature. The solution is neutralised with 1 M hydrochloric acid and then the methanol is evaporated off. The residue is combined with aqueous sodium chloride solution and extracted with ethyl acetate. The organic extracts collected are dried over sodium sulphate, and the solvent is removed. The residue is chromatographed through silica gel (dichloromethane/methanol 19:1->2:1).

Yield: 0.060 g (49% of theory) Mass spectrum (ESI⁺): m/z=390 [M+NH$_4$]$^+$

The following compounds are obtained analogously to Example 14:

(15) 1-(β-D-glucopyranos-1-yl)-3-(4-ethynyl-benzyl)-benzene

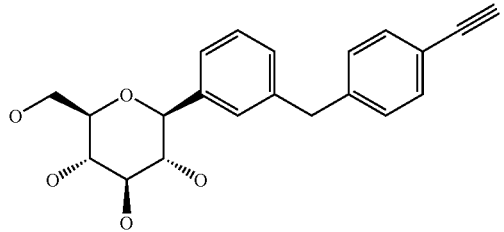

Mass spectrum (ESI⁺): m/z=372 [M+NH$_4$]$^+$

(16) 1-ethynyl-4-(β-D-glucopyranos-1-yl)-2-(4-ethoxy-benzyl)-benzene

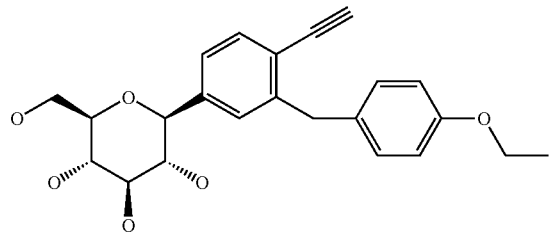

Mass spectrum (ESI⁺): m/z=416 [M+NH$_4$]$^+$

(17) 1-methoxy-4-(β-D-glucopyranos-1-yl)-2-(4-ethynyl-benzyl)-benzene

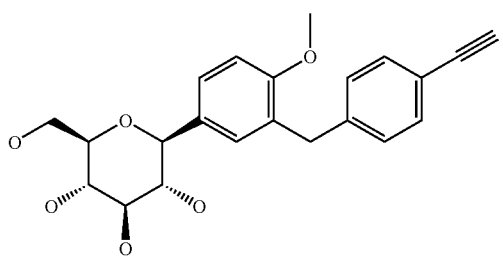

Mass spectrum (ESI⁺): m/z=402 [M+NH$_4$]$^+$

The compound according to Example (12) (1-chloro-4-(β-D-glucopyranos-1-yl)-2-(4-ethynyl-benzyl)-benzene) may also be synthesised analogously to Example 14. Optionally, the intermediate stage, 1-chloro-4-(2,3,4,6-tetra-O-acteyl-β-D-glucopyranos-1-yl)-2-(4-ethynyl-benzyl)-benzene, which is obtained after desilylation with tetrabutylammonium fluoride, may be purified by recrystallisation from ethanol.

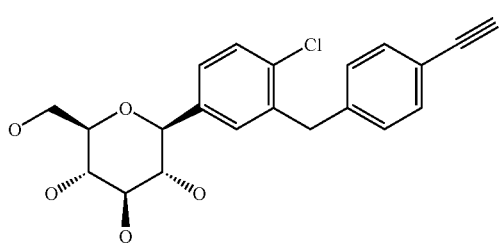

Mass spectrum (ESI⁺): m/z=406/408 (Cl) [M+NH$_4$]$^+$

The following compounds are also prepared analogously to the above-mentioned Examples and other methods known from the literature:

| Ex. | Structure |
|---|---|
| (18) | 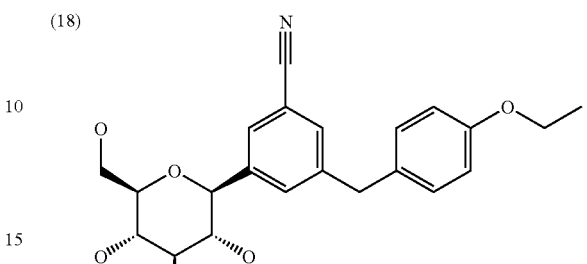 |
| (19) | 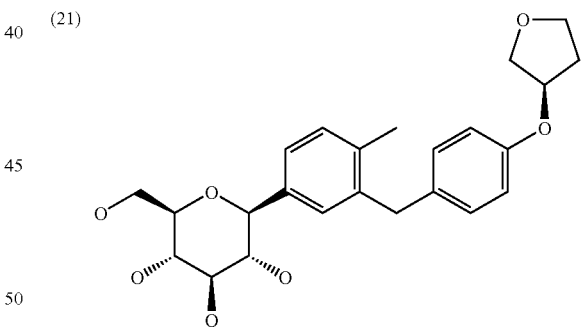 |
| (20) | 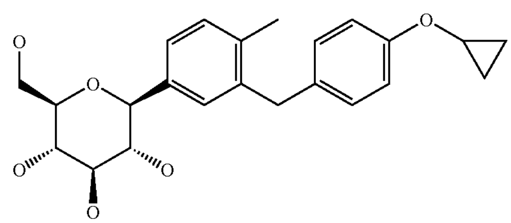 |
| (21) | 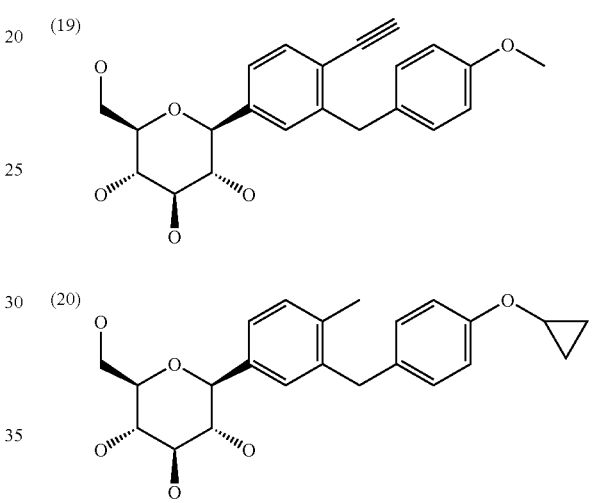 |
| (22) | 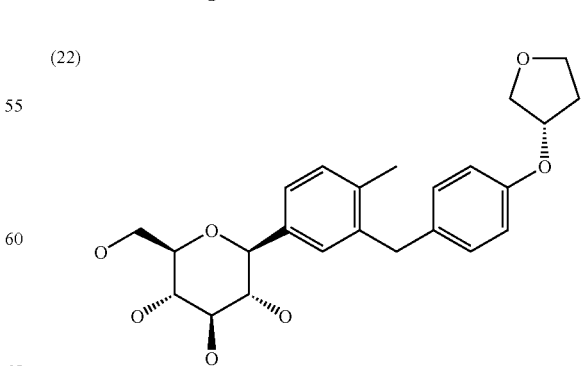 |

-continued
| Ex. | Structure |
|---|---|
| (23) | 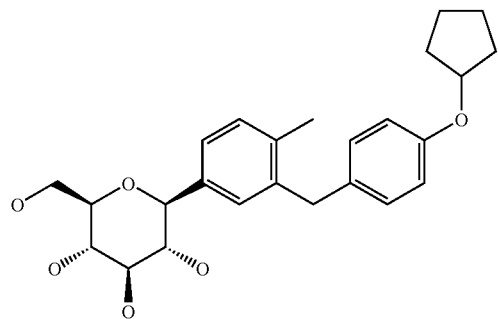 |
| (24) | 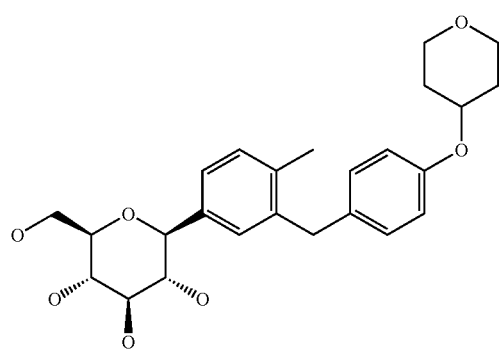 |
| (25) | 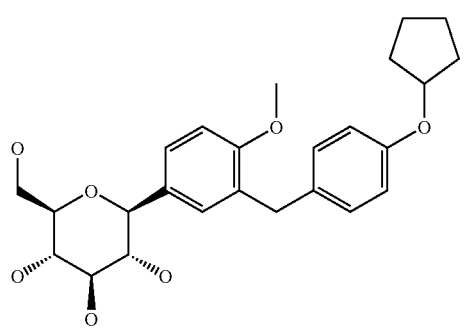 |
| (26) | 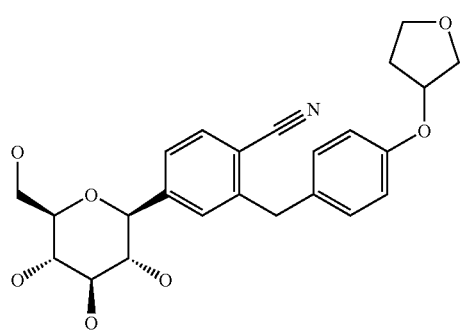 |
-continued
| Ex. | Structure |
|---|---|
| (27) | 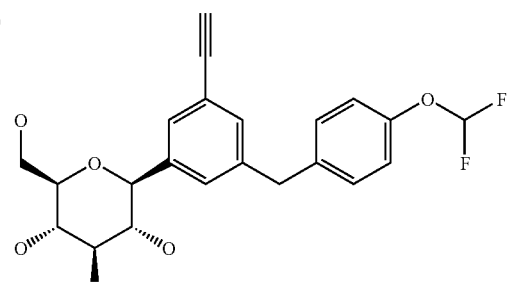 |
| (28) | 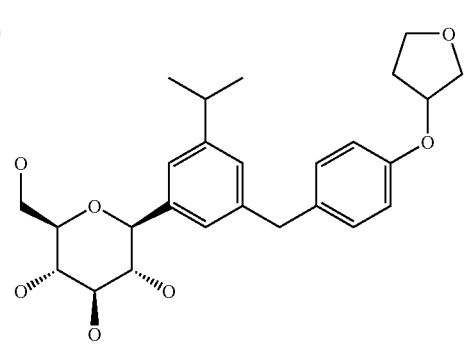 |
| (29) | 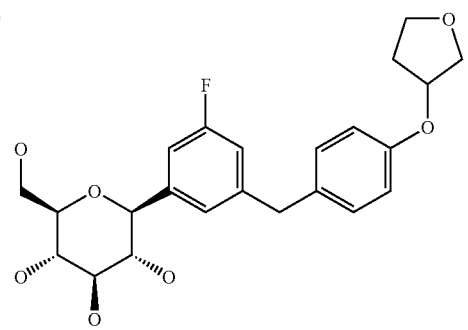 |
| (30) | 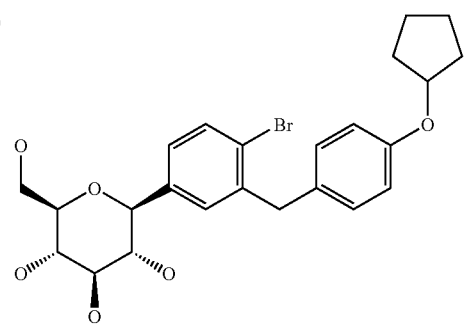 |

| Ex. | Structure |
|---|---|
| (31) | 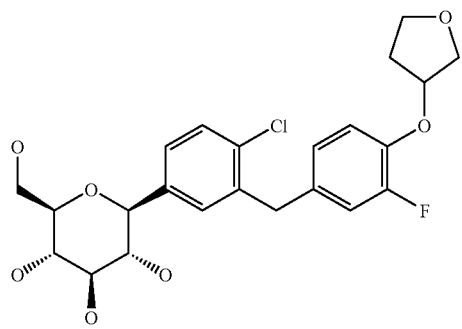 |
| (32) | 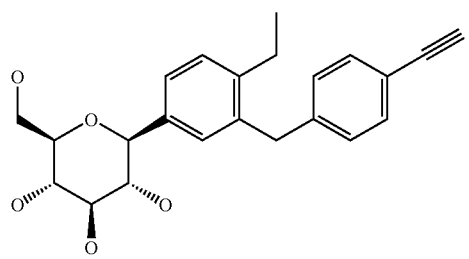 |
| (33) | 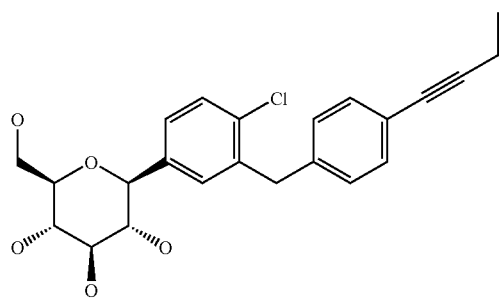 |
| (34) | 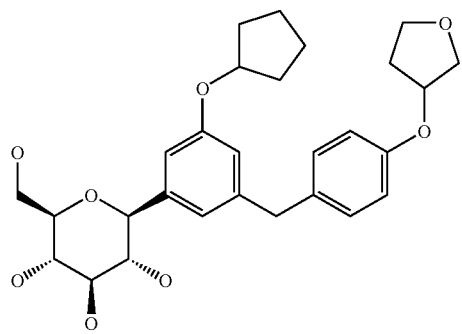 |
| (35) | 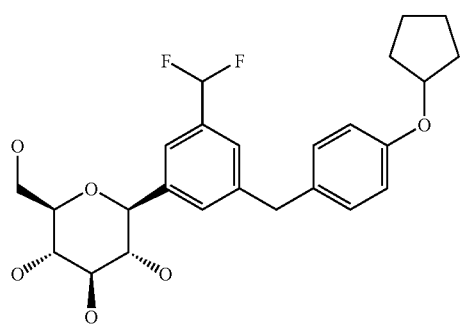 |
| Ex. | Structure |
|---|---|
| (36) | 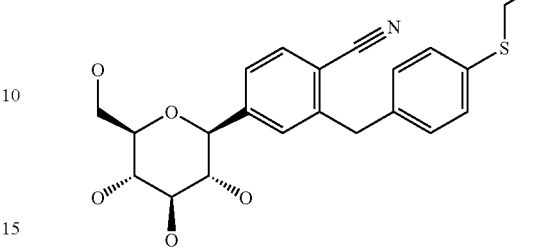 |
| (37) | 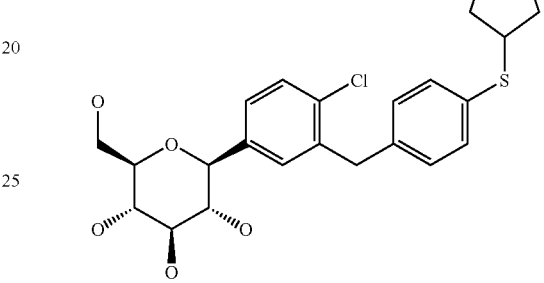 |
| (38) | 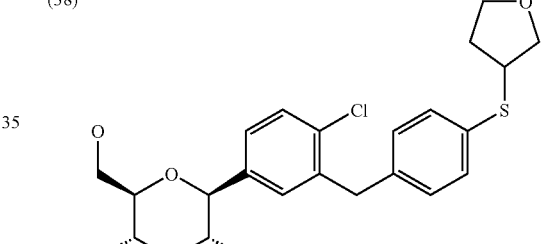 |
| (39) | 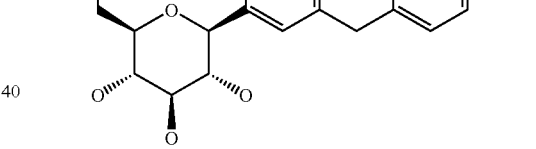 |
| (40) | 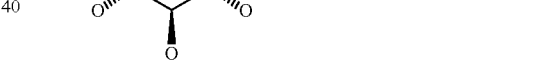 |

-continued
| Ex. | Structure |
|---|---|
| (41) | 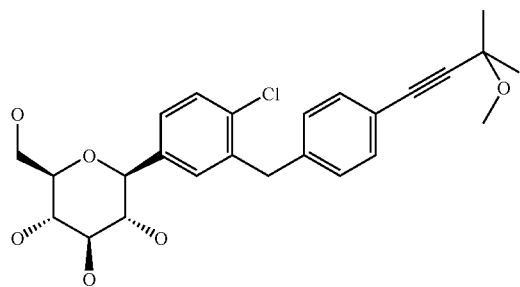 |
| (42) | 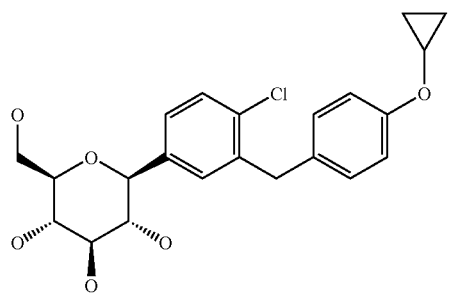 |
| (43) | 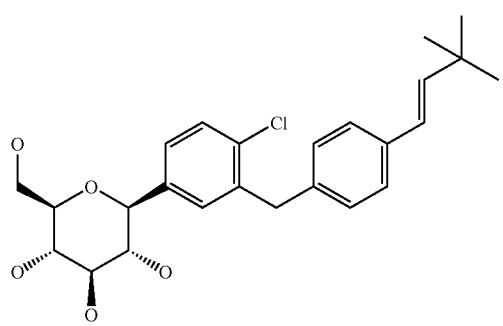 |
| (44) | 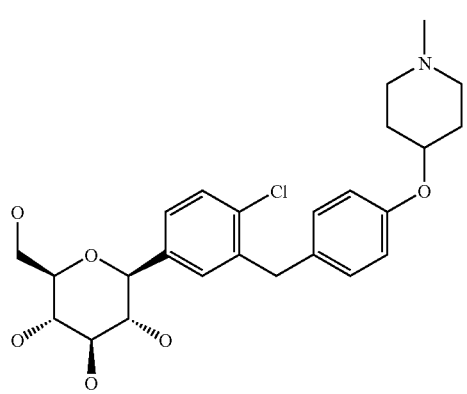 |
| (45) | 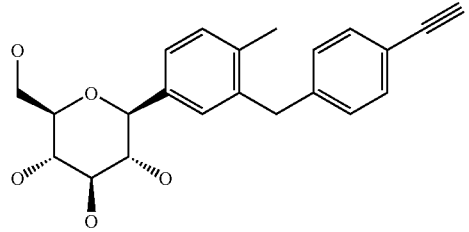 |
-continued
| Ex. | Structure |
|---|---|
| (46) | 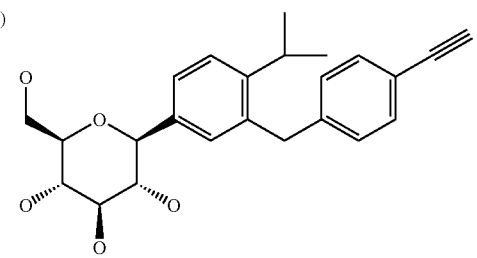 |
| (47) | 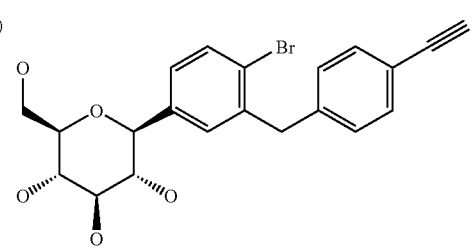 |
| (48) | 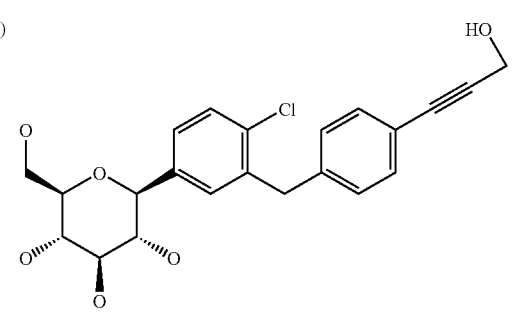 |
| (49) | 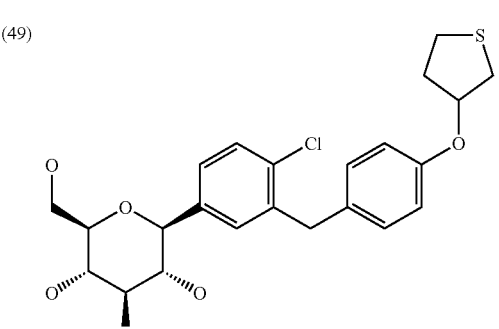 |
| (50) | 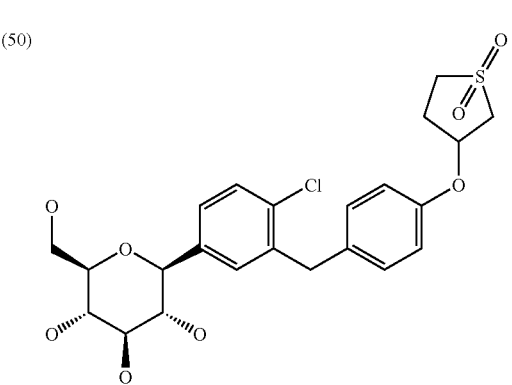 |

| Ex. | Structure |
|---|---|
| (51) | 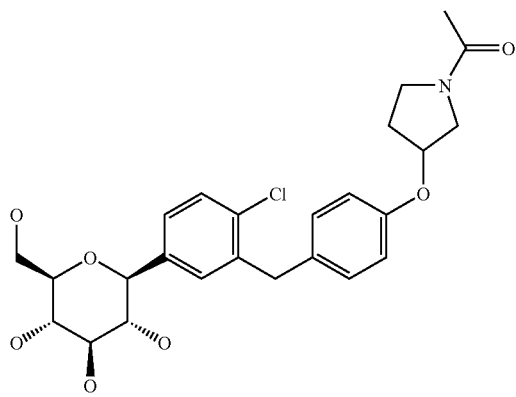 |
| (52) | 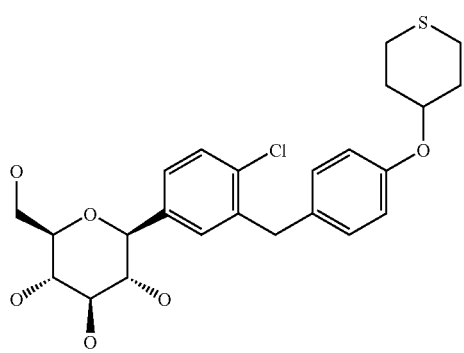 |
| (53) | 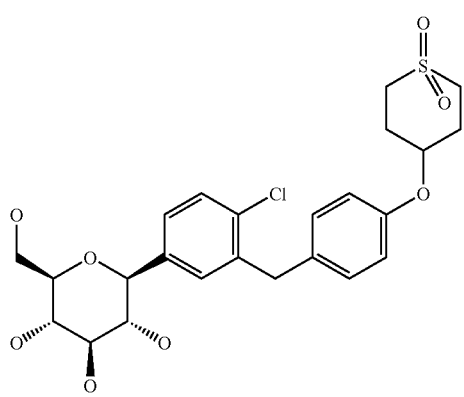 |
| (54) | 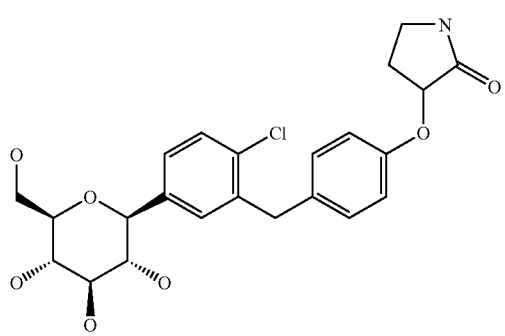 |

| Ex. | Structure |
|---|---|
| (55) | 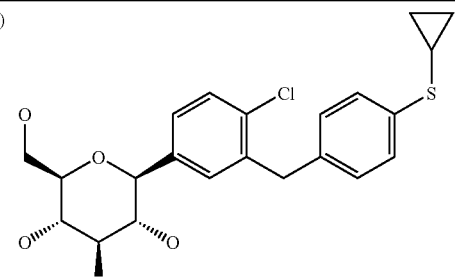 |
| (56) | 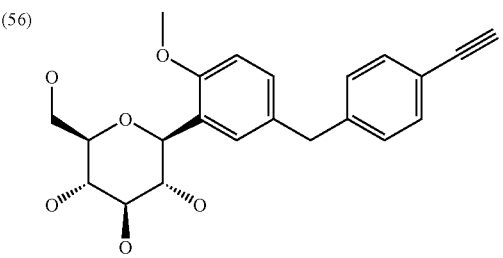 |
| (57) | 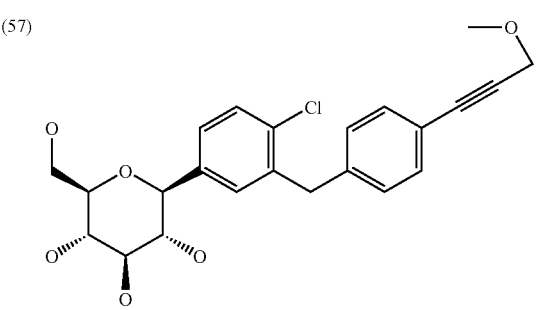 |

Some examples of formulations will now be described in which the term "active substance" denotes one or more compounds according to the invention, including the salts thereof. In the case of one of the combinations with one or additional active substances as described previously, the term "active substance" also includes the additional active substances.

EXAMPLE A

Tablets containing 100 mg of active substance
Composition:

1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

| Weight of tablet: | 220 mg |
| --- | --- |
| Diameter: | 10 mm, biplanar, facetted on both sides and notched on one side. |

EXAMPLE B

| Tablets containing 150 mg of active substance Composition: | |
| --- | --- |
| 1 tablet contains: | |
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| Weight of tablet: | 300 mg |
| --- | --- |
| die: | 10 mm, flat |

EXAMPLE C

| Hard gelatine capsules containing 150 mg of active substance Composition: | |
| --- | --- |
| 1 capsule contains: | |
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

| Capsule filling: | approx. 320 mg |
| --- | --- |
| Capsule shell: | size 1 hard gelatine capsule. |

EXAMPLE D

| Suppositories containing 150 mg of active substance Composition: | |
| --- | --- |
| 1 suppository contains: | |
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE E

| Ampoules containing 10 mg active substance Composition: | |
| --- | --- |
| active substance | 10.0 mg |
| 0.01 N hydrochloric acid q.s. | |
| double-distilled water | ad 2.0 ml |

Preparation:

The active substance is dissolved in the necessary amount of 0.01 N HCl, made isotonic with common salt, filtered sterile and transferred into 2 ml ampoules.

EXAMPLE F

| Ampoules containing 50 mg of active substance Composition: | |
| --- | --- |
| active substance | 50.0 mg |
| 0.01 N hydrochloric acid q.s. | |
| double-distilled water | ad 10.0 ml |

Preparation:

The active substance is dissolved in the necessary amount of 0.01 N HCl, made isotonic with common salt, filtered sterile and transferred into 10 ml ampoules.

What is claimed is:
1. Glucopyranosyl-substituted benzene derivatives of general formula I.2c

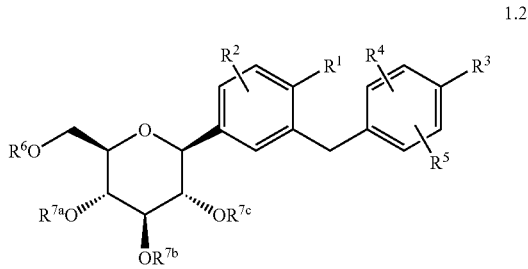

wherein
- $R^1$ is selected from hydrogen, fluorine, chlorine, bromine, cyano, methyl, ethyl, isopropyl, ethynyl, hydroxy, methoxy, ethoxy, cyclobutyloxy, cyclopentyloxy, cyclohexyloxy, and
- $R^2$ is hydrogen, fluorine, hydroxy, methoxy, ethoxy or methyl, and
- $R^3$ is selected from trimethylsilylethyl, ethynyl, 2-hydroxyprop-2-ylethynyl, 2-methoxyprop-2-ylethynyl, 3-hydroxy-1-propyn-1-yl, 3-methoxy-1-propyn-1-yl, cyclopropyloxy, cyclobutyloxy, cyclopentyloxy, cyclohexyloxy, tetrahydrofuran-3-yloxy, tetrahydropyran-4-yloxy, piperidin-4-yloxy, N-methylpiperidin-4-yloxy and N-acetylpiperidin-4-yloxy, and
- $R^4$, $R^5$ independently of one another is hydrogen or fluorine, and
- $R^6$ is hydrogen, $(C_{1-6}$-alkyl)carbonyl or $(C_{1-6}$-alkyl)oxycarbonyl, and
- $R^{7a}$, $R^{7b}$ and $R^{7c}$ are hydrogen, while, unless otherwise stated, the above-mentioned alkyl groups may be straight-chain or branched, the stereoisomers thereof, the mixtures thereof and the salts thereof.

2. Glucopyranosyl-substituted benzene derivatives according to claim 1, wherein $R^1$ is methyl or chlorine.

3. Glucopyranosyl-substituted benzene derivatives according to claim 1, wherein $R^3$ is ethynyl.

4. Glucopyranosyl-substituted benzene derivatives according to claim 1, wherein $R^3$ is trimethylsilylethyl.

5. Glucopyranosyl-substituted benzene derivatives according to claim 1, wherein $R^3$ is cyclobutyloxy.

6. Glucopyranosyl-substituted benzene derivatives according to claim 1, wherein $R^3$ is cyclopentyloxy.

7. Glucopyranosyl-substituted benzene derivatives according to claim 1, wherein $R^3$ is cyclohexyloxy.

8. Glucopyranosyl-substituted benzene derivatives according to claim 1, wherein $R^3$ is tetrahydrofuran-3-yloxy.

9. Glucopyranosyl-substituted benzene derivatives according to claim 1, wherein $R^3$ is tetrahydropyran-4-yloxy.

10. Glucopyranosyl-substituted benzene derivatives according to claim 1, wherein $R^2$ is hydrogen or methyl.

11. Glucopyranosyl-substituted benzene derivatives according to claim 1, wherein $R^2$ is hydrogen.

12. Glucopyranosyl-substituted benzene derivatives according to claim 1, wherein $R^4$ and $R^5$ are hydrogen.

13. Glucopyranosyl-substituted benzene derivatives according to claim 1, wherein $R^6$ is hydrogen.

14. 1-Chloro-2-(4-cyclopentyloxybenzyl)-4-(β-D-glucopyranos-1-yl)-benzene.

15. 1-Chloro-4-(β-D-glucopyranos-1-yl)-2-[4-((R)-tetrahydrofuran-3-yloxy)-benzyl]-benzene.

16. 1-Chloro-4-(β-D-glucopyranos-1-yl)-2-[4-((S)-tetrahydrofuran-3-yloxy)-benzyl]-benzene.

17. 1-Chloro-4-(β-D-glucopyranos-1-yl)-2-(4-cyclobutyloxy-benzyl)-benzene.

18. 1-Chloro-4-(β-D-glucopyranos-1-yl)-2-(4-cyclohexyloxy-benzyl)-benzene.

19. 1-Chloro-4-(β-D-glucopyranos-1-yl)-2-[4-(tetrahydropyran-4-yloxy)-benzyl]-benzene.

20. 1-Chloro-4-(β-D-glucopyranos-1-yl)-2-[4-(1-acetyl-piperidin-4-yloxy)-benzyl]-benzene.

21. 1-(β-D-Glucopyranos-1-yl)-4-methyl-3-[4-(2-trimethylsilyl-ethyl)-benzyl]-benzene.

22. 1-Chloro-4-(β-D-glucopyranos-1-yl)-2-(4-ethynyl-benzyl)-benzene.

23. 1-Fluoro-4-(β-D-glucopyranos-1-yl)-2-(4-ethynyl-benzyl)-benzene.

24. 1-(β-D-Glucopyranos-1-yl)-3-(4-ethynyl-benzyl)-benzene.

25. 1-Methoxy-4-(β-D-glucopyranos-1-yl)-2-(4-ethynyl-benzyl)-benzene.

* * * * *

UNITED STATES PATENT AND TRADEMARK OFFICE
CERTIFICATE OF CORRECTION

| | | |
|---|---|---|
| PATENT NO. | : 7,579,449 B2 | Page 1 of 1 |
| APPLICATION NO. | : 11/080150 | |
| DATED | : August 25, 2009 | |
| INVENTOR(S) | : Eckhardt et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 235 days.

Signed and Sealed this
First Day of March, 2011

David J. Kappos
*Director of the United States Patent and Trademark Office*